(12) United States Patent
Knobelsdorf et al.

(10) Patent No.: US 6,703,425 B2
(45) Date of Patent: Mar. 9, 2004

(54) SULFONAMIDE DERIVATIVES

(75) Inventors: James Allen Knobelsdorf, Noblesville, IN (US); Timothy Alan Shepherd, Indianapolis, IN (US); Eric George Tromiczak, Indianapolis, IN (US); Hamideh Zarrinmayeh, Carmel, IN (US); Dennis Michael Zimmerman, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/276,738

(22) PCT Filed: May 30, 2001

(86) PCT No.: PCT/US01/10840
§ 371 (c)(1),
(2), (4) Date: Nov. 15, 2002

(87) PCT Pub. No.: WO01/96289
PCT Pub. Date: Dec. 20, 2001

(65) Prior Publication Data
US 2003/0229102 A1 Dec. 11, 2003

Related U.S. Application Data

(60) Provisional application No. 60/211,365, filed on Jun. 13, 2000.

(51) Int. Cl.⁷ .................. A61K 31/18; A61K 31/38; A61K 31/415; A61K 31/445; A61K 31/497
(52) U.S. Cl. .................. 514/605; 514/252.12; 514/315; 514/357; 514/394; 514/438; 514/459; 514/471; 514/601; 544/401; 544/398; 546/246; 546/338; 548/340.1; 548/335.1; 549/75; 549/426; 549/495
(58) Field of Search .................. 564/82; 546/246, 546/338; 548/340.1, 335.1; 544/401, 398; 549/75, 426, 495; 514/252.12, 315, 357, 394, 438, 459, 471, 601, 605

(56) References Cited

U.S. PATENT DOCUMENTS

| 5,936,000 A | 8/1999 | Romero et al. ............. 514/647 |
| 6,025,457 A | * 2/2000 | Ohno et al. .................. 528/170 |
| 6,303,816 B1 | 10/2001 | Arnold et al. ................. 564/82 |

FOREIGN PATENT DOCUMENTS

| EP | 0 860 428 | 2/1997 |
| EP | 0 937 708 | 2/1998 |
| WO | WO 00/06083 | 7/1998 |
| WO | WO 01/90055 | 5/2000 |
| WO | WO 01/90057 | 5/2000 |

* cited by examiner

Primary Examiner—Peter O'Sullivan
(74) Attorney, Agent, or Firm—John A. Cleveland, Jr.; Nelsen L. Lentz

(57) ABSTRACT

The present invention relates to a compound of formula (I) or a pharmaceutically acceptable salt thereof which is useful for the treatment of conditions associated with glutamate hypofunction, such as psychiatric and neurological disorders

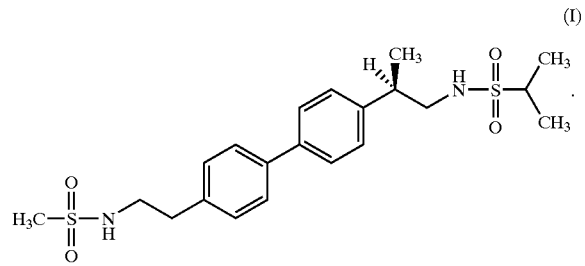

26 Claims, No Drawings

SULFONAMIDE DERIVATIVES

This is the national phase application, under 35 USC 371 for PCT/US01/10840, filed May 30, 2001 which claims the priority of 60/211,365 filed Jun. 13, 2000.

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic". This type of receptor has been subdivided into at least three subtypes, which are defined by the depolarizing actions of the selective agonists N-methyl-D-aspartate (NMDA), alpha-amino-3-hydroxy-5methylisoxazole4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in c-AMP formation, and changes in ion channel function. Schoepp and Conn, *Trends in Pharmacol. Sci.*, 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

AMPA receptors are assembled from four protein sub-units known as GluR1 to GluR4, while kainic acid receptors are assembled from the sub-units GluR5 to GluR7, and KA-1 and KA-2. Wong and Mayer, *Molecular Pharmacology* 44:505–510, 1993. It is not yet known how these sub-units are combined in the natural state. However, the structures of certain human variants of each sub-unit have been elucidated, and cell lines expressing individual sub-unit variants have been cloned and incorporated into test systems designed to identify compounds which bind to or interact with them, and hence which may modulate their function. Thus, European patent application, publication number EP-A2-0574257 discloses the human sub-unit variants GluR1B, GluR2B, GluR3A and GluR3B. European patent application, publication number EP-A1-0583917 discloses the human sub-unit variant GluR4B.

One distinctive property of AMPA and kainic acid receptors is their rapid deactivation and desensitization to glutamate. Yamada and Tang, *The Journal of Neuroscience*, September 1993, 13(9):3904–3915 and Kathryn M. Partin, *J. Neuroscience*, Nov. 1, 1996, 16(21):6634–6647.

It is known that the rapid desensitization and deactivation of AMPA and/or kainic acid receptors to glutamate may be inhibited using certain compounds. This action of these compounds is often referred to in the alternative as "potentiation" of the receptors. One such compound, which selectively potentiates AMPA receptor function, is cyclothiazide. Partin et al., *Neuron.* Vol. 11, 1069–1082, 1993.

International Patent Application Publication WO 98/33496 published Aug. 6, 1998 discloses certain sulfonamide derivatives which are useful, for example, for treating psychiatric and neurological disorders, for example cognitive disorders; neuro-degenerative disorders such as Alzheimer's disease; age-related dementias; age-induced memory impairment; movement disorders such as tardive dyskinesia, Huntington's chorea, myoclonus, and Parkinson's disease; reversal of drug-induced states (such as cocaine, amphetamines, alcohol-induced states); depression; attention deficit disorder; attention deficit hyperactivity disorder, psychosis; cognitive deficits associated with psychosis, and drug-induced psychosis.

The present invention provides compounds of formula I:

formula I

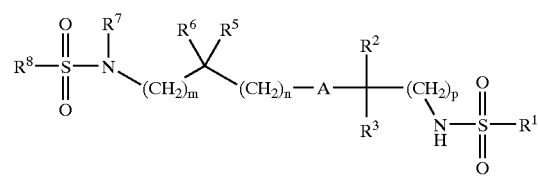

wherein A represents

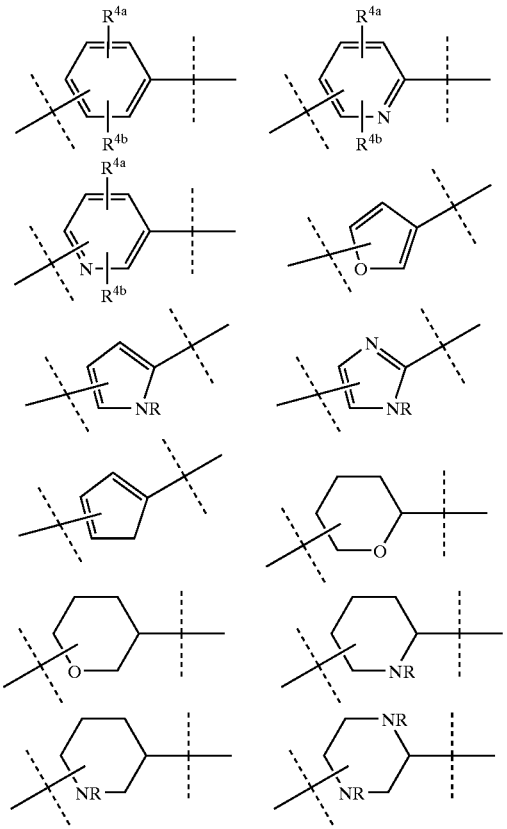

-continued

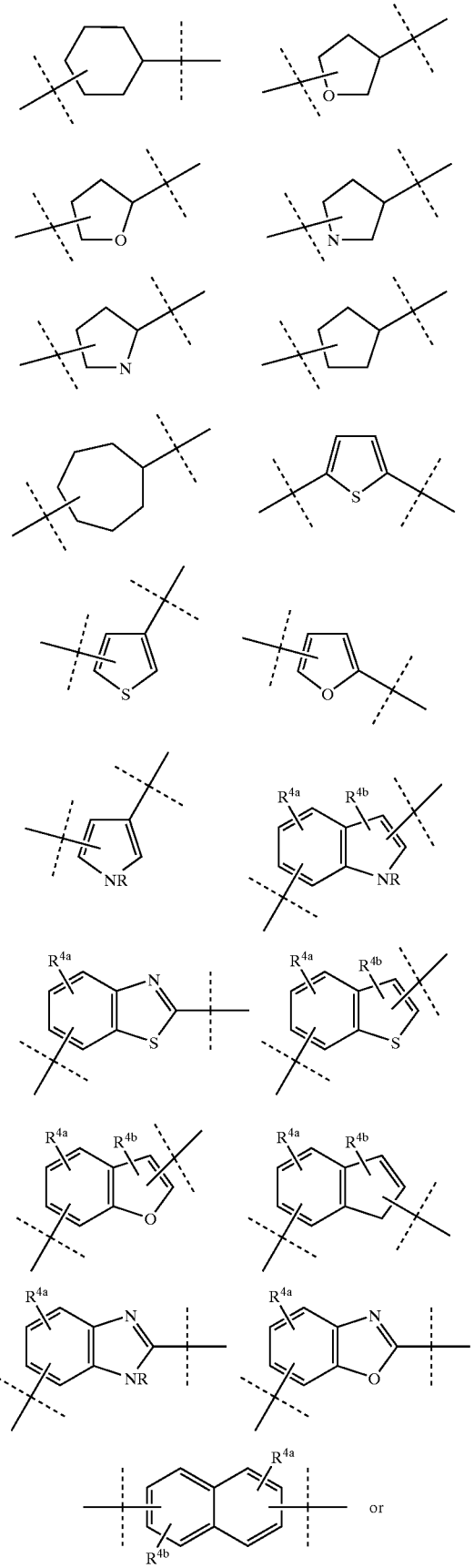

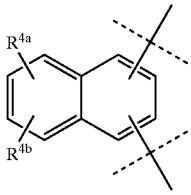

R represents hydrogen or (1–4C)alkyl;
R$^1$ represents (1–6C)alkyl, (2–6C)alkenyl, or NR$^9$R$^{10}$;
R$^2$ and R$^3$ each independently represent hydrogen, (1–4C) alkyl, F, or —OR$^{11}$;
R$^{4a}$ and R$^{4b}$ each independently represent hydrogen, (1–4C) alkyl, (1–4C)alkoxy, I, Br, Cl, or F;
R$^5$ and R$^6$ each independently represent hydrogen, (1–4C) alkyl, F, or —OR$^{11}$;
R$^7$ represents hydrogen, or (1–4C)alkyl;
R$^8$ represents (1–6C)alkyl, unsubstituted or substituted aromatic group, unsubstituted or substituted heteroaromatic group, cycloalkyl, or alkylcycloalkyl;
n is zero or an integer 1, 2, 3, 4, or 5;
m is zero or an integer 1, 2, 3, 4, or 5;
p is an integer 1 or 2;
R$^9$ and R$^{10}$ each independently represent hydrogen or (1–4C)alkyl; and
R$^{11}$ represents hydrogen or (1–4C)alkyl;
or a pharmaceutically acceptable salt thereof.

The present invention further provides compounds of formula Ia:

formula Ia

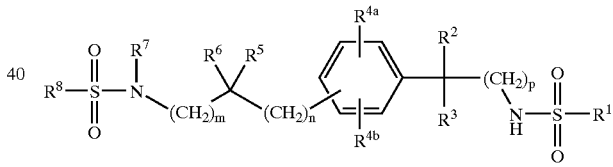

wherein
R$^1$ represents (1–6C)alkyl, (2–6C)alkenyl, or NR$^9$R$^{10}$;
R$^2$ and R$^3$ each independently represent hydrogen, (1–4C) alkyl, F, or —OR$^{11}$;
R$^{4a}$ and R$^{4b}$ each independently represent hydrogen, (1–4C) alkyl, (1–4C)alkoxy, I, Br, Cl, or F;
R$^5$ and R$^6$ each independently represent hydrogen, (1–4C) alkyl, F, or —OR$^{11}$;
R$^7$ represents hydrogen, or (1–4C)alkyl;
R$^8$ represents (1–6C)alkyl, unsubstituted or substituted aromatic group, unsubstituted or substituted heteroaromatic group, cycloalkyl, or alkylcycloalkyl;
n is zero or an integer 1, 2, 3, 4, or 5;
m is zero or an integer 1, 2, 3, 4, or 5;
p is an integer 1 or 2;
R$^9$ and R$^{10}$ each independently represent hydrogen or (1–4C)alkyl; and
R$^{11}$ represents hydrogen or (1–4C)alkyl;
or a pharmaceutically acceptable salt thereof.

The present invention further provides a method of potentiating glutamate receptor function in a patient, which comprises administering to said patient an effective amount of a compound of formula I.

The present invention provides a method of treating cognitive disorders in a patient, which comprises administering to said patient an effective amount of a compound of formula I.

In addition, the present invention further provides a method of treating cognitive deficits associated with psychosis in a patient, which comprises administering to said patient an effective amount of a compound of formula I.

According to another aspect, the present invention provides the use of a compound of formula I, or a pharmaceutically acceptable salt thereof for the manufacture of a medicament for potentiating glutamate receptor function.

In addition, the present invention provides the use of a compound of formula I or a pharmaceutically acceptable salt thereof for potentiating glutamate receptor function.

The invention further provides pharmaceutical compositions comprising, a compound of formula I and a pharmaceutically acceptable diluent or carrier.

This invention also encompasses novel intermediates, and processes for the synthesis of the compounds of formula I.

In this specification, the term "potentiating glutamate receptor function" refers to any increased responsiveness of glutamate receptors, for example AMPA receptors, to glutamate or an agonist, and includes but is not limited to inhibition of rapid desensitization or deactivation of AMPA receptors to glutamate.

A wide variety of conditions may be treated or prevented by the compounds of formula I and their pharmaceutically acceptable salts through their action as potentiators of glutamate receptor function. Such conditions include those associated with glutamate hypofunction, such as psychiatric and neurological disorders, for example cognitive disorders and neuro-degenerative disorders such as Alzheimer's disease; age-related dementias; age-induced memory impairment; mild cognitive impairment, cognitive deficits due to autism, Down's syndrome and other central nervous system disorders with childhood onset, cognitive deficits post electroconvulsive therapy, movement disorders such as tardive dyskinesia, Hungtington's chorea, myoclonus, dystonia, spasticity, and Parkinson's disease; reversal of drug-induced states (such as cocaine, amphetamines, alcohol-induced states); depression; attention deficit disorder, attention deficit hyperactivity disorder; psychosis; cognitive deficits associated with psychosis, drug-induced psychosis, stroke, and sexual dysfunction. The compounds of formula I may also be useful for improving memory (both short term and long term) and learning ability. The present invention provides the use of compounds of formula I for the treatment of each of these conditions.

The present invention includes the pharmaceutically acceptable salts of the compounds defined by formula I. A compound of this invention can possess a sufficiently acidic group, a sufficiently basic group, or both functional groups, and accordingly react with any of a number of organic and inorganic bases, and inorganic and organic acids, to form a pharmaceutically acceptable salt. The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts. Such salts include the pharmaceutically acceptable salts listed in *Journal of Pharmaceutical Science*, 66, 2–19 (1977) which are known to the skilled artisan.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprate, caprylate, acrylate, ascorbate, formate, hydrochloride, dihydrochloride, isobutyrate, caproate, heptanoate, propiolate, propionate, phenylpropionate, salicylate, oxalate, malonate, succinate, suberate, sebacate, fumarate, malate, maleate, hydroxymaleate, mandelate, nicotinate, isonicotinate, cinnamate, hippurate, nitrate, phthalate, teraphthalate, butyne-1,4-dioate, butyne-1,4-dicarboxylate, hexyne-1,4-dicarboxylate, hexyne-1,6-dioate, benzoate, chlorobenzoate, methylbenzoate, hydroxybenzoate, methoxybenzoate, dinitrobenzoate, o-acetoxybenzoate, naphthalene-2-benzoate, phthalate, p-toluenesulfonate, p-bromobenzenesulfonate, p-chlorobenzenesulfonate, xylenesulfonate, phenylacetate, trifluoroacetate, phenylpropionate, phenylbutyrate, citrate, lactate, α-hydroxybutyrate, glycolate, tartrate, benzenesulfonate, methanesulfonate, ethanesulfonate, propanesulfonate, hydroxyethanesulfonate, 1-naphthalenesulfonate, 2-napthalenesulfonate, 1,5-naphthalenedisulfonate, mandelate, tartarate, and the like. Preferred pharmaceutically acceptable acid addition salts are those formed with mineral acids such as hydrochloric acid and hydrobromic acid, and those formed with organic acids such as maleic acid, oxalic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that the above salts may form hydrates or exist in a substantially anhydrous form.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of formula I can be prepared by one of ordinary skill in the art utilizing well known techniques and processes, such as those disclosed by J. Jacques, et al., "*Enantiomers, Racemates, and Resolutions*", John Wiley and Sons, Inc., 1981, and E. L. Eliel and S. H. Wilen, "*Stereochemistry of Organic Compounds*", (Wiley-Interscience 1994), and European Patent Application No. EP-A-838448, published Apr. 29, 1998. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term NS" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

As used herein, the term "aromatic group" means the same as aryl, and includes phenyl and a polycyclic aromatic carbocyclic ring such as 1- or 2-naphthyl, 1,2-dihydronaphthyl, 1,2,3,4-tetrahydronaphthyl, and the like.

The term "heteroaromatic group" includes an aromatic 5–6 membered ring containing from one to four heteroatoms selected from oxygen, sulfur and nitrogen, and a bicyclic group consisting of a 5–6 membered ring containing from one to four heteroatoms selected from oxygen, sulfur and nitrogen fused with a benzene ring or another 5–6 membered ring containing one to four atoms selected from oxygen, sulfur and nitrogen. Examples of heteroaromatic groups are thienyl, furyl, oxazolyl, isoxazolyl, oxadiazoyl, pyrazolyl, thiazolyl, thiadiazolyl, isothiazolyl, imidazolyl, trazolyl, tetrazolyl, pyrdyl, pyridazinyl, pyrimidyl, benzofuryl, benzothienyl, benzimidazolyl, benzoxazolyl, benzothiazolyl, indolyl, and quinolyl.

The term "substituted" as used in the term "substituted aromatic or heteroaromatic group" herein signifies that one or more (for example one or two) substituents may be present, said substituents being selected from atoms and groups which, when present in the compound of formula I, do not prevent the compound of formula I from functioning as a potentiator of glutamate receptor function.

Examples of substituents which may be present in a substituted aromatic or heteroaromatic group include I, Br, Cl, F, $NH_2$, $NO_2$, cyano; (1–6C) alkyl, (1–6C)alkoxy, (2–6C)alkenyl, (2–6C)alkynyl, (3–8C)cycloalkyl, and halo (1–6C)alkyl.

The term (1–10C)alkyl includes (1–8C)alkyl, (1–6C)alkyl and (1–4C)alkyl. Particular values are methyl, ethyl, propyl, isopropyl, butyl, isobutyl, t-butyl, pentyl, hexyl, heptyl, octyl, nonyl and decyl.

The term (2–6C)alkenyl includes (2–4C)alkenyl. Particular values are vinyl and prop-2-enyl.

The term (2–6C)alkynyl includes (3–4C)alkynyl. A particular value is prop-2-ynyl.

The term cycloalkyl, includes monocyclic and polycyclic groups. Particular values are (3–8C)cycloalkyl, (5–8C)cycloalkyl, and (4–6C)cycloalkyl, such as cyclopropyl, cyclobutyl, cyclopentyl, cyclohexyl, cycloheptyl, and bicyclo[2.2.2]octane.

As used herein the term "Hal", "halogen", or "halide" refers to the halogen atoms I, Br, Cl, or F, unless otherwise specified.

The term halo(1–6C)alkyl includes fluoro(1–6C)alkyl, such as trifluoromethyl and 2,2,2-trifluoroethyl, and chloro (1–6C)alkyl such as chloromethyl.

The term (2–4C)alkylene includes ethylene, propylene and butylene. A preferred value is ethylene.

The term (1–6C)alkoxy, refers to a straight or branched alkyl chain having from one to six carbon atoms attached to an oxygen atom and includes (1–4C)alkoxy, such as methoxy, ethoxy, propoxy, isopropoxy, isobutoxy, tert-butoxy, pentoxy, and the like.

The term thienyl includes thien-2-yl and thien-3-yl.

The term furyl includes fur-2-yl and fur-3-yl.

The term oxazolyl includes oxazol-2-yl, oxazol-4-yl and oxazol-5-yl.

The term isoxazolyl includes isoxazol-3-yl, isoxazol-4-yl and isoxazol-5-yl.

The term oxadiazolyl includes [1,2,4]oxadiazol-3-yl and [1,2,4]oxadiazol-5-yl.

The term pyrazolyl includes pyrazol-3-yl, pyrazol-4-yl and pyrazol-5-yl.

The term thiazolyl includes thiazol-2-yl, thiazol-4-yl and thiazol-5-yl.

The term thiadiazolyl includes [1,2,4]thiadiazol-3-yl, and [1,2,4]thiadiazol-5-yl.

The term isothiazolyl includes isothiazol-3-yl, isothiazol-4-yl and isothiazol-5-yl.

The term imidazolyl includes imidazol-2-yl, imidazolylyl-4-yl and imidazolyl-5-yl.

The term triazolyl includes [1,2,4]triazol-3-yl and [1,2,4]triazol-5-yl.

The term tetrazolyl includes tetrazol-5-yl.

The term pyridyl includes pyrid-2-yl, pyrid-3-yl and pyrid-4-yl.

The term pyridazinyl includes pyridazin-3-yl, pyridazin-4-yl, pyridazin-5-yl and pyridazin-6-yl.

The term pyrimidyl includes pyrimidin-2-yl, pyrimidin-4-yl, pyrimidin-5-yl and pyrimidin-6-yl.

The term benzofuryl includes benzofur-2-yl and benzofur-3-yl.

The term benzothienyl includes benzothien-2-yl and benzothien-3-yl.

The term benzimidazolyl includes benzimidazol-2-yl.

The term benzoxazolyl includes benzoxazol-2-yl.

The term benzothiazolyl includes benzothiazol-2-yl.

The term indolyl includes indol-2-yl and indol-3-yl.

The term quinolyl includes quinol-2-yl.

The term dihydrothiazolyl includes 4,5-dihydrothiazol-2-yl, and the term (1–4C)alkoxycarbonyldihydrothiazolyl indudes 4-methoxycarbonyl-4,5-dihydrothiazol-2-yl.

The term alkylcycloalkyl includes -(1–4C)alkyl(4–6C)cycloalkyl and -(1–4C)alkyl(3–8C)cycloalkyl such as the following:

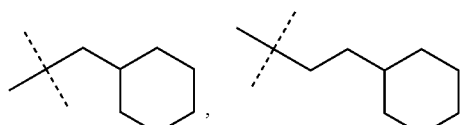,

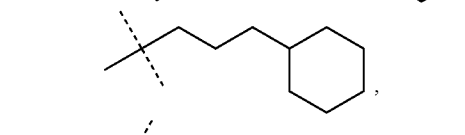,

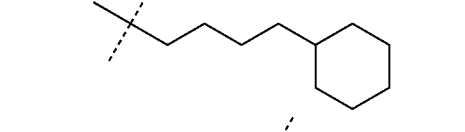,

 and

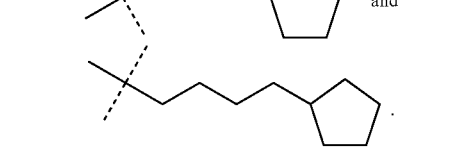.

The term -(1–4C)alkylaromatic includes the following:

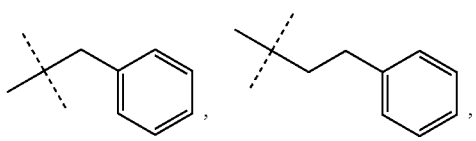,

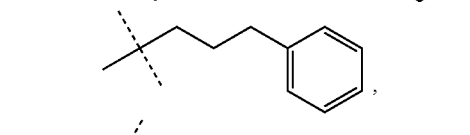,

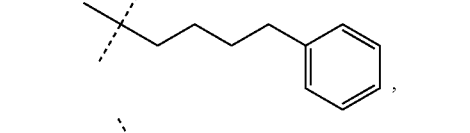,

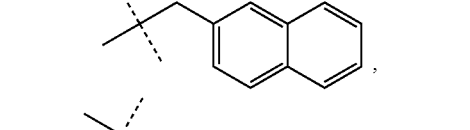,

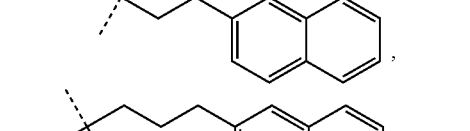,

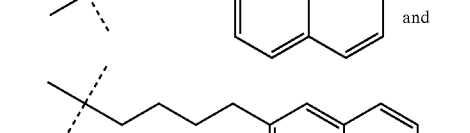 and

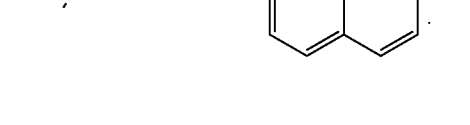.

The compounds of formula I can be prepared by one of ordinary skill in the art, for example, following the procedures set forth in the Schemes below. The reagents and starting materials are readily available to one of ordinary skill in the art. All substituents, unless otherwise specified are as previously defined.

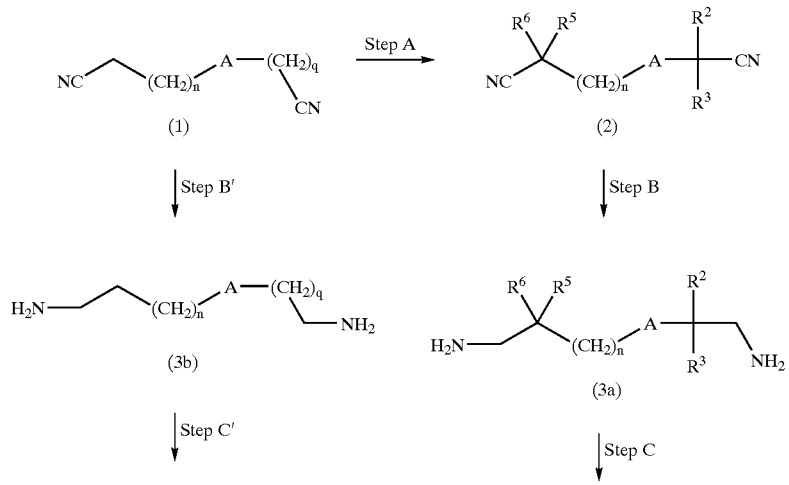

Scheme I

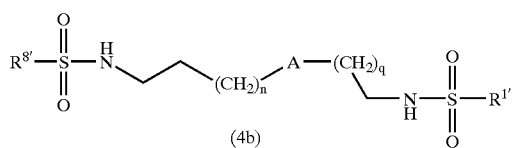 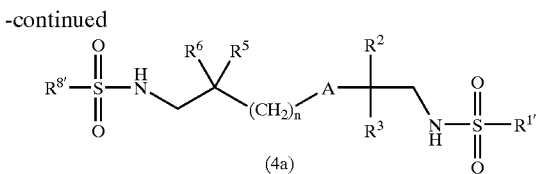

In Scheme I, step A, the dinitrile of structure (1) is alkylated under standard conditions well known in the art to provide the alkylated compound of structure (2) wherein q represents the integer 1. For example, dinitrile (1) is dissolved in a suitable organic, such as tetrahydrofuran (THF) and added to a suitable base, such as a stirring solution of about 2.05 equivalents methyllithium in THF at about −75° C. After addition is completed the reaction mixture is allowed to warm to room temperature and stirred for about 2 to 4 hours. The reaction mixture is then re-cooled to −75° C. and treated with about 2.05 equivalents of a suitable alkylating agent, such as methyl iodide. The reaction mixture is warmed to about 45° C. for about 1 hour and then the reaction is quenched with cold water and diluted with a suitable organic solvent, such as diethyl ether. The layers are separated and the organic phase is washed with dilute acid, water, dried over anhydrous magnesium sulfate, filtered, and concentrated under vacuum to provide the crude alkylated compound (2). This crude material can be purified by standard techniques well known in the art, such as chromatography on silica gel with a suitable eluent, such as ethyl acetate hexanes. One of ordinary skill in the art will appreciate that under the above conditions, one of $R^2$ and $R^3$ will be hydrogen and one of $R^5$ and $R^6$ will be hydrogen in the alkylated compound (2).

Alternatively, the dinitrile of structure (1) can be alkylated to provide alkylated compound (2) wherein none of the substituents $R^2$, $R^3$, $R^5$, and $R^6$ are hydrogen. For example, dinitrile (1) is added to about 4.2 equivalents of a suitable base, such as sodium hydride suspended in a suitable organic solvent, such as dimethylformamide (DMF) at about −15° C. The reaction mixture is stirred for about 30 minutes to 2 hours and then treated with about 4.2 equivalents of a suitable alkylating agent, such as methyl iodide. The reaction mixture is then allowed to warm to room temperature and stirred for about 12 hours. The alkylated compound (2) is then isolated under standard conditions. For example, the reaction mixture is poured into cold water and the resulting precipitate is collected by filtration, washed with cold water, and dried to provide alkylated compound (2).

In Scheme I, step B, alkylated compound (2) is then reduced to the diamino compound of structure (3a) under conditions well known in the art, for example see Reaction No. 6–27 in Jerry March "Advanced Organic Chemistry: Reactions, Mechanisms, and Structure," Fourth Edition, John Wiley & Sons, pages 918–919, 1992. More specifically, for example, the alkylated compound (2) is dissolved in a suitable organic solvent, such as THF and about 2.2 equivalents of a suitable reducing agent, such as borane-methyl sulfide complex is added. The reaction mixture is heated at reflux for about 30 minutes to about 12 hours and then allowed to cool to room temperature. The reaction mixture is then quenched with a solution of methanol saturated with HCl until the pH reaches about 2. The quenched reaction is then concentrated under vacuum, the residue dissolved in methanol and re-concentrated under vacuum to provide diamino (3a). This crude material can be carried on to the next step or it can be purified by standard techniques well known in the art, such as crystallization with a suitable solvent, such as methanol.

Alternatively, for example, compound (2), wherein $R^2$, $R^3$, $R^5$, and $R^6$ represent hydrogen, is combined with liquid ammonia, methanol, and a suitable hydrogenation catalyst, such as Raney® nickel. The reaction mixture is placed under hydrogen gas at about 300 psi (2068 kPa) for about 10 hours. The reaction mixture is then filtered through Celite® and the filtrate is concentrated under vacuum to provide diamino compound (3a).

In Scheme I, step C, the diamino compound (3a) is sulfonylated under standard conditions to provide bis-sulfonamide of structure (4a). For example, the compound (3a) is dissolved in a suitable organic solvent. Examples of suitable organic solvents include methylene chloride, tetrahydrofuran, and the like. The solution is treated with a slight excess of a suitable base. Examples of suitable bases include triethylamine, pyridine, 1,8-diazabicyclo[5.4.0]undec-7-ene (DBU), and the like. To the stirring solution is added about 2 equivalents of a compound of either formula $LgSO_2R^{1'}$ or $LgSO_2R^{8'}$. It is understood that under these reaction conditions, $R^{1'}$ and $R^{8'}$ will be equivalent in the sulfonamide (4a). In addition, under these conditions, $R^{1'}$ and $R^{8'}$ each represent (1–6C)alkyl. The term "Lg" as used herein refers to a suitable leaving group. Examples of suitable leaving groups include, Cl, Br, and the like. Cl is the preferred leaving group. The reaction mixture is stirred for about 0.5 hours to about 16 hours. The bis-sulfonamide (4a) is then isolated and purified by techniques well known in the art, such as extraction techniques and chromatography. For example, the mixture is washed with 10% sodium bisulfate, the layers separated and the aqueous extracted with several times with a suitable organic solvent, such as methylene chloride. The organic extracts are combined, dried over anhydrous sodium sulfate, filtered, and concentrated under vacuum. The residue is then purified by chromatography on silica gel with a suitable eluent such as ethyl acetate/hexane or methanol/methylene chloride to provide the sulfonamide (4a).

In Scheme I, step B', the dinitrile (1) is directly reduced to the diamino compound of structure (3b) wherein q represents zero, 1 or 2, in a manner analogous to the procedure described in Scheme I, step B.

In Scheme I, step C' the diamino (3b) is then sulfonylated with a compound of either formula $LgSO_2R^{1'}$ or $LgSO_2R^{8'}$ in a manner analogous to the procedure described in Scheme I, step C.

Scheme Ia
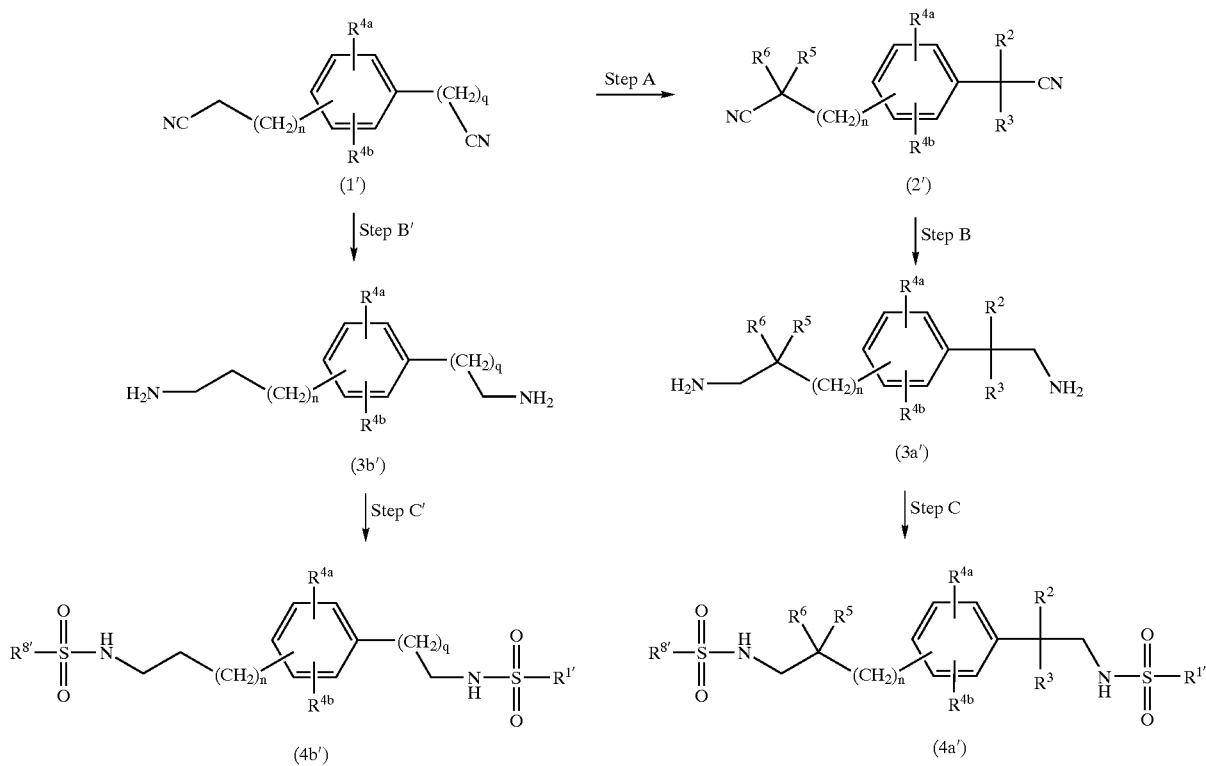
The compounds prepared in Scheme Ia are prepared by one of ordinary skill in the art in a manner analogous to the procedures set forth in Scheme I above.
Scheme II
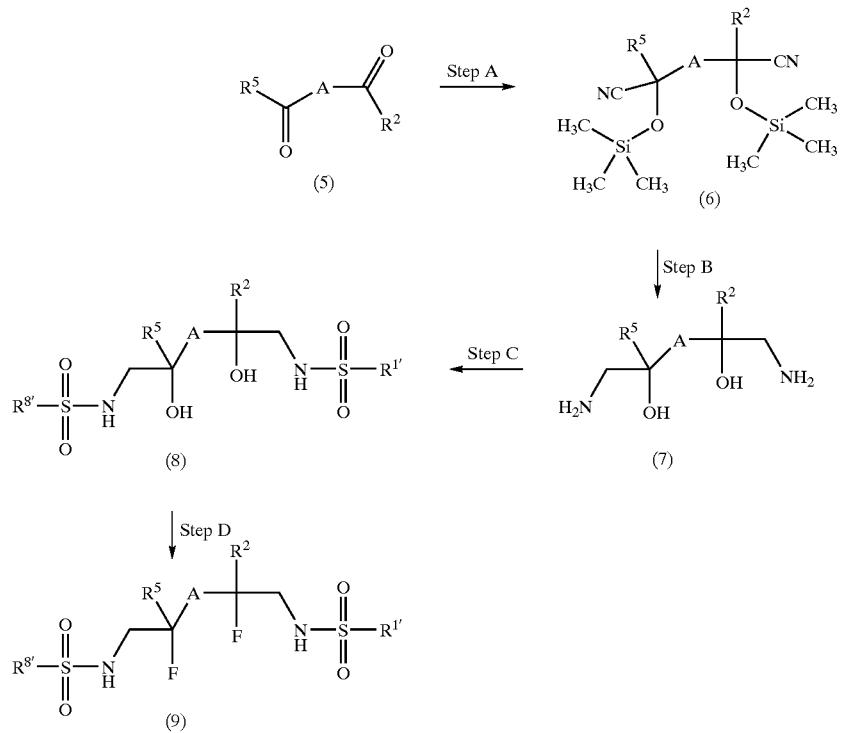

In Scheme II, step A, the diketone (5) is converted to the dinitrile of structure (6) under conditions well known in the art. For example, diketone (5) is combined with about 3 equivalents of trimethylsilyl cyanide and a catalytic amount of zinc iodide. The reaction mixture is stirred at room temperature for about 2 to 4 hours and then poured into aqueous sodium bicarbonate solution. The mixture is then extracted with a suitable organic solvent, such as ethyl acetate, the organic extracts are combined, washed with water, dried over anhydrous sodium sulfate, filtered, and concentrated under vacuum to provide crude dinitrile (6). This crude material can then be purified by standard techniques, such as chromatography on silica gel with a suitable eluent such as ethyl acetate/hexanes.

In Scheme II, step B, the dinitrile (6) is reduced in a manner analogous to the procedure described in Scheme I, step B to provide the diamino compound of structure (7).

In Scheme II, step C, the diamino compound (7) is sulfonylated in a manner analogous to the procedure described in Scheme I, step C, wherein $R^{1'}$ and $R^{8'}$ are equivalent and represent (1–6C) alkyl, to provide the bis-sulfonamide (8).

In Scheme II, step D, the bis-sulfonamide (8) is fluorinated under conditions well known in the art to provide the fluorinated compound of structure (9). For example, bis-sulfonamide (8) is dissolved in a suitable organic solvent, such as THF or methylene chloride and the solution is cooled to about −78° C. under an inert atmosphere, such as nitrogen. To this solution is added slowly, about 2 to about 3 equivalents of diethylaminosulfur trifluoride (DAST) dissolved in a suitable organic solvent, such as THF or methylene chloride with stirring. The reaction is then allowed to warm to room temperature and stir for about 12 hours. The reaction is then diluted with water and methylene chloride. The layers are separated and the organic layer is washed with water, dried over anhydrous sodium sulfate, filtered, and concentrated under vacuum to provide the crude fluorinated compound (9). This crude material can then be purified by standard techniques, such as chromatography on silica gel with a suitable eluent such as ethyl acetate/hexanes.

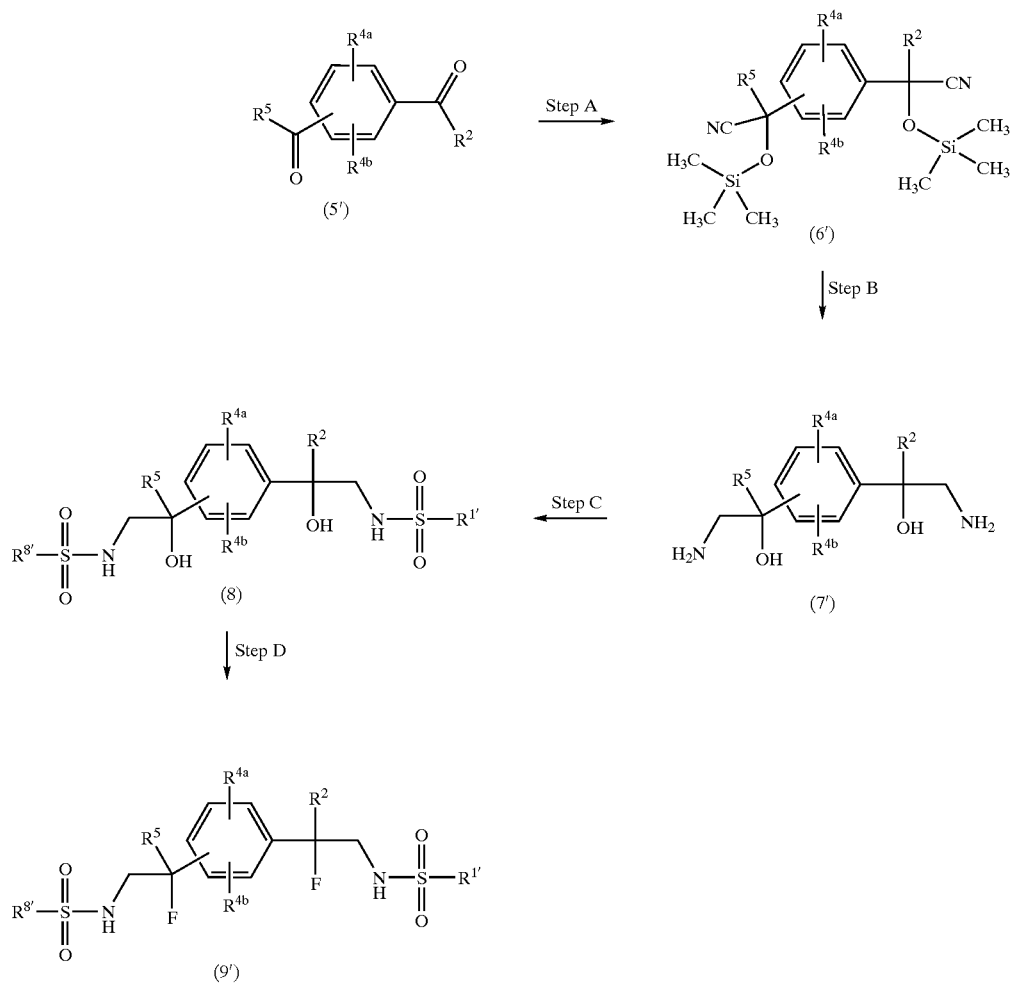

Scheme IIa

The compounds prepared in Scheme IIa are prepared by one of ordinary skill in the art in a manner analogous to the procedures set forth in Scheme II above.

Scheme III

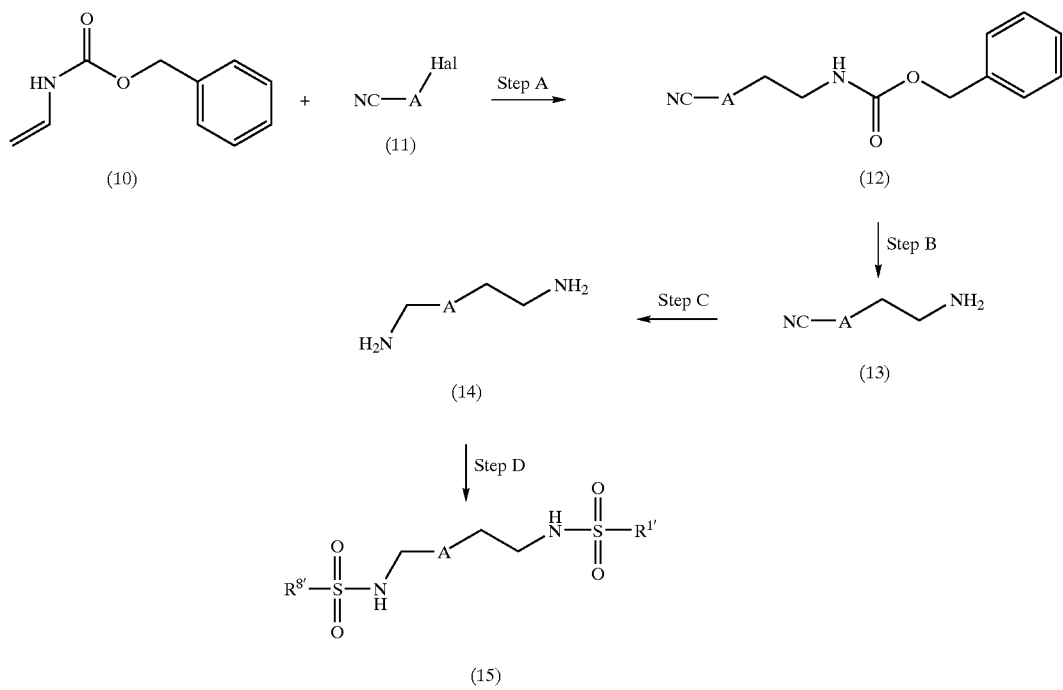

In Scheme III, step A, the carboxamide (10) is coupled with the aryl halide (11) under conditions well known in the art to provide the carboxamide of structure (12). For example, carboxamide (10) is dissolved in a suitable organic solvent, such as THF and cooled to about −10° C. The cooled solution is then treated with about 0.5 equivalents of (9-BBN)$_2$. The reaction mixture is then warmed to room temperature with stirring and quenched with aqueous sodium hydroxide. The quenched reaction mixture is then added to a solution of about 0.8 equivalents of aryl halide (11), a catalytic amount of PdCl$_2$(dppf) in a suitable organic solvent, such as THF, and the reaction is stirred at room temperature for about 12 hours. It is then quenched with a pH 7 buffer:hydrogen peroxide and extracted with a suitable organic solvent, such as ethyl acetate. The organic extracts are combined, washed with water, dried over anhydrous sodium sulfate, filtered, and concentrated under vacuum to provide crude carboxamide (12). This crude material can then be purified by standard techniques, such as chromatography on silica gel with a suitable eluent such as ethyl acetate/hexanes.

In Scheme III, step B, carboxamide (12) converted to the amine of structure (13) under conditions well known in the art, such as the conditions disclosed by Theodora W. Greene, "Protective Groups in Organic Synthesis," John Wiley & Sons, Inc., pages 238–241 (1981). More specifically, for example, the carboxamide (12) is dissolved in a suitable solvent mixture, such as THF/methanol and treated with a catalytic amount of a suitable hydrogenation catalyst, such as palladium on carbon. The reaction mixture is placed under an atmosphere of hydrogen for about 12 hours and then filtered through Celite®. The filtrate is concentrated under vacuum to provide crude amine (13). The crude material is filtered and concentrated under vacuum to provide amine (13).

In Scheme III, step C, the nitrile functionality of amine (13) is reduced in a manner analogous to the procedure described in Scheme I, step B to provide the diamino compound of structure (14). One of ordinary skill in the art will appreciate that less reducing agent will be required for the reduction in Scheme III, step C since only one nitrile functionality is being reduced as compared to the two nitrile functionalities being reduced in Scheme I, step B.

In Scheme III, step D, diamino compound (14) is sulfonylated in a manner analogous to the procedure described in Scheme I, step C, wherein $R^{1'}$ and $R^{8'}$ are equivalent and represent (1–6C) alkyl, to provide the bis-sulfonamide (15).

Scheme IIIa

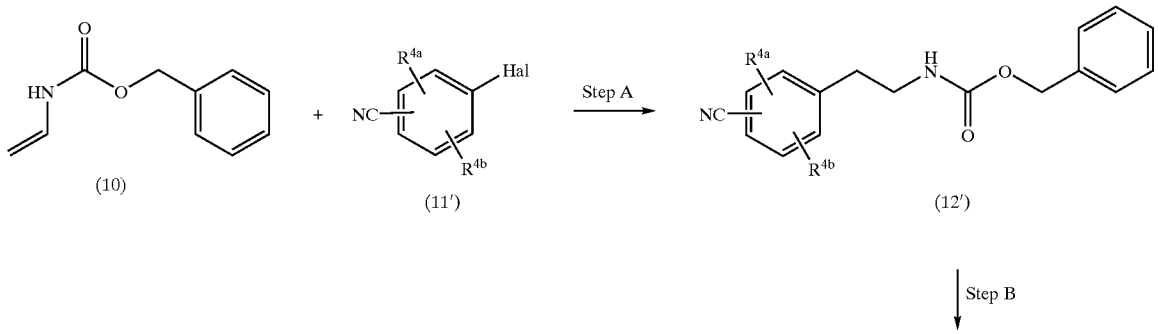

Step B

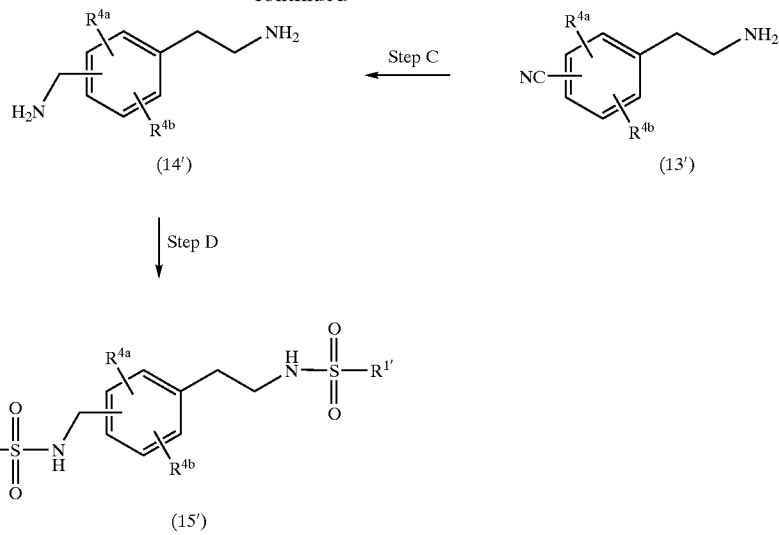

The compounds prepared in Scheme IIIa are prepared by one of ordinary skill in the art in a manner analogous to the procedures set forth in Scheme III above.

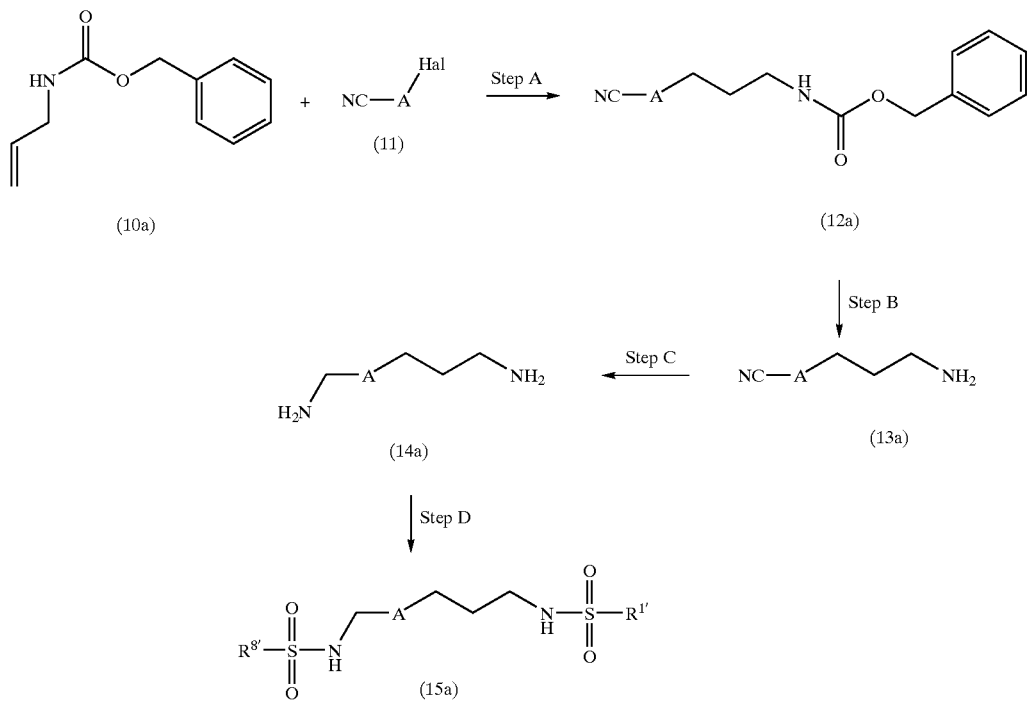

In Scheme IIIb, step A, the carboxamide (10a) is coupled with the aryl halide (11) in a manner analogous to the procedure described in Scheme III, step A to provide the carboxamide (12a).

In Scheme IIIb, step B, the carboxamide (12a) is converted to the amine (13a) in a manner analogous to the procedure described in Scheme III, step B.

In Scheme IIIb, step C, the amine (13a) is reduced in a manner analogous to the procedure described in Scheme III, step C to provide the diamino compound (14a).

In Scheme IIIb, step D, the diamino compound (14a) is sulfonylated in a manner analogous to the procedure described in Scheme III, step D to provide the bis-sulfonamide (15a).

Scheme IIIc

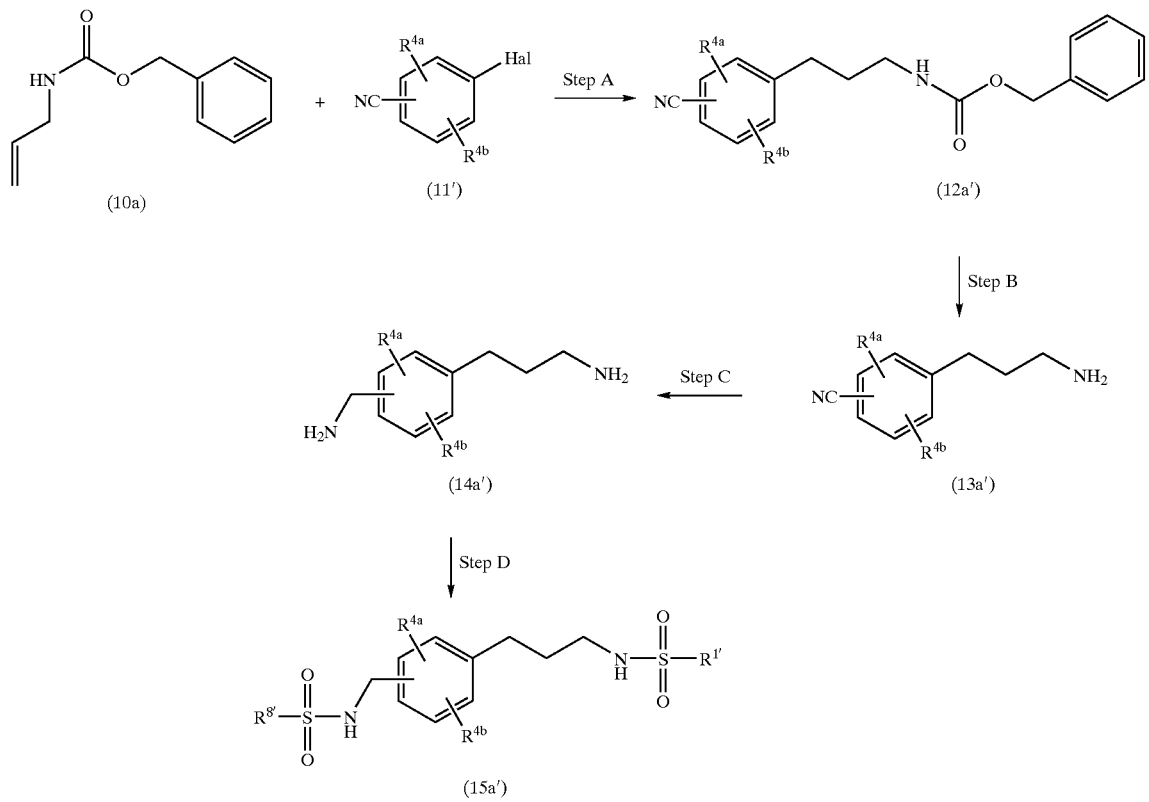

The compounds prepared in Scheme IIIc are prepared by one of ordinary skill in the art in a manner analogous to the procedures set forth in Scheme IIIb above.

Scheme IV

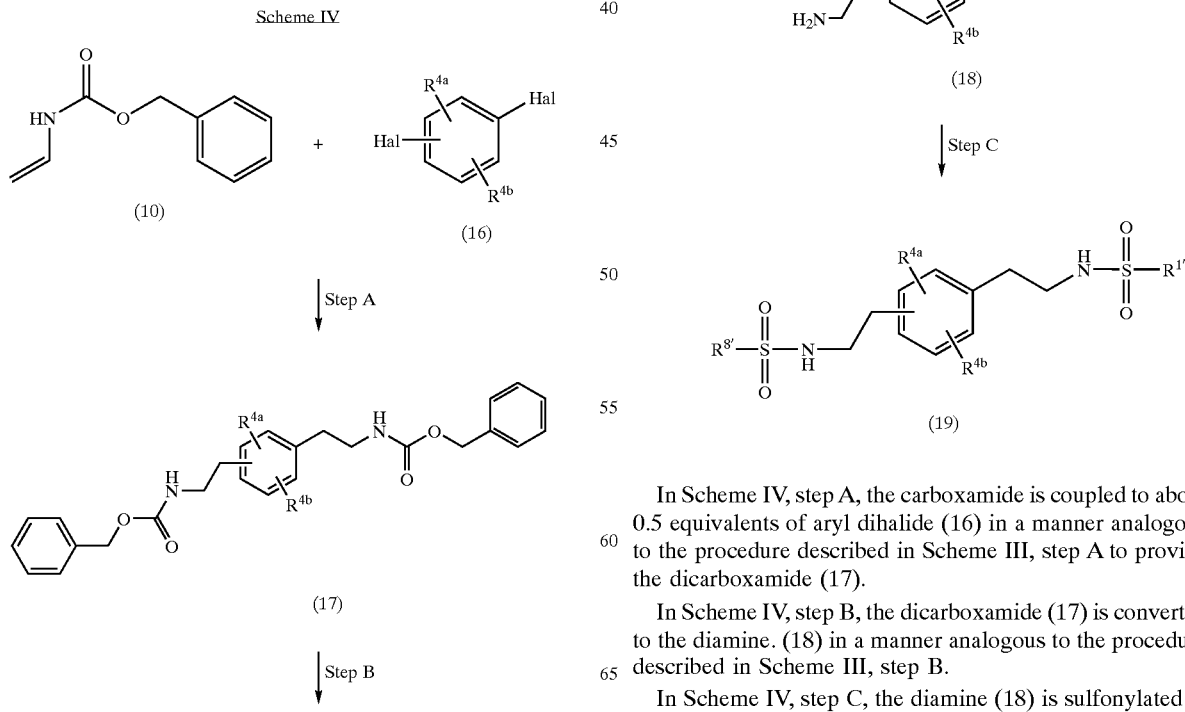

In Scheme IV, step A, the carboxamide is coupled to about 0.5 equivalents of aryl dihalide (16) in a manner analogous to the procedure described in Scheme III, step A to provide the dicarboxamide (17).

In Scheme IV, step B, the dicarboxamide (17) is converted to the diamine. (18) in a manner analogous to the procedure described in Scheme III, step B.

In Scheme IV, step C, the diamine (18) is sulfonylated in a manner analogous to the procedure described in Scheme III, step C, wherein $R^{1'}$ and $R^{8'}$ are equivalent and represent (1–6C) alkyl, to provide the bis-sulfonamide (19).

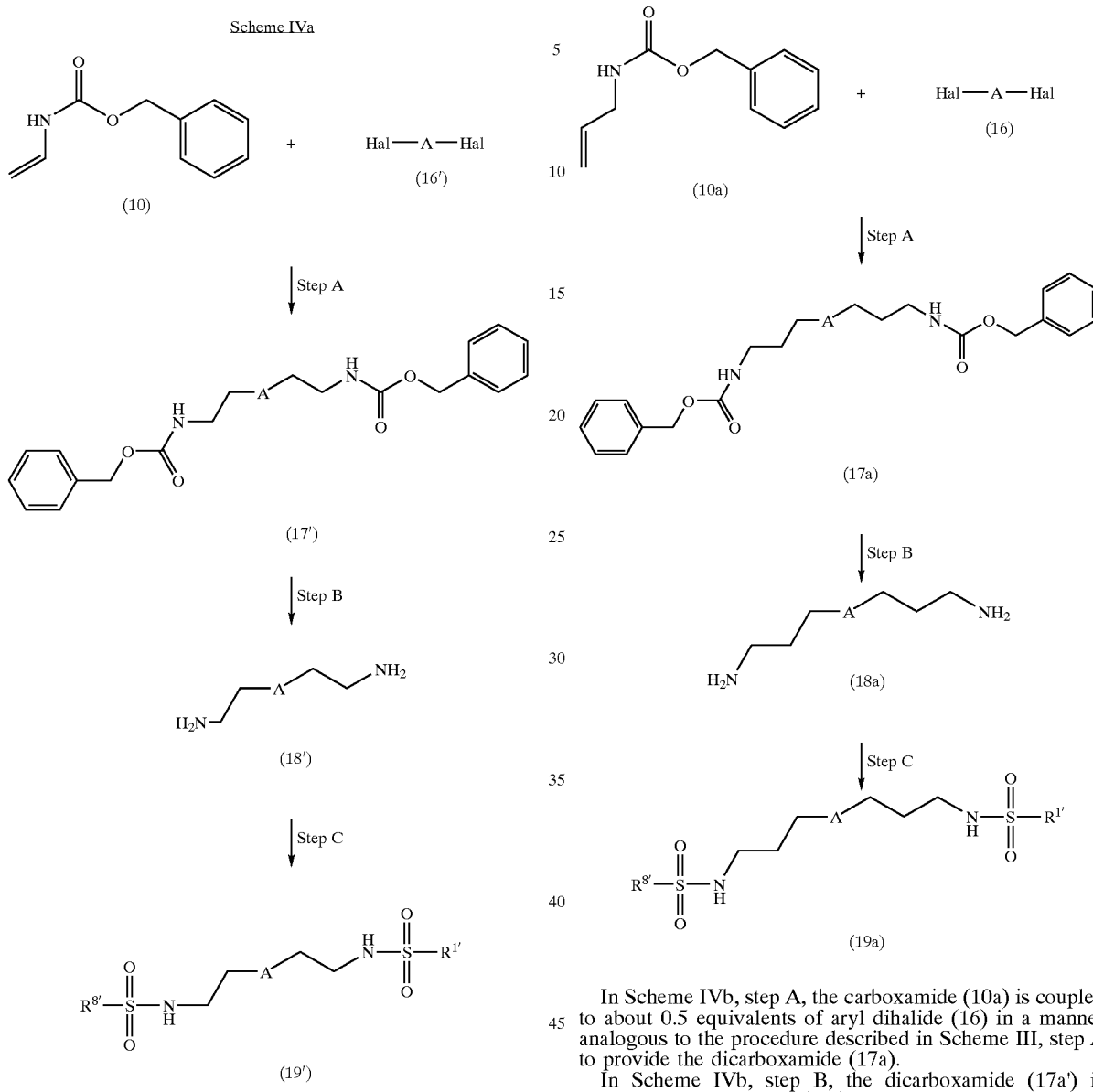

The compounds prepared in Scheme IVa are prepared by one of ordinary skill in the art in a manner analogous to the procedures set forth in Scheme IV above.

In Scheme IVb, step A, the carboxamide (10a) is coupled to about 0.5 equivalents of aryl dihalide (16) in a manner analogous to the procedure described in Scheme III, step A to provide the dicarboxamide (17a).

In Scheme IVb, step B, the dicarboxamide (17a') is converted to the diamine (18a) in a manner analogous to the procedure described in Scheme III, step B.

In Scheme IVb, step C, the diamine (18a) is sulfonylated in a manner analogous to the procedure described in Scheme III, step C, wherein $R^{1'}$ and $R^{8'}$ are equivalent and represent (1–6C) alkyl, to provide the bis-sulfonamide (19a).

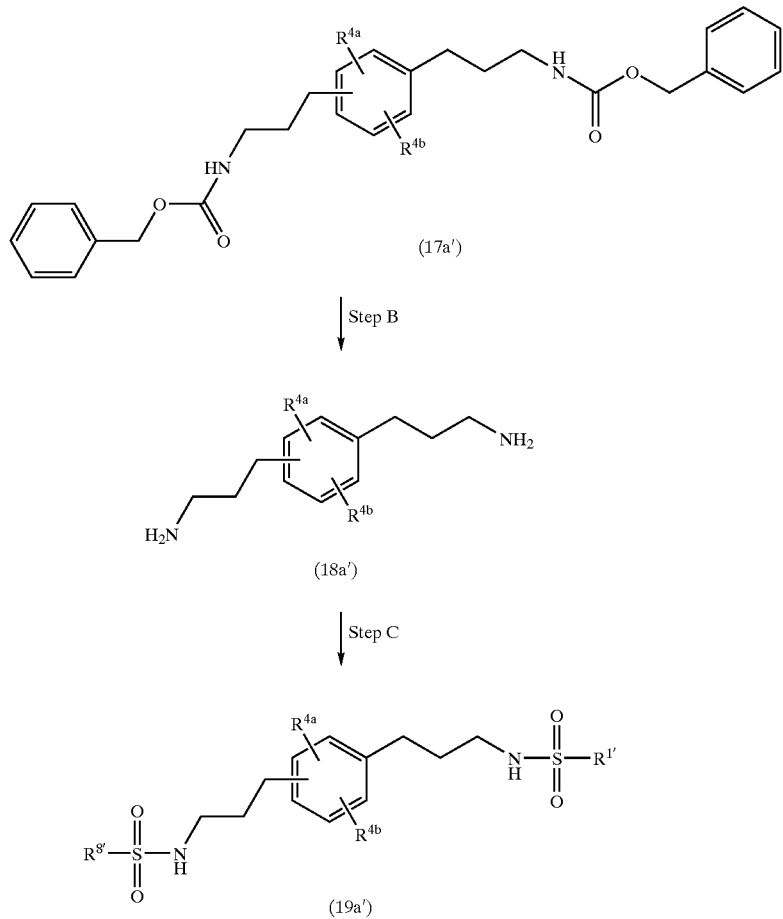

The compounds prepared in Scheme IVc are prepared by one of ordinary skill in the art in a manner analogous to the procedures set forth in Scheme IVb above.

Scheme V

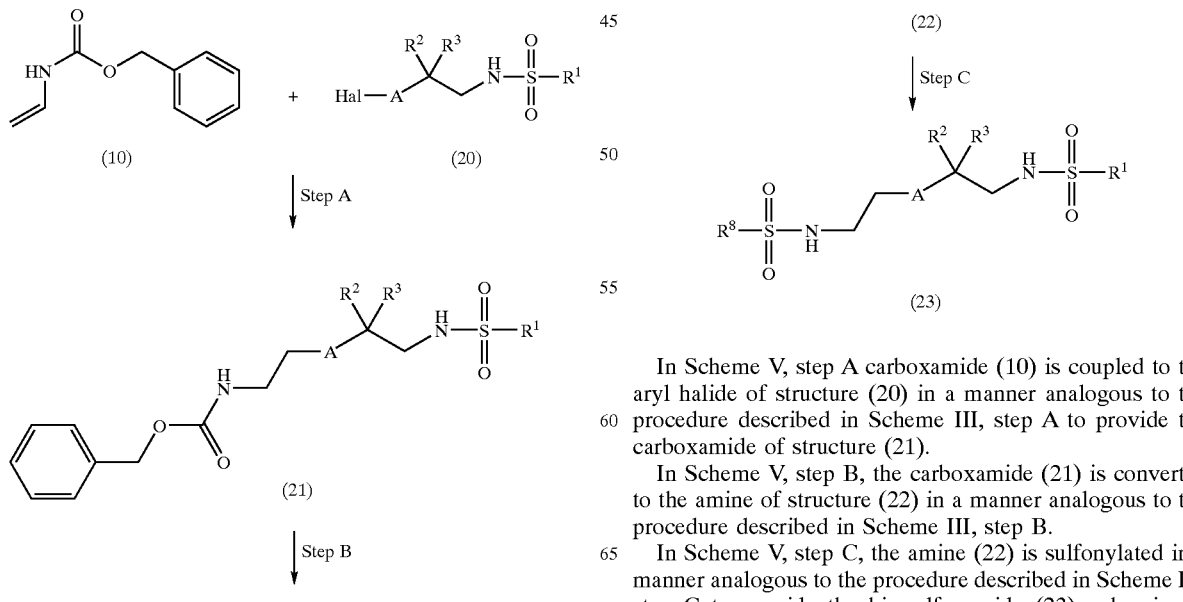

In Scheme V, step A carboxamide (10) is coupled to the aryl halide of structure (20) in a manner analogous to the procedure described in Scheme III, step A to provide the carboxamide of structure (21).

In Scheme V, step B, the carboxamide (21) is converted to the amine of structure (22) in a manner analogous to the procedure described in Scheme III, step B.

In Scheme V, step C, the amine (22) is sulfonylated in a manner analogous to the procedure described in Scheme III, step C to provide the bis-sulfonamide (23), wherein $R^1$ represents (1–6C)alkyl, (2–4C)alkenyl, or $NR^9R^{10}$, and R8 represents (1–6C)alkyl, unsubstituted or substituted aryl, unsubstituted or substituted heteroaromatic group, cycloalkyl, or alkylcycloalkyl.

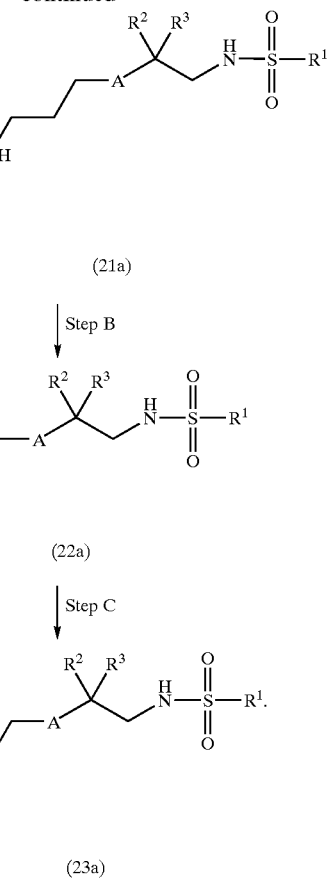

The compounds prepared in Scheme Va are prepared by one of ordinary skill in the art in a manner analogous to the procedures set forth in Scheme V above.

In Scheme Va, step A carboxamide (10a) is coupled to the aryl halide of structure (20) in a manner analogous to the procedure described in Scheme III, step A to provide the carboxamide of structure (21a).

In Scheme Va, step B, the carboxamide (21a) is converted to the amine of structure (22a) in a manner analogous to the procedure described in Scheme III, step B.

In Scheme Va, step C, the amine (22a) is sulfonylated in a manner analogous to the procedure described in Scheme III, step C to provide the bis-sulfonamide (23a), wherein $R^1$ represents (1–6C)alkyl, (2–6C)alkenyl, or $NR^9R^{10}$, and $R^8$ represents (1–6C)alkyl, unsubstituted or substituted aryl, unsubstituted or substituted heteroaromatic group, cycloalkyl, or alkylcycloalkyl.

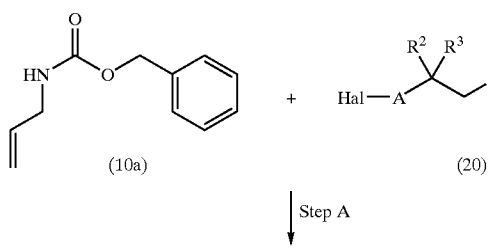

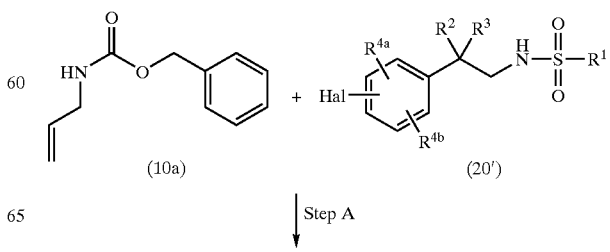

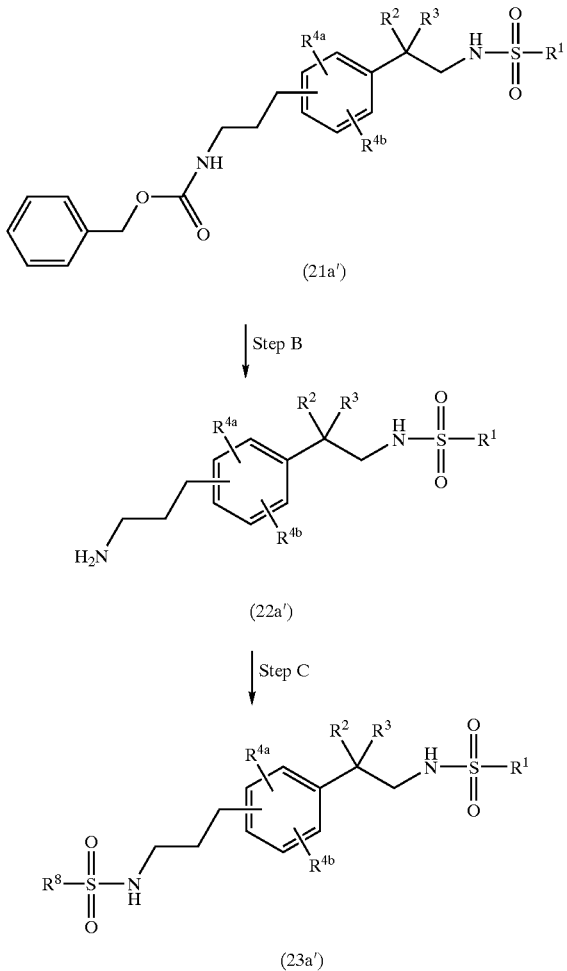

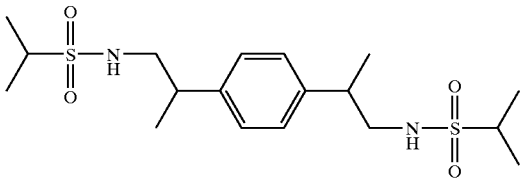

The compounds prepared in Scheme IVc are prepared by one of ordinary skill in the art in a manner analogous to the procedures set forth in Scheme IVb above.

The following examples further illustrate the invention and represent typical syntheses of the compounds of formula I as described generally above. The reagents and starting materials are readily available to one of ordinary skill in the art. As used herein, the following terms have the meanings indicated: "eq" refers to equivalents; "g" refers to grams; "mg" refers to milligrams; "kPa" refers to kilopascals; "L" refers to liters; "mL" refers to milliliters; "μL" refers to microliters; "mol" refers to moles; "mmol" refers to millimoles; "psi" refers to pounds per square inch; "min" refers to minutes; "h" or "hr" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ" refers to part per million down-field from tetramethylsilane; "THF" refers to tetrahydrofuran; "DMF" refers to N,N-dimethylformamide; "DMSO" refers to methyl sulfoxide; "LDA" refers to lithium diisopropylamide; "EtOAc" refers to ethyl acetate; "aq" refers to aqueous; "iPrOAc" refers to isopropyl acetate; "PdCl$_2$(dppf)" refers to [1,1'bis(diphenylphosphino)-ferrocene] dichloropalladium (II); "methyl DAST" refers to dimethylaminosulfur trifluoride, "DAST" refers to diethylaminosulfur trifluoride, "DBU" refers to 1,8-diazabicyclo[5.4.0]undec-7-ene; "TFA" refers to trifluoroacetic acid; "DME" refers to dimethoxyethane;

"9-BBN dimer" refers 9-borabicyclo[3.3.1]nonane dimer; and "RT" refers to room temperature.

EXAMPLE 1

Preparation of [(Methylethyl)sulfonyl]{2-[4-(1-methyl-2-{[(methylethyl)sulfonyl]amino}ethyl)phenyl]propyl}amine

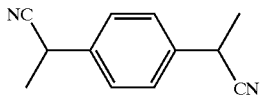

Preparation of 2-[4-(Cyano-methyl-methyl)-phenyl]-propionitrile

Scheme I, step A: The intermediate title compound is prepared in a manner analogous to the procedure of Brenner, *Tetahedron*, 52, 487–491 (1976). For example, a dry 100 mL round bottom flask equipped with a magnetic stirrer was charged with a 1M THF solution of methyl lithium (52 mL, 52 mmol) under nitrogen. The flask was cooled to −75° C. and anhydrous ether (50 mL) was added. 1,4-phenylenediacetonltrile (4.0 g, 25.6 mmol) was dissolved in anhydrous THF (20 mL) and added dropwise. After the addition was complete the reaction was allowed to slowly warm to room temperature and stirred for 2 h. The reaction was re-cooled to −75° C. and methyl iodide (3.2 mL, 51.2 mmol) added dropwise. The solution was then brought to −45° C. for 5 minutes. The reaction was quenched with cold water and diluted with ether. The organics were washed with 0.1 N HCl, H$_2$O, dried over MgSO$_4$, and filtered. The filtrate was concentrated to provide 11.2 g of a thick, orange oil. This oil was purified by radial chromatography (Chromatotron, Harrison Research Inc., Palo Alto, Calif. 94306) eluting with 30:70 Ethyl Acetate:Hexanes. The fractions were concentrated to provide the intermediate title compound (3.25 g, 69%) as a mixture of desired products with minor amounts of over-methylation present. This material was used in the following step without further purification. Mass Spectrum (ES MS): M*−H=183.

Preparation of 2-[4-(2-Amino-1-methyl-ethyl)-phenyl]-propylamine Dihydrochloride

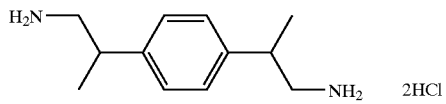

Scheme I, step B: 2-[4-(Cyano-methyl-methyl)-phenyl]-propionitrile (3.25 g, 17.7 mmol) was dissolved in anhydrous THF (30 mL). The solution was heated to reflux and a 2M THF solution of borane-methyl sulfide complex (19.5 mL, 38.9 mmol) was added dropwise. Heating at reflux was continued for 30 minutes and then allowed to cool to room temperature. An HCl saturated solution of methanol (30 mL) was slowly added until pH=2. The mixture was concentrated in vacuo, redissolved in methanol and concentrated again to provide the intermediate title compound (4.5 g, 96%). TLC and HPLC indicated the starting material had been consumed and produced a mixture of more polar products. This material was used crude in the next step without further characterization.

Preparation of Final Title Compound

Scheme I, step C: 2-[4-(2-Amino-1-methyl-ethyl) phenyl]-propylamine dihydrochloride (1.4 g, 5.28 mmol) was dissolved in methylene chloride (40 mL) and treated with triethylamine (4.5 mL, 31.7mmol) at room temperature. Isopropylsulfonyl chloride (1.3 mL, 11.6 mmol) was then added and stirring continued overnight under nitrogen. TLC suggested a poor conversion, so DBU (1.0 mL) followed by an additional amount of isopropylsulfonyl chloride (1.0 mL) was added and stirring continued overnight at room temperature. The reaction was then diluted with methylene chloride and washed with 1N HCl. The organic layer was dried over sodium sulfate, filtered, and concentrated in vacuo to provide a crude orange oil. This oil was passed through a 2 g silica cartridge eluding with 90:10 EtOAc:methylene chloride to give 1.5 g of an orange oil. This material was further purified by radial chromatography (Chromatotron) eluting with methylene chloride with a gradient to 10% methanol. The appropriate fractions were concentrated to provide 240 mg of a yellow oil. The analytical HPLC (VYDAC C18, detection at 214 nm, flow 1.0 mL/min, gradient of acetonitrge 5–70% over 45 min with aqueous 0.1% TFA buffer) shows a major peak A at 29.4 min (57%), and minor peak B at 30.2 min (15%) and peak C at 31.1 min (14%). A preparative purification by reverse phase HPLC was done on a Vydac C18 column (5.0×25 cm) eluting with a gradient of 5–40% ACN and 0.01% HCl buffer over 3 h, monitoring at 214 nm, with a flow rate of 20 mL/min to provide the final title compound, [(methylethyl) sulfonyl]{2-[4-(1-methyl-2-{[(methylethyl)sulfonyl] amino}ethyl)phenyl]propyl}amine, (75 mg, peak A). Mass Spectrum (ES MS): M*–H=403. Analysis calculated for $C_{18}H_{32}N_2O_4S_2$: Theory: %C, 53.44; %H, 7.97; %N, 6.92. Found: %C, 53.02; %H, 7.77; %N, 6.81.

In addition, a diastereomer (19 mg, peak B) of the title compound was isolated; Mass Spectrum (ES MS): M–1=403. Exact Mass calculated for (M+H) $C_{18}H_{32}N_2O_4S_2$= 405.1882; found 405.1898

Propane-2-sulfonic acid (2-methyl-2-{4-[1-methyl-2-(propane-2-sulfonylamino)-ethyl]-pheny}-propyl) amide (18 mg, peak C),

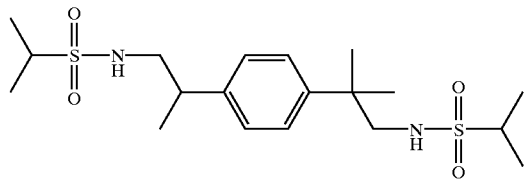

an over-methylation byproduct, was also isolated. Mass Spectrum (ES MS): M*–H=417. Exact Mass calculated for (M+H) $C_{19}H_{34}N_2O_4S_2$=419.2038; found 419.2029.

EXAMPLE 2

Preparation of [(Methylethyl)sulfonyl]{2-[4-(2-{[(methylethyl)sulfonyl]amino}ethyl)phenyl] ethyl}amine

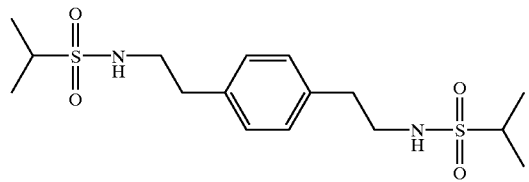

Preparation of 2-[4-(2-Aminoethyl)phenyl] ethylamine

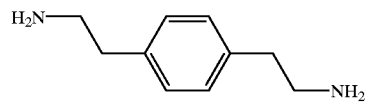

Scheme I, step B': Into a 250 mL reduction vessel were placed 1,4-phenylenediacetonitrile (10 g, 64.02 mmol), liquid ammonia (25 mL), and W4–W6 range (medium range activity) Raney Nickel (1.25 g) in methanol (125 mL), and the mixture was heated at 100° C. under 300 psi (2068 kPa) of hydrogen gas for 10 hours. The reaction was cooled to room temperature and filtered through a Celite® cake and the filtrate was concentrated under reduced vacuum to give the intermediate title compound, 2-[4-(2-aminoethyl) phenyl]ethylamine, (10.3 g, 98%) as an oil. Electron spray M.S. 165 (M*+H).

Preparation of Final Title Compound

Scheme I, step C': Into a 50 mL single neck flask were placed 2-[4-(2-aminoethyl)phenyl]ethylamine (2 g, 12.2 mmol), 1,8-diazabicyclo [5.4.0] undec-7-ene, DBU, (9 mL, 60.5 mmol), and isopropylsulfonyl chloride (2.9 mL, 25.6 mmol), in THF:methylene chloride (15:15 mL) at 0° C. The mixture was warmed up to room temperature while stirring for ½ hour. The reaction mixture was quenched with 0.2 M HCl until pH was below 45. The product was extracted with EtOAc and the organic layer was separated and washed twice with $H_2O$, dried over anhydrous $Na_2SO_4$, filtered, and concentrated under reduced vacuum. The resulting semi-solid was purified via flash chromatography (Silica gel, isocratic) and eluting with a solvent of Hexanes/EtOAc 50% to provide the title compound, [(methylethyl)sulfonyl]{2-[4-(2-{[(methylethyl)sulfonyl]amino}ethyl)phenyl] ethyl}amine, (0.5 g, 11%) as a white crystalline solid. Electron spray M.S. 375 (M*–H). Analysis for $C_{16}H_{28}N_2O_4S_2$:

| Theory: | C, 51.04 | H, 7.50 | N, 7.44 |
| Found: | C, 51.15 | H, 7.59 | N, 7.38 |

EXAMPLE 2-1

Preparation of [(Methylethyl)sulfonyl]{[4-({[(methylethyl)sulfonyl]amino}methyl)phenyl]methyl}amine

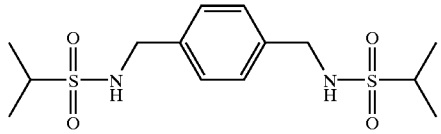

Scheme 1, step C': 1,4-xylenediamine (1.4 g, 10.28 mmol), DBU (3.4 mL, 22.6 mmol), and isopropylsulfonyl chloride (2.4 mL, 21.6 mmol), in THF:methylene chloride (15:15 mL) at 0° C. were combined in a manner analogous to the procedure described in example 2 to provide the final title compound, [(methylethyl)sulfonyl]{[4-({[(methylethyl)sulfonyl]amino}methyl)phenyl]methyl}amine, (1.22 g, 34%) as a white crystalline solid. Electron spray M.S. 349 (M*+H).

Analysis for $C_{14}H_{24}N_2O_4S_2$:

| Theory: | C, 48.25 | H, 6.94 | N, 8.04 |
| --- | --- | --- | --- |
| Found: | C, 47.85 | H, 6.79 | N, 8.13 |

EXAMPLE 3

Preparation of {2-[4-(1,1-Dimethyl-2-{[(methylethyl)sulfonyl]amino}ethyl)phenyl]-2-methylpropyl}[(methylethyl)sulfonyl]amine

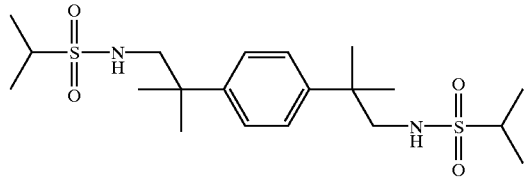

Preparation of 2-[4-(1-Cyano-isopropyl)phenyl]-2-methylpropanenitrile

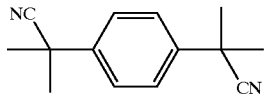

Scheme I, step A: Into a 250 mL single neck flask was placed sodium hydride 60% (5.4 g, 134.5 mmol) in DMF (100 mL) at −15° C. 1,4-Phenyldiacetonitrile (5 g, 32 mmol) was added to the solution slowly and the mixture was stirred for ½ hour. The reaction mixture was treated with methyl iodide (8.4 mL, 134.5 mmol). The mixture was warmed up to RT while stirring for 12 hours. The reaction mixture was poured into ice water (600 mL) until product was precipitated out. The precipitate was filtered off and washed with cold water to provide the intermediate tide compound, 2-[4-(1-cyano-isopropyl)phenyl]-2-methylpropanenitrile, (6.8 g, 100%) as a white solid. Electron spray M.S. 230 (M*+$H_2O$).

Preparation of 2-[4-(2-Amino-tert-butyl)phenyl]-2-methylpropylamine Dihydrochloride

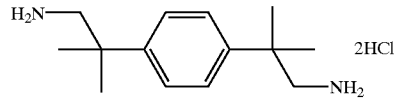

Scheme I, step B: Into a 100 mL single neck flask was placed 2-[4-(1-cyano-isopropyl)phenyl]-2-methylpropanenitrile (5.5 g, 25.91 mmol) in THF (25 mL). Boron dimethylsulfide 10 M in THF (6.5 mL, 64.7 mmol) was added to the solution and the mixture was heated to reflux for 45 minutes. The reaction mixture was cooled down to room temperature and quenched with saturated solution of HCl in methanol (15 mL). Diethyl ether (50 mL) was added to the mixture and it was cooled down to 0° C. The product was precipitated out of the solution as dihydrochlorde salt. The salt was filtered and dried in vacuum to provide the intermediate title compound, 2-[4-(2-amino-tert-butyl)phenyl]-2-methylpropylamine, (7.6 g, 100%) as a white solid crystal. Electron spray M.S. 220 (M*−2HCl).

Preparation of Final Title Compound

Scheme I, step C: Into a 100 mL single neck flask was placed 2-[4-(2-amino-tert-butyl)phenyl]-2-methylpropylamine (2 g, 6.82 mmol) in THF:methylene chloride (25:25 mL) and the solution was cooled down to 0° C. 1,8-diazabicyclo [5.4.0] undec-7-ene, DBU, (5.1 mL, 34.1 mmol) was added to the mixture and after 15 minutes isopropylsulfonyl chloride (1.7 mL, 15 mmol) was added to the reaction mixture. The mixture was warmed up to RT while stirring for 12 hour. The reaction mixture was quenched with a 0.1 M HCl until pH was below 4–5. The product was extracted with EtOAc and the organic layer was separated and washed twice with water, dried over anhydrous $Na_2SO_4$, filtered, and concentrated under reduced vacuum. The resulting semi-solid was purified via flash chromatography (Silica gel, isocratic) and eluting with a solvent of Hexanes/EtOAc 40% to provide the final title compound, {2-[4-(1,1-dimethyl-2-{[(methylethyl)sulfonyl]amino}ethyl)phenyl]-2-methylpropyl}[(methylethyl)sulfonyl]amine, (870 mg, 30%) as a white crystalline solid. Electron pray M.S. 431 (M*−H). Analysis for $C_{20}H_{36}N_2O_4S_2$:

| Theory: | C, 55.52 | H, 8.39 | N, 6.47 |
| --- | --- | --- | --- |
| Found: | C, 55.57 | H, 8.35 | N, 6.44 |

EXAMPLE 4

Preparation of {2-Hydroxy-2-[4-(1-hydroxy-1-methyl-2-{[(methylethyl)sulfonyl]amino}ethyl)phenyl]propyl}[(methylethyl)sulfonyl]amine

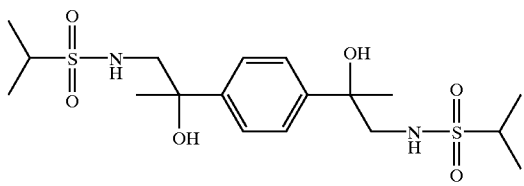

Preparation of 2-(1,1-Dimethyl-1-silaethoxy)-2-{4-[1-(1,1-dimethyl-1-silaethoxy)-1-cyanoethyl]phenyl}propanenitrile

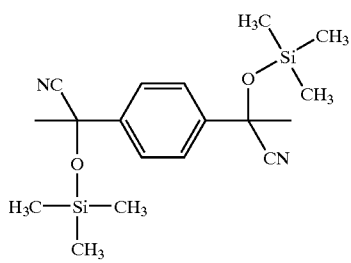

Scheme II, step A: Into a 100 mL single neck flask were placed 1,4-diacetylbenzene (4 g, 24.66 mmol), trimethylsilyl cyanide (9.9 mL, 74.25 mmol), and catalytic amount of zinc iodide (0.4 g, 1.25 mmol). The mixture was stirred at RT for 2 hours. The reaction mixture was poured into 10% sodium bicarbonate solution (100 mL). The product was extracted with EtOAc and the organic layer was separated and washed twice with water, dried over anhydrous $Na_2SO_4$, filtered, and concentrated under reduced vacuum. The resulting oil was further purified via flash chromatography (Silica gel, isocratic) and eluting with a solvent of Hexanes/EtOAc 10% to provide the intermediate title compound, 2-(1,1-dimethyl-1-silaethoxy)-2-{4-[1-(1,1-dimethyl-1-silaethoxy)-1-cyanoethyl]phenyl}propanenitrile, (7.8 g, 88%) as colorless oil.

Ion spray M.S. 334 (M*–CN).

Preparation of 1-Amino-2-[4-(2-amino-1-hydroxy-isopropyl)phenyl]propan-2-ol Dihydrochloride

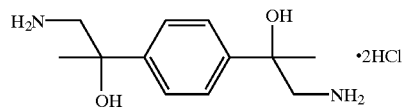

Scheme II, step B: 2-(1,1-Dimethyl-1-silaethoxy)-2-{4-[1-(1,1-dimethyl-1-silaethoxy)-1-cyanoethyl]phenyl}propanenitrile (7.8 g, 21.63 mmol) in THF (50 mL) is treated with Boron dimethylsulfide 10 M in THF (5.4 mL, 54.1 mmol) in a manner analogous to the procedure described in example 3 to provide the intermediate title compound, 1-amino-2-[4-(2-amino-1-hydroxy-isopropyl)phenyl]propan-2-ol dihydrochloride, (6.42 g, 100%) as a white crystalline solid. Electron spray M.S. 225(M*+H)

Preparation of Final Title Compound

Scheme II, step C: Into a 100 mL single neck flask was placed 1-amino-2-[4-(2-amino-1-hydroxy-isopropyl)phenyl]propan-2-ol (3 g, 10.1 mmol) in THF:methylene chloride (20:20 mL) and the solution was cooled down to 0° C. 1,8-Diazabicyclo [5.4.0] undec-7-ene, DBU, (7.6 mL, 50.5 mmol) was added to the mixture and after 15 minutes isopropylsulfonyl chloride (2.54 mL, 22.2 mmol) was subsequently added to the reaction mixture. The mixture was warmed up to RT while stirring for 12 hour. The reaction mixture was quenched with a 0.1 M HCl until pH was below 45. The product was extracted with EtOAc and the organic layer was separated and washed twice with $H_2O$, dried over anhydrous $Na_2SO_4$, filtered, and concentrated under reduced vacuum. The resulting semi-solid was dissolved in chloroform (20 mL) and cooled down in freezer to provide the final title compound, {2-hydroxy-2-[4-(1-hydroxy-1-methyl-2-{[(methylethyl)sulfonyl]amino}ethyl)phenyl]propyl}[(methylethyl)sulfonyl]amine, (566 mg, 30%) as a white solid. Electron pray M.S. 435 (M*–H). Analysis for $C_{18}H_{32}N_2O_6S_2$:

| Theory: | C, 49.52 | H, 7.39 | N, 6.42 |
| Found: | C, 47.60 | H, 6.99 | N, 5.90 |

EXAMPLE 5

Preparation of {2-Fluoro-2-[4-(1-fluoro-1-methyl-2-{[(methylethyl)sulfonyl]amino}ethyl)phenyl]propyl}[(methylethyl)sulfonyl]amine

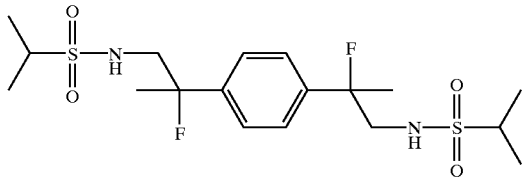

Scheme II, step D: Into a 10 mL single neck flask was placed {2-hydroxy-2-[4-(1-hydroxy-1-methyl-2-{[(methylethyl)sulfonyl]amino}ethyl)phenyl]propyl}[(methylethyl)sulfonyl]amine (300 mg, 0.69 mmol) in THF (5 mL) and the mixture was cooled down to –78° C. DAST (0.2 mL, 2.2 mmol) was added to the reaction dropwise and the reaction mixture was warmed up gradually to RT while stirring for 12 h. The reaction mixture was quenched with $H_2O$ (10 mL). The product was extracted with methylene chloride and the organic layer was separated and washed twice with $H_2O$, dried over anhydrous $Na_2SO_4$, filtered, and concentrated under reduced vacuum. The resulting semi-solid was further purified via flash chromatography (Silica gel, isocratic) and eluting with a solvent of Hexanes/EtOAc 50% to provide the title compound (185 mg 61%) as a white solid. Electron spray M.S. 439 (M*–1). Analysis for $C_{18}H_{30}F_2N_2O_4S_2$:

| Theory: | C, 49.07 | H, 6.86 | N, 6.36 |
| Found: | C, 48.86 | H, 6.86 | N, 6.31 |

EXAMPLE 6

Preparation of [(2-Fluoro-4-{2-[(methylsulfonyl)amino]ethyl}phenyl)methyl](methylsulfonyl)amine

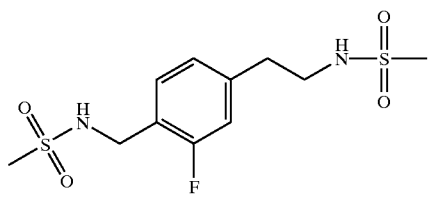

Preparation of 1-Aza-1-diazobuta-1,3-dien-2-one

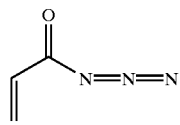

The intermediate title compound, 1-aza-1-diazobuta-1,3-dien-2-one and (phenylmethoxy)N-vinylcarboxamide (prepared in the next step) can be prepared in a manner analogous to the procedure described by D. J. am Ende, et al., "A Calorimetric Investigation to Safely Scale-up a Curtius Rearrangement of Acryloyl Azide," *Organic Process Research & Development*, 2, 382–392 (1998). For example, into a 500 mL single neck flask was placed sodium azide (48.12 g, 740 mmol) in H$_2$O (150 mL) and the mixture was cooled down to 0° C. A mixture of acryloyl chloride (50 mL, 615 mmol) in toluene (200 mL) was added dropwise to the aqueous mixture and the reaction was warmed up to RT while stirring for 18 hours. The organic layer was separated and washed with 10% aqueous sodium bicarbonate (100 mL), water (10×100 mL) until the last aqueous layer failed to give a precipitate upon addition of the dilute solution of the silver nitrate. The combined organic layer dried over anhydrous Na$_2$SO$_4$ and filtered before use in the subsequent step.

Preparation of (Phenydmethoxy)-N-vinylcarboxamide

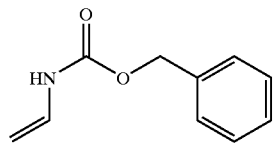

Into a 500 mL single neck flask were placed benzyl alcohol (76.5 mL, 792 mmol), hydroquinone (3.05 g, 27.7 mmol), pyridine (3 mL, 27.7 mmol) and the mixture was stirred at 100° C. while treated with the toluene solution of 1-aza-1-diazobuta-1,3-dien-2-one (200 mL) dropwise. The mixture was stirred at 110° C. for 30 minutes and at RT for 12 hours. The reaction mixture was concentrated and the resulting crude oil was distilled under reduced pressure (0.4 mm Hg) to provide the intermediate title compound, (phenylmethoxy)-N-vinylcarboxamide, (43.1 g, 45%) as a pure oil (came out at 110–115° C.) which solidified upon sitting at RT. Electron spray M.S. 178 (M*+H) Analysis for C$_{10}$H$_{11}$NO$_2$:

| Theory: | C, 67.78 | H, 6.26 | N, 7.90 |
|---|---|---|---|
| Found: | C, 67.85 | H, 6.30 | N, 7.71 |

Preparation of N-[2-(4-Cyano-3-fluorophenyl)ethyl](phenylmethoxy)carboxamide

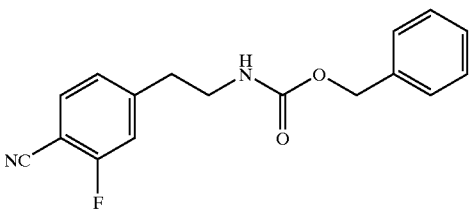

Scheme III, step A: Into a 100 mL single neck flask was placed (phenylmethoxy)-N-vinylcarboxamide (5.54 g, 31.25 mmol) in THF (15 mL). The mixture was cooled down to −10° C. while treated dropwise with a solution of 9-BBN dimer (3.81 g, 15.62 mmol) in THF (20 mL). The reaction mixture was warmed up to RT while stirring for additional 2 hours. The reaction mixture was quenched with 3N NaOH (2mL) and the mixture was stirred for 10 minutes before its addition to a solution of 4-bromo-2-fluorobenzonitrile (5 g, 25 mmol) and [1,1'bis(diphenylphosphino)-ferrocene] dichloropalladium (II), PdCl$_2$(dppf), (0.4 g, 0.5 mmol) in THF (10 mL). The mixture was stirred at RT for 12 hour and then was quenched with a 2:1 mixture of pH=7 buffer hydrogen peroxide (10 mL). The product was extracted with EtOAc and the organic layer was separated and washed twice with H$_2$O, dried over anhydrous Na$_2$SO$_4$, filtered, and concentrated under reduced vacuum. The resulting semi-solid was further purified via flash chromatography (Silica gel, isocratic) and eluting with a solvent of Hexanes/EtOAc 50% to provide the intermediate title compound, N-[2-(4-cyano-3-fluorophenyl)ethyl](phenylmethoxy)carboxamide, (6.4 g, 86%) as a white solid. Electron spray M.S. 299 (M*+H).

Preparation of 4-(2-Aminoethyl)-2-fluorobenzenecarbonitrile

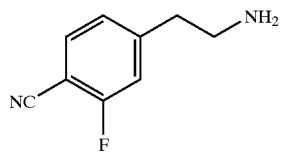

Scheme III, step B: Into a 100 mL single neck flask were placed N-[2-(4-cyano-3-fluorophenyl)ethyl](phenylmethoxy)carboxamide (2 g, 6.7 mmol) in THF: MeOH (25:25 mL). The mixture was treated with a 10% palladium on carbon (0.5 g, 25 mol%) and stirred under the hydrogen balloon for 12 hour. The reaction mixture was filtered through a Celite® cake. The filtrate was concentrated under reduced vacuum to provide the intermediate title compound, 4-(2-aminoethyl)-2-fluorobenzenecarbonitrile, (1.1 g, 100%) as a white solid. Electron spray M.S. 165 (M*+1).

Preparation of 2-[4-(Aminomethyl)-3-fluorophenyl] ethylamine Dihydrochloride

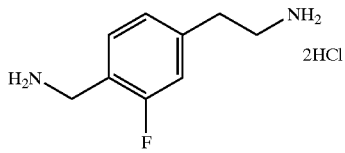

Scheme III, step C: Into a 100 mL single neck flask was placed 4-(2-aminoethyl)-2-fluorobenzenecarbonitrile (1.05 g, 6.39 mmol) in THF (25 mL). Boron dimethylsulfide 2 M in THF (6.4 mL, 12.8 mmol) was added to the solution and the mixture was heated to reflux for 18 hour. The reaction mixture was cooled down to RT and quenched with saturated solution of HCl in methanol (20 mL). Diethyl ether (75 mL) was added to the mixture and it was cooled down to 0° C. The product was precipitated out of the solution as dihydrochloride salt. The salt was filtered and dried in vacuum to provide the title compound, 2-[4-(aminomethyl)-3-fluorophenyl]ethylamine, (1.36 g, 88%) as a white crystalline solid. Electron spray M.S. 169 (M*−2HCl).

Preparation of Final Title Compound

Scheme III, step D: 2-[4-(Aminomethyl)-3-fluorophenyl] ethylamine (0.3 g, 1.25 mmol) was combined with methanesulfonyl chloride (0.2 mL, 2.75 mmol), and DBU (1 mL, 3.12 mmol) in a manner analogous to the procedure described in example 2 to provide the final title compound, [(2-fluoro-4-{2-[(methylsulfonyl)amino]ethyl}phenyl) methyl](methylsulfonyl)amine, (0.15 g, 37%) as a white crystalline solid. Electron spray M.S. 323 (M*−H). Analysis for $C_{11}H_{17}FN_2O_4S_2$:

| Theory: | C, 40.73 | H, 5.28 | N, 8.64 |
| --- | --- | --- | --- |
| Found: | C, 40.90 | H, 5.15 | N, 8.44 |

EXAMPLE 7

Preparation of {2-[3-Fluoro-4-({[(methylethyl) sulfonyl]amino}methyl)phenyl]ethyl}[(methylethyl) sulfonyl]amine

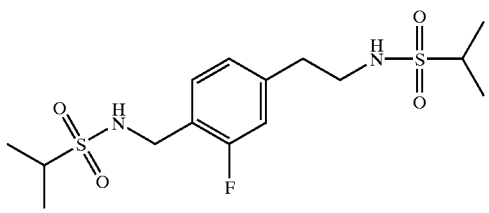

Scheme III, step D: 2-[4-(Aminomethyl)-3-fluorophenyl] ethylamine (0.3 g, 1.25 mmol) was combined with isopropylsulfonyl chloride (0.31 mL, 2.75 mmol), and DBU (1 mL, 3.12 mmol) in a manner analogous to the procedure described in example 2 to provide the title compound (0.15 g, 31%) as a white crystalline solid. Electron spray M.S. 379 (M*−H). Analysis for $C_{15}H_{25}FN_2O_4S_2$:

| Theory: | C, 47.35 | H, 6.62 | N, 7.36 |
| --- | --- | --- | --- |
| Found: | C, 47.44 | H, 6.41 | N, 7.30 |

EXAMPLE 8

Preparation of {[2-Fluoro-4-(3-{[(methylethyl) sulfonyl]amino}propyl)phenyl]methyl} [(methylethyl)sulfonyl]amine

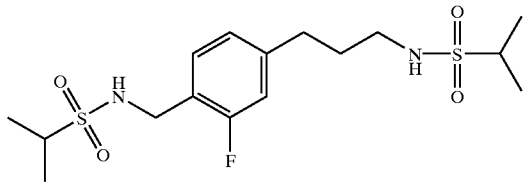

Preparation of (Phenylmethoxy)-N-prop-2-enylcarboxamide

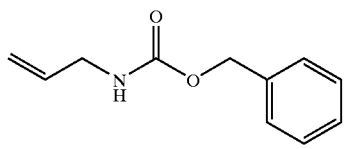

Into a 250 mL single neck flask were placed allylamine (5 mL, 66.6 mmol) and triethylamine (11.1 mL, 80 mmol) in methylene chloride (80 mL). The mixture was cooled to −5° C. before being treated with benzylchloroformate (10 mL, 70 mmol) gradually. The reaction mixture was warmed up to RT while stirring overnight. The product was extracted with EtOAc and the organic layer was separated and washed twice with $H_2O$, dried over anhydrous $Na_2SO_4$, filtered, and concentrated under reduced vacuum. The resulting oil was further purified via flash chromatography (Silica gel, isocratic) and eluting with a solvent of Hexanes/EtOAc 20% to provide the intermediate title compound, (phenylmethoxy)-N-prop-2-enylcarboxamide, (8.7 g, 68%) as oil. Electron spray M.S. 192 (M*+1).

Preparation of N-[3(4-Cyano-3-fluorophenyl) propyl](phenylmethoxy)carboxamide

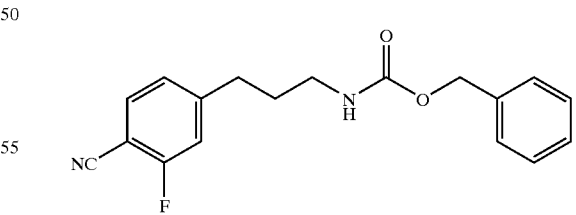

Scheme IIIb, step A: 4-Bromo-2-fluorobenzonitrile (3 g, 15 mmol), (phenylmethoxy)-N-prop-2-enylcarboxamide (3.44 g, 18 mmol), 9-BBN dimer (2.93 g, 12 mmol), [1,1'bis(diphenylphosphino)ferrocene] dichloropalladium (II), $PdCl_2$(dppf) (0.61 g, 0.75 mmol), 3N sodium hydroxide (10 mL), and pH=7 buffer: hydrogen peroxide (2:1, 20 mL) are combined in a manner analogous to the procedure described in example 6 to provide the intermediate title compound, N-[3-(4-cyano-3-fluorophenyl)propyl](phenylmethoxy)carboxamide, (4.18, 89%). Electron spray M.S. 313 (M*+H).

Preparation of 4-(3-Aminopropyl)-2-fluorobenzenecarbonitrile

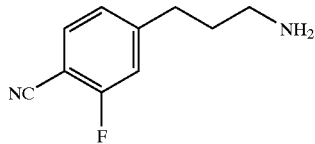

Scheme IIIb, step B: N-[3-(4-Cyano-3-fluorophenyl)propyl](phenylmethoxy)carboxamide (2 g, 6.4 mmol) and 10% palladium on carbon (0.5 g, 25 mole %) combined and hydrogenation was carried out in a manner analogous to the procedure described in example 6 to provide the intermediate title compound, 4-(3-aminopropyl)2-fluorobenzenecarbonitrile, (1.1 g, 96%) as a colorless oil. Electron spray M.S. 179 (M*+H).

Preparation of 3-[4-(Aminomethyl)-3-fluorophenyl]propylamine Dihydrochloride

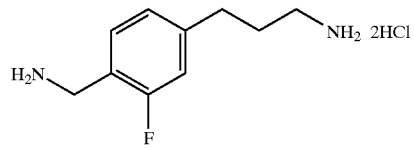

Scheme IIIb, step C: 4-(3-Aminopropyl)-2-fluorobenzenecarbonitrile (1.1 g, 6.17 mmol) and boron dimethylsulfide 2M in THF (6.2 mL, 12.34 mmol) were combined and reduction was carried out in a manner analogous to the procedure described in example 6 to provide the intermediate title compound, 3-[4-(aminomethyl)-3-fluorophenyl]propylamine dihydrochlorde, (1.15 g, 73%) as a dihydrochloride salt. Electron spray M.S. 183 (M*+H).

Preparation of Final Title Compound

Scheme IIIb, step D: 3-[4-(Aminomethyl)-3-fluorophenyl]propylamine (0.3 g, 1.18 mmol), isopropylsulfonyl chloride (0.3 mL, 2.59 mmol), and DBU (0.9 mL, 2.94 mmol) were combined and sulfonylation was carried out in a manner analogous to the procedure described in example 2 to provide the final title compound, {[2-fluoro-4-(3-{[(methylethyl)sulfonyl]amino}propyl)phenyl]methyl}[(methylethyl)sulfonyl]amine, (0.195 g, 42%) as a white crystalline solid. Electron spray M.S. 393 (M*−H). Analysis for $C_{16}H_{27}FN_2O_4S_2$:

| | | | |
|---|---|---|---|
| Theory: | C, 48.71 | H, 6.90 | N, 7.10 |
| Found: | C, 48.84 | H, 6.85 | N, 7.06 |

EXAMPLE 9

Preparation of [(Methylethyl)sulfonyl]{3-[4-(3-{[(methylethyl)sulfonyl]amino}propyl)phenyl]propyl}amine

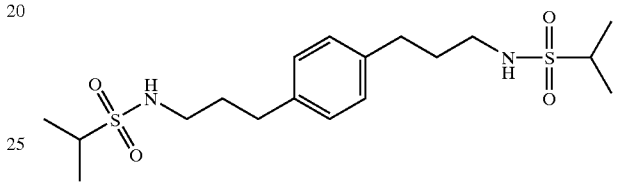

Preparation of (Phenylmethoxy)-N-[3-(4-{3-[(phenylmethoxy)carbonylamino]propyl}phenyl)propyl]carboxamide

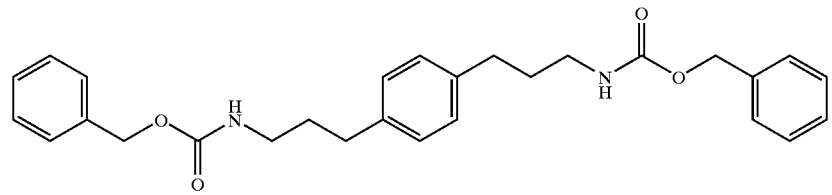

Scheme IVc, step A: 1,4-Dibromobenzene (2 g, 8.5 mmol), (phenylmethoxy)-N-prop-2-enylcarboxamide (4.1 g, 21.2 mmol, prepared in example 8), 9-BBN dimer (3.2 g, 13 mmol), [1,1'bis(diphenylphosphino)-ferrocene] dichloropalladium (II), $PdCl_2$(dppf), (0.3 g, 0.37 mmol), 3N sodium hydroxide (3 mL), and pH 7 buffer: hydrogen peroxide (2:1, 15 mL) were combined in a manner analogous to the procedure described in example 6 to provide the intermediate title compound, (phenylmethoxy)-N-[3(4-{3-[(phenylmethoxy)carbonylamino]propyl}phenyl)propyl]carboxamide, (3.1 g, 79%). Electron spray M.S. 461 (M*+H).

Preparation of 3-[4-(3-Aminopropyl)phenyl]propylamine Dihydrochloride

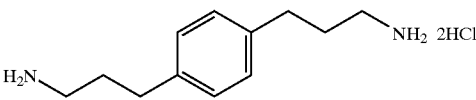

Scheme IVc, step B: (Phenylmethoxy)N-[3-(4-{3-[(phenylmethoxy)carbonylamino]propyl}phenyl)propyl]

carboxamide (2 g, 4.34 mmol) and 10% palladium on carbon (0.5 g, 25 mole %) were combined and hydrogenation was carried out in a manner analogous to the procedure described in example 6 to provide the intermediate title compound, 3-[4-(3-aminopropyl)phenyl]propylamine dihydrochloride, (0.3 g, 36%) as a colorless oil. Electron spray M.S. 191 (M+–H).

Preparation of Final Title Compound

Scheme IVc, step C: 3-[4-(3-aminopropyl)phenyl] propylamine (0.3 g, 1.56 mmol), isopropylsulfonyl chloride (0.4 mL, 3.43 mmol) and DBU (0.54 mL, 3.6 mmol) were combined and sulfonylation was carried out in a manner analogous to the procedure described in example 2 to provide the final title compound, [(methylethyl)sulfonyl]{3-[4-(3-{[(methylethyl)sulfonyl]amino}propyl)phenyl] propyl}amine, (0.18 g, 29%) as a white crystalline solid. Electron spray M.S. 405 (M*+H). Analysis for $C_{18}H_{32}N_2O_4S_2$:

| Theory: | C, 53.44 | H, 7.97 | N, 6.93 |
| --- | --- | --- | --- |
| Found: | C, 53.41 | H, 7.60 | N, 7.32 |

EXAMPLE 9-1

Preparation of [(Methylethyl)sulfonyl]{2-[4-(3-{[(methylethyl)sulfonyl]amino}propyl)phenyl] ethyl}amine

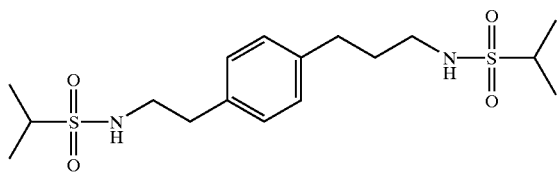

Preparation of N-[3-(4-Bromophenyl)propyl] (phenylmethoxy)carboxamide

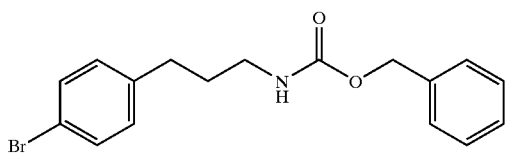

Scheme IVc, step A: 1,4-Dibromobenzene (2 g, 8.5 mmol), (phenylmethoxy)-N-prop-2-enylcarboxamide (1.95 g, 10.1 mmol, prepared in example 8), 9-BBN-dimer (2.7 g, 11 mmol), [1,1'bis(diphenylphosphino)-ferrocene] dichloropalladium (II), PdCl$_2$(dppf), (0.35 g, 0.42 mmol), 3N sodium hydroxide (3 mL), and pH=7 buffer hydrogen peroxide (2:1, 10 mL) were combined in a manner analogous to the procedure described in example 6 to provide the intermediate title compound, N-[3-(4-bromophenyl)propyl] (phenylmethoxy)carboxamide, (1.6 g, 54%). Electron spray M.S. 348 (M*+2).

Preparation of (Phenylmethoxy)-N-[3-(4-{2-[(phenylmethoxy)carbonylamino]ethyl}phenyl) propyl]carboxamide

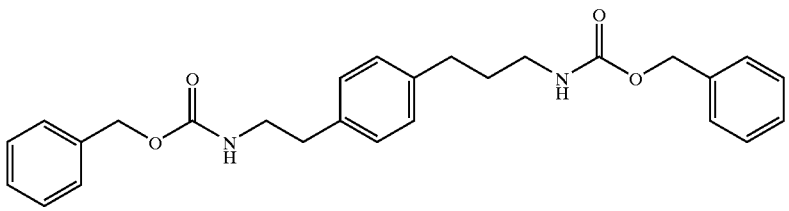

Scheme IV, step A: N-[3-(4-Bromophenyl)propyl] (phenylmethoxy)carboxamide (1.5 g, 4.3 mmol), (phenylmethoxy)-N-eth-2-enylcarboxamide (0.92 g, 5.17 mmol, prepared in example 8), 9-BBN-dimer (0.84 g, 3.45 mmol), [1,1'bis(diphenylphosphino)-ferrocene] dichloropalladium (11), PdCl2(dppf), (0.175 9, 0.22 mmol), 3N sodium hydroxide (3 mL), and pH=7 buffer hydrogen peroxide (2:1, 10 mL) were combined in a manner analogous to the procedure described in example 6 to provide the intermediate title compound, (phenylmethoxy)-N-[3-(4-{2-[(phenylmethoxy)carbonylamino]ethyl}phenyl)propyl] carboxamide, (0.68 g, 35%). Electron spray M.S. 447 (M*+H).

Preparation of 3-[4-(2-Aminoethyl)phenyl] propylamine Dihydrochloride

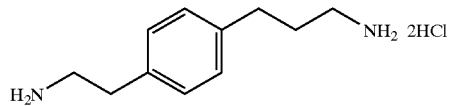

Scheme IV, step B: (Phenylmethoxy)-{N-[3-(4-{2-[(phenylmethoxy)carbonylamino]ethyl}phenyl)propyl] carboxamide (0.56 g, 1.25, mmol) and 10% palladium on carbon (0.5 g, 50 mole %) were combined and hydrogenation was carried out in a manner analogous to the procedure described in example 6 to provide the intermediate title compound, 3-[4-(2-aminoethyl)phenyl]propylamine dihydrochloride, (0.18 g, 81%) as a colorless oil. Electron spray M.S. 179 (M*+H).

Preparation of Final Title Compound

Scheme IV, step C: 3-[4-(2-aminoethyl) phenylpropylamine (0.18 g, 1.0 mmol), isopropylsulfonyl chloride (0.24 mL, 2.12 mmol) and DBU (0.33 mL, 2.2 mmol) were combined and sulfonylation was carried out in a manner analogous to the procedure described in example 2 to provide the final title compound, [(methylethyl) sulfonyl](2-[4-(3-{[(methylethyl)sulfonyl]amino}propyl) phenyl]ethyl}amine, (0.119 g, 30%) as a white crystalline solid. Electron spray M.S. 391 (M*+H).

| Theory: | C, 52.28 | H, 7.74 | N, 7.17 |
| Found: | C, 52.74 | H, 7.65 | N, 6.89 |

EXAMPLE 10

Preparation of [(Methylethyl)sulfonyl][2-(4-{3-[(methylsulfonyl)amino]propyl}phenyl)propyl]amine

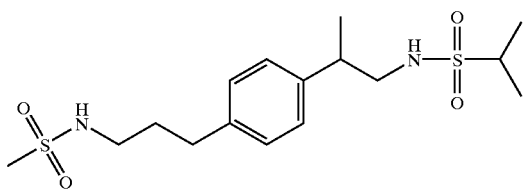

Preparation of N-{3-[4-(1-Methyl-2-{[(methylethyl)sulfonyl]amino}ethyl)phenyl]propyl}(phenylmethoxy)carboxamide

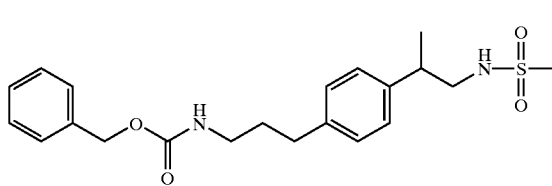

Scheme Vc, step A: 2-(4-Iodophenyl) propyl isopropylsulfonamide (1.5 g, 4.1 mmol), (phenylmethoxy)-N-prop-2-enylcarboxamide (0.94 g, 4.9 mmol, prepared in example 8), 9-BBN dimer (0.8 g, 3.28 mmol), [1,1'bis(diphenylphosphino)-ferrocene] dichloropalladium (II), PdCl$_2$(dppf) (0.17 g, 0.2 mmol), 3N sodium hydroxide (3 mL), and pH=7 buffer: hydrogen peroxide (2:1, 15 mL) were combined in a manner analogous to the procedure described in example 6 to provide the intermediate title compound, N-{3-[4-(1-methyl-2-{[(methylethyl)sulfonyl]amino}ethyl)phenyl]propyl}(phenylmethoxy)carboxamide, (1.74 g, 99%). Electron spray M.S. 431 (M*–H).

Preparation of {2-[4-(3-Aminopropyl)phenyl]propyl}(methylethyl)sufonyl]amine

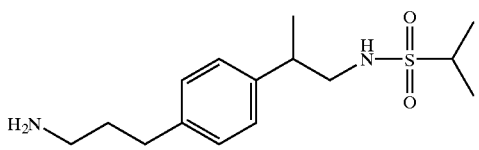

Scheme Vc, step B: N-{3-[4-(1-Methyl-2-{[(methylethyl)sulfonyl]amino}ethyl)phenyl]propyl}(phenylmethoxy)carboxamide (1 g, 2.31 mmol) and 10% palladium on carbon (0.5 g, 25 mole %) were combined and hydrogenation was carried out in a manner analogous to the procedure described in example 6 to provide the intermediate title compound, {2-[4-(3-aminopropyl)phenyl]propyl}[(methylethyl)sulfonyl]amine, (0.8 g, 87%) as a colorless oil. Electron spray M.S. 299 (M*+H).

Preparation of Final Title Compound

Scheme Vc, step C: {2-[4-(3-aminopropyl)phenyl]propyl}[(methylethyl)sulfonyl]amine (0.5 g, 1.67 mmol), methanesulfonyl chloride (0.15 mL, 1.84 mmol) and DBU (0.29 mL, 1.93 mmol) were combined and sulfonylation was carried out in a manner analogous to the procedure described in example 2 to provide the final title compound, [(methylethyl)sulfonyl][2-(4-{3-[(methylsulfonyl)amino]propyl}phenyl)propyl]amine, (0.15 g, 24%) as a white crystalline solid. Electron spray M.S. 377 (M*+H). Analysis for C$_{16}$H$_{28}$N$_2$O$_4$S$_2$:

| Theory: | C, 51.04 | H, 7.49 | N, 7.44 |
| Found: | C, 51.63 | H, 6.94 | N, 8.34 |

EXAMPLE 11

Preparation of [(Methylethyl)sulfonyl]{2-[4-(3-{[(methylethyl)sulfonyl]amino}propyl)phenyl]propyl}amine

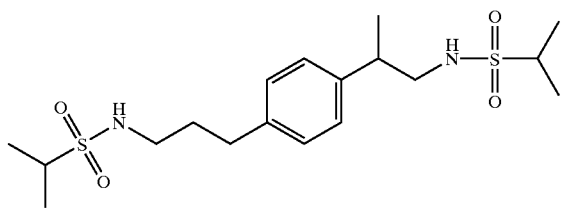

Scheme Vc, step C: {2-[4-(3-Aminopropyl)phenyl]propyl}[(methylethyl)sulfonylamine (0.3 g, 1 mmol, prepared in example 10), isopropylsulfonyl chloride (0.12 mL, 1.06 mmol), and DBU (0.2 mL, 1.17 mmol) were combined and sulfonylation was carried out in a manner analogous to the procedure described in example 2 to provide the title compound, [(methylethyl)sulfonyl]{2-[4-(3-{[(methylethyl)sulfonyl]amino}propyl)phenyl]propyl}amine, (0.17 g, 42%) as a white crystalline solid. Electron spray M.S. 405 (M*+H). Analysis for C$_{18}$H$_{32}$N$_2$O$_4$S$_2$:

| Theory: | C, 53.44 | H, 7.97 | N, 6.93 |
| Found: | C, 52.90 | H, 7.01 | N, 8.87 |

EXAMPLE 12

Preparation of [(Methylethyl)sulfonyl][2-(4-{2-[(methylsulfonyl)amino]ethyl}phenyl)propyl]amine

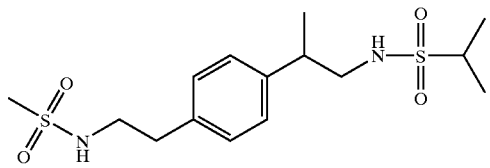

Preparation of N-{2-[4-(1-Methyl-2-{[(methylethyl)sulfonyl]amino}ethyl)phenyl]ethyl}(phenylmethoxy)carboxamide

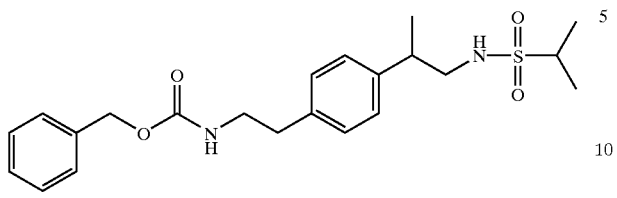

Scheme Va, step A: 2-(4-iodophenyl) propyl isopropylsulfonamide (1.5 g, 4.1 mmol), (phenylmethoxy)-N-vinylcarboxamide (0.87 g, 4.9 mmol, prepared in example 6), 9-BBN dimer (1.3 g, 5.3 mmol), [1,1'bis(diphenylphosphino)-ferrocene] dichloropalladium (II), PdCl$_2$(dppf) (0.17 g, 0.2 mmol), 3N sodium hydroxide (3 mL), and pH=7 buffer: hydrogen peroxide (2:1, 15 mL) were combined in a manner analogous to the procedure described in example 6 to provide the intermediate title compound, N{2-[4-(1-methyl-2-{[(methylethyl)sulfonyl]amino}ethyl)phenyl]ethyl}(phenylmethoxy)carboxamide, (0.6 g, 35%). Electron spray M.S. 417 (M*–H).

Preparation of {2-[4-(2-Aminoethyl)phenyl]propyl}[(methylethyl)sulfonyl]amine

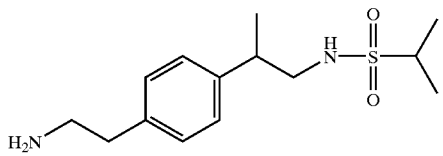

Scheme Va, step B: N-{2-[4-(1-Methyl-2-{[(methylethyl)sulfonyl]amino}ethyl)phenyl]ethyl}(phenylmethoxy)carboxamide (0.6 g, 1.44 mmol) and 10% palladium on carbon (0.5 g, 35 mole %) were combined and hydrogenation was carried out in a manner analogous to the procedure described in example 6 to provide the intermediate title compound, {2-[4-(2-aminoethyl)phenyl]propyl}[(methylethyl)sulfonyl]amine, (0.15 g, 37%) as colorless oil. Electron spray M.S. 285 (M*+H).

Preparation of Final Title Compound

Scheme Va, step C: {2-[4-(2-Aminoethyl)phenyl]propyl}[(methylethyl)sulfonyl]amine (0.15 g, 0.53 mmol), methanesulfonyl chloride (0.1 mL, 0.58 mmol) and DBU (0.1 mL, 0.61 mmol) were combined and sulfonylation was carried out in a manner analogous to the procedure described in example 2 to provide the final title compound, [(methylethyl)sulfonyl][2-(4-{2-[(methylsulfonyl)amino]ethyl}phenyl)propyl]amine, (0.15 g, 78%) as a white crystalline solid. Electron spray M.S. 363 (M*+H). Analysis for C$_{15}$H$_{26}$N$_2$O$_4$S$_2$:

| | | | |
|---|---|---|---|
| Theory: | C, 49.70 | H, 7.23 | N, 7.73 |
| Found: | C, 49.68 | H, 7.19 | N, 7.45 |

EXAMPLE 13

Preparation of [(Methylethyl)sulfonyl]{2-[4-(2-{[(methylethyl)sulfonyl]amino}ethyl)phenyl]propyl}amine

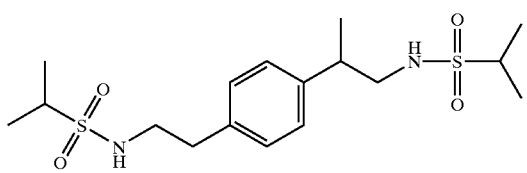

Scheme Va, step C: {2-[4-(2-Aminoethyl)phenyl]propyl}[(methylethyl)sulfonyl]amine (0.15 g, 0.53 mmol, prepared in example 12), isopropylsulfonyl chloride (0.1 mL, 0.58 mmol) and DBU (0.1 mL, 0.61 mmol) were combined and sulfonylation was carried out in a manner analogous to the procedure described in example 2 to provide the title compound, [(methylethyl)sulfonyl]{2-[4-(2-{[(methylethyl)sulfonyl]amino}ethyl)phenyl]propyl}amine, (0.149 g, 72%) as a white crystalline solid. Electron spray M.S. 391 (M*+H). Analysis for C$_{17}$H$_{30}$N$_2$O$_4$S$_2$.

| | | | |
|---|---|---|---|
| Theory: | C, 52.28 | H, 7.74 | N, 7.17 |
| Found: | C, 52.46 | H, 7.67 | N, 6.90 |

EXAMPLE 14

Preparation of {2-[3-Fluoro-4-(1-methyl-2-{[(methylethyl)sulfonyl]amino}ethyl)phenyl]propyl}(methylethyl)sulfonyl]amine

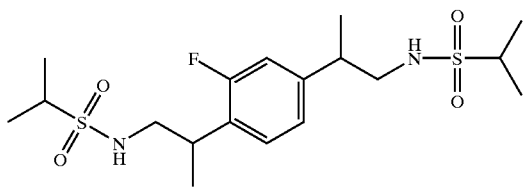

Preparation of 1-(4-Acetyl-2-fluorophenyl)ethan-1-one

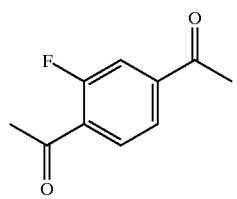

Into a 100 mL single neck flask were placed 1,4-dibromo-2-fluorobenzene (2.35 g, 9.2 mmol), dichlorobis(triphenylphosphine) palladium (II) (0.645 g, 0.92 mmol), tributyt (1-ethoxyvinyl)tin (10 g, 27.7 mmol), in THF (50 mL), and the mixture was heated at reflux while stirring for 18 hours. The reaction was cooled to room temperature and poured into 5N HCl (20 mL). The product was extracted with EtOAc and the organic layer was separated and washed twice with water, dried over anhydrous Na$_2$SO$_4$, filtered, and concentrated under reduced vacuum. The resulting semi-solid was purified via flash chromatography (Silica gel, isocratic) and eluting with a solvent of Hexanes/EtOAc 90:10 to provide the intermediate title compound, 1-(4-acetyl-2-fluorophenyl)ethan-1-one, (1.65 g, 100%) as a solid. Electron spray M.S. 180.9 (M*)

Preparation of 2-[4-(Cyanoethyl)-3-fluorophenyl] propanenitrile

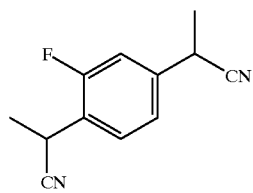

Into a 250 mL single neck flask was placed 1-(4-acetyl-2-fluorophenyl)ethan-1-one (1.6 g, 9.2 mmol) in DME (100 mL) and the solution was cooled down to −10° C. Tosylmethyl isocyanide (8.2 g, 42 mmol) was added and the mixture was stirred at −10° C. for 15 minutes. A solution of potassium t-butoxide (5.2 g, 46.2 mmol) in t-butanol was added to the mixture and the reaction mixture was allowed to warm up to RT while stirring overnight. The reaction was poured into water (20 mL), the product was extracted with EtOAc, the organic layer was separated and washed twice with water, dried over anhydrous Na$_2$SO$_4$, filtered, and concentrated under vacuum. The resulting semi-solid was purified via flash chromatography (Silica gel, isocratic) and eluting with a solvent of Hexanes/EtOAc 80:20 to provide the intermediate tide compound, 2-[4-(cyanoethyl)-3-fluorophenyl]propanenitrile, (0.545 g, 29%) as a solid.

Preparation of 1-[4-(Aminoethyl)-2-fluorophenyl] ethylamine Dihydrochloride

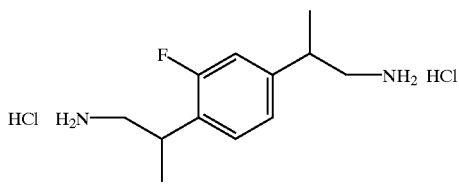

Scheme Ia, step B: Into a 25 mL single neck flask was placed 2-[4-(cyanoethyl)-3-fluorophenyl]propanenitrile (545 mg, 2.7 mmol) in THF (10 mL). Boron dimethylsulfide 2 M in THF (3 mL, 5.95 mmol) was added to the solution and the mixture was heated at reflux for 12 hours. The reaction mixture was cooled to RT and quenched with saturated solution of HCl in methanol (10 mL). Diethyl ether (10 mL) was added to the reaction mixture and the mixture was cooled down to 0° C. The product was precipitated out of the solution as dihydrochloride salt. The salt was filtered and dried under vacuum to provide the intermediate title compound, 1-[4-(aminoethyl)-2-fluorophenyl]ethylamine dihydrochloride, (595 mg, 78%) as a white solid crystal. Electron spray M.S. 211 (M*-2HCl)

Preparation of Final Title Compound

Scheme Ia, step C: Into a 25 mL single neck flask was placed 1-[4-(aminoethyl)-2-fluorophenyl]ethylamine dihydrochloride (350 mg, 1.24 mmol) in methylene chloride (5 mL) was cooled down to 0° C. 1,8-diazabicyclo [5.4.0] undec-7-ene, DBU, (1.1 mL, 7.45 mmol) was added and after 30 minutes isopropylsulfonyl chloride (0.310 mL, 2.73 mmol) was subsequently added to the reaction mixture. The mixture was warmed up to RT while stirring for 5 hours. The reaction mixture was quenched with a 0.1 M HCl until pH was below 4–5. The product was extracted with methylene chloride and the organic layer was separated and washed twice with water, dried over anhydrous sodium sulfate, filtered, and concentrated under vacuum. The resulting semi-solid was purified via flash chromatography (Silica gel, gradient) and eluting with a solvent of Hexanes/EtOAc 40–50% to provide the final title compound, {2-[3-fluoro-4-(1-methyl-2-{[(methylethyl)sulfonyl]amino}ethyl) phenyl]propyl}[(methylethyl)sulfonyl]amine, (95 mg, 18%) as a white solid. Electron spray M.S. 423.1 (M*+H). Analysis for C$_{18}$H$_{31}$FN$_2$O$_4$S$_2$:

| | | | |
|---|---|---|---|
| Theory: | C, 51.16 | H, 7.39 | N, 6.63 |
| Found: | C, 50.83 | H, 7.22 | N, 6.48 |

EXAMPLE 15

Preparation of {2-[2,5-Difluoro-4-(1-methyl-2-{[(methylethyl)sulfonyl]amino}ethyl)phenyl]propyl} [(methylethyl)sulfonyl]amine

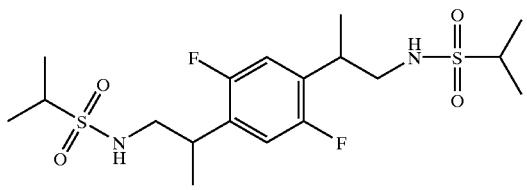

Preparation of 1-(4-Acetyl-2,5-difluorophenyl) ethan-1-one

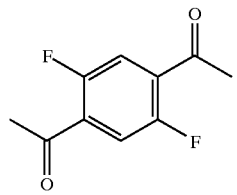

1,4-dibromo-2,5-Difluorobenzene (2.5 g, 9.2 mmol), dichlorobis(triphenylphosphine) palladium (II) (0.645 g, 0.92 mmol), tributyl-(1-ethoxyvinyl)tin (10 g, 27.7 mmol), and THF (50 mL) were combined in a manner analogous to the procedure described in example 14 to provide the intermediate title compound, 1-(4-acetyl-2,5-difluorophenyl)ethan-1-one, (1.8 g, 100%) as a white crystal. Electron spray M.S. 197.9 (M*−H).

51

Preparation of 2-[4-(Cyanoethyl)-2,5-difluorophenyl]propanenitrile

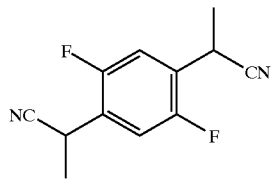

1-(4-Acetyl-2,5-difluorophenyl)ethan-1-one (1.8 g, 9.2 mmol), tosylmethyl isocyanide (9 g, 43.4 mmol), and potassium t-butoxide (5.7 g, 51 mmol) in t-butanol (10 mL) were combined in a manner analogous to the procedure described in example 14 to provide the intermediate title compound, 2-[4-(cyanoethyl)-2,5-difluorophenyl]propanenitrile, (0.5 g, 25%) as a solid. Ion spray M.S. 237.9 (M*+H$_2$O).

Preparation of 2-[4-(2-Amino-isopropyl)-2,5-difluorophenyl]propylamine Dihydrochloride

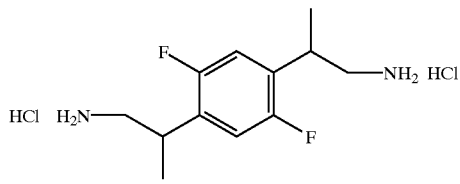

Scheme Ia, step B: 2-[4-(Cyanoethyl)-2,5-difluorophenyl]propanenitrile (500 mg, 2.27 mmol) and boron dimethylsulfide 2 M in THF (2.5 mL, 5 mmol) were combined in a manner analogous to the procedure described in example 14 to provide the intermediate title compound, 2-[4-(2-amino-isopropyl)-2,5-difluorophenyl]propylamine dihydrochloride, (645 mg, 94%) as a white crystal. Electron spray M.S. 229 (M*−2HCl).

Preparation of Final Title Compound

Scheme Ia, step C: Into a 25 mL single neck flask was placed 2-[4-(2-amino-isopropyl)-2,5-difluorophenyl]propylamine dihydrochloride (400 mg, 1.33 mmol) in methylene chloride (7 mL) and the mixture was cooled down to 0° C. DBU (1.2 mL, 8 mmol) was added to the mixture and after 30 minutes isopropylsulfonyl chloride (0.330 mL, 2.92 mmol) was subsequently added to the reaction mixture. The mixture was warmed up to RT while stirring for 5 hours. The reaction mixture was quenched with a 0.1 M HCl until pH was below 4–5. The product was extracted with methylene chloride and the organic layer was separated and washed twice with water, dried over anhydrous sodium sulfate, filtered, and concentrated under reduced vacuum. The resulting semi-solid was triturated out of diethyl ether to provide the final title compound, {2-[2,5-difluoro-4-(1-methyl-2-{[(methylethyl)sulfonyl]amino}ethyl)phenyl]propyl}[(methylethyl)sulfonyl]amine, (225 mg, 38%) as a white solid. Electron Spray M.S. 441.2 (M*+H). Analysis for C$_{18}$H$_{30}$F$_2$N$_2$O$_4$S$_2$:

52

| Theory: | C, 49.07 | H, 6.86 | N, 6.36 |
| Found: | C, 48.31 | H, 6.61 | N, 6.22 |

EXAMPLE 16

Preparation of [2-(2,5-Dimethyl-4-{1-methyl-2-[(methylsulfonyl)amino]ethyl}phenyl)propyl](methylsulfonyl)amine

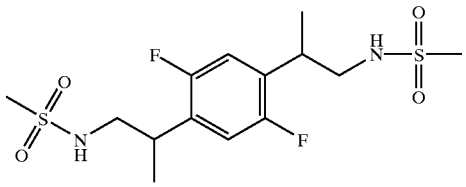

Scheme Ia, step C: 2-[4-(2-Amino-isopropyl)-2,5-difluorophenyl]propylamine dihydrochloride (165 mg, 0.55 mmol, prepared in example 15), methylene chloride (7 mL), DBU (0.5 mL, 3.3 mmol), and methanesulfonyl chloride (0.095 mL, 1.2 mmol) were combined in a manner analogous to the procedure described in example 15 to provide the title compound, [2-(2,5-dimethyl-4-{1-methyl-2-[(methylsulfonyl)amino]ethyl}phenyl)propyl](methylsulfonyl)amine, (85 mg, 40%) as a white solid. Electron spray M.S. 385.1 (M*+H). Analysis for C$_{14}$H$_{22}$F$_2$N$_2$O$_4$S$_2$:

| Theory: | C, 43.73 | H, 5.77 | N, 7.29 |
| Found: | C, 43.34 | H, 5.70 | N, 7.07 |

EXAMPLE 17

Preparation of {2-[3-Fluoro-4-(1-hydroxy-1-methyl-2-{[(methylethyl)sulfonyl]amino}ethyl)phenyl]-2-hydroxypropyl}[(methylethyl)sulfonyl]amine

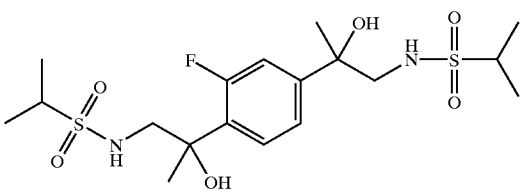

53

Preparation of 2-{4-[2-Amino-1-(1,1-dimethyl-1-silaethoxy)-isopropyl]-3-fluorophenyl}2-(1,1-dimethyl-1-silaethoxy)propylamine Dihydrochloride

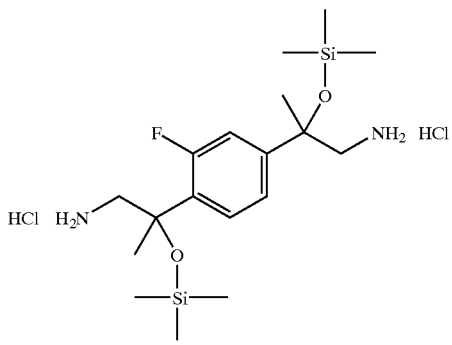

Scheme II, steps A and B: Into a 25 mL single neck flask were placed 1-(4-acetyl-2-fluorophenyl)ethan-1-one (4.3 g, 23.87 mmol, prepared in example 14), trimethylsilyl cyanide (10 g, 80 mmol), and catalytic amount of zinc iodide (0.76 g, 2.3 mmol). The mixture was stirred at RT for 12 hours. The reaction mixture was poured into 10% solution of the sodium bicarbonate (100 mL). The product was extracted with methylene chloride and the organic layer was separated and washed twice with water, dried over anhydrous sodium sulfate, filtered, and concentrated under vacuum. The resulting oil was dissolved in THF (100 mL) and the mixture was treated with boron dimethylsulfide, 10M solution (7.16 mL, 71.6 mmol). The reaction mixture was refluxed for 6 hours and then cooled down to RT and quenched with saturated solution of HCl in methanol (100 mL). Diethyl ether (100 mL) was added to the reaction mixture and the mixture was cooled down to 0° C. The product was precipitated out of the solution as dihydrochloride salt. The salt was filtered and dried under vacuum to provide the intermediate title compound, 2-{[2-amino-1-(1,1-dimethyl-1-silaethoxy)-isopropyl]-3-fluorophenyl}2-(1,1-dimethyl-1-silaethoxy)propylamine dihydrochloride, (6.5 g, 86%) as a white crystal.

Preparation of Final Title Compound

Scheme II, step C: 2-{4-[2-Amino-1-(1,1-dimethyl-1-silaethoxy)-isopropyl]-3-fluorophenyl)}-2-(1,1-dimethyl-1-silaethoxy)propylamine dihydrochloride (6.5 g, 20.7 mmol), DBU (18.5 mL, 124.2 mmol) and isopropylsulfonyl chloride (5.1 mL, 45.5 mmol) were combined and sulfonylation was carried out in a manner analogous to the procedure described in example 15 to provide the final tide compound, {2-[3-fluoro-4-(1-hydroxy-1-methyl-2-{[(methylethyl)sulfonyl]amino}ethyl)phenyl]-2-hydroxypropyl}[(methylethyl)sulfonyl]amine, (354 mg, 4%) as a white solid crystal. Electron spray M.S. 472.3 (M*+H$_2$O). Analysis for C$_{18}$H$_{31}$FN$_2$O$_6$S2:

| Theory: | C, 47.56 | H, 6.87 | N, 6.16 |
| Found:  | C, 46.95 | H, 6.78 | N, 6.33 |

54

EXAMPLE 18

Preparation of {2-Fluoro-2-[3-fluoro-4-(1-fluoro-1-methyl-2-{[(methylethyl)sulfonyl]amino}ethyl)phenyl]propyl}[(methylethyl)sulfonyl]amine

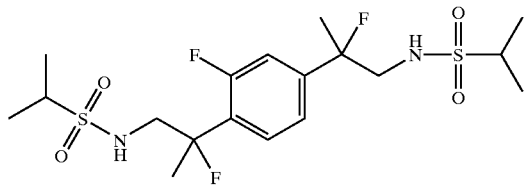

Scheme II, step D: Into a 10 mL single neck flask was placed {2-[3-fluoro-4-(1-hydroxy-1-methyl-2-{[(methylethyl)sulfonyl]amino}ethyl)phenyl]-2-hydroxypropyl}[(methylethyl)sulfonyl]amine (250 mg, 0.55 mmol) in methylene chloride (3 mL) and the mixture was cooled down to −78° C. DAST (0.16 mL, 1.2 mmol) was added to the mixture dropwise and the reaction mixture was warmed up gradually to RT while stirring for 12 h. The reaction mixture was quenched with water (10 mL). The product was extracted with methylene chloride and the organic layer was separated and washed twice with water, dried over anhydrous sodium sulfate, filtered, and concentrated under vacuum. The resulting semi-solid was further purified via flash chromatography (silica gel, gradient) and eluting with a solvent of Hexanes/EtOAc 25–40% to provide the title compound, {2-fluoro-2-[3-fluoro-4-(1-fluoro-1-methyl-2-{[(methylethyl)sulfonyl]amino}ethyl)phenyl]propyl}[(methylethyl)sulfonyl]amine, (189 mg, 75%) as a white solid. Electron Spray M.S. 476.3 (M*+H$_2$O). Analysis for C$_{18}$H$_{29}$F$_3$N$_2$O$_4$S$_2$:

| Theory: | C, 47.15 | H, 6.37 | N, 6.11 |
| Found:  | C, 46.08 | H, 6.25 | N, 5.95 |

EXAMPLE 19

Preparation of [(Methylethyl)sulfonyl]{2-[3-(2-{[(methylethyl)sulfonyl]amino}ethyl)phenyl]propyl}amine

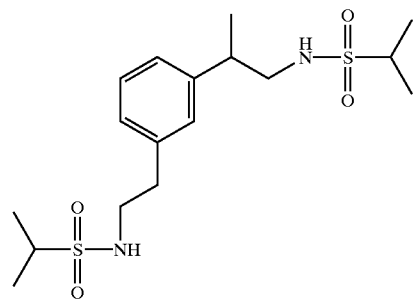

Preparation of 2-(3-Bromophenyl)propanenitrile

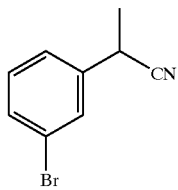

3-Bromoacetophenone (20 g, 100 mmol), tosylmethyl isocyahide (29.3 g, 150 mmol), and potassium t-butoxide (22.4 g, 200 mmol) in t-butanol (20 mL) were combined in a manner analogous to the procedure described in example 14 to provide the intermediate title compound, 2-(3-bromophenyl)propanenitrile, (13.1 g, 62%) as a orange oil.

Preparation of 2-(3-Bromophenyl)propylamine

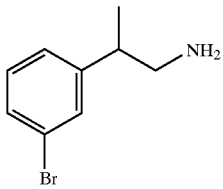

Scheme Ia, step B; 2-(3-Bromophenyl)propanenitrile (9.5 g, 45.2 mmol) and boron dimethylsulfide 10 M in THF (6.8 mL, 68 mmol) were combined in a manner analogous to the procedure described in example 14 to provide the hydrochloride of the intermediate title compound, 2-(3-bromophenyl)propylamine. The salt was converted to free amine by the addition of $H_2O$ (100 mL) and adjusting the pH to 13 with 1M NaOH. The product was extracted with EtOAc and the organic layer was separated and washed twice with $H_2O$, dried over anhydrous $Na_2SO_4$, filtered, and concentrated under reduced vacuum to give intermediate title compound, 2-(3-bromophenyl)propylamine, (9.7 g, 100%) as an oil. Electron spray M.S. 214 (M*).

Preparation of [2-(3-Bromophenyl)propyl][(methylethyl)sulfonyl]amine

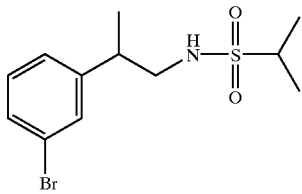

2-(3-Bromophenyl)propylamine (9.7 g, 45.3 mmol) was combined with isopropylsulfonyl chloride (6.1 mL, 54.4 mmol), and DBU (10.2 mL, 68 mmol) in a manner analogous to the procedure described in example 2 to provide the final title compound, [2-(3-bromophenyl)propyl][(methylethyl)sulfonyl]amine, (4.5 g, 31%) as a white crystalline solid. Electron spray M.S. 320 (M*–H).

Preparation of N-{2-[3-(1-methyl-2-{[(methylethyl)sulfonyl]amino}ethyl)phenyl]ethyl(phenylmethoxy)carboxamide

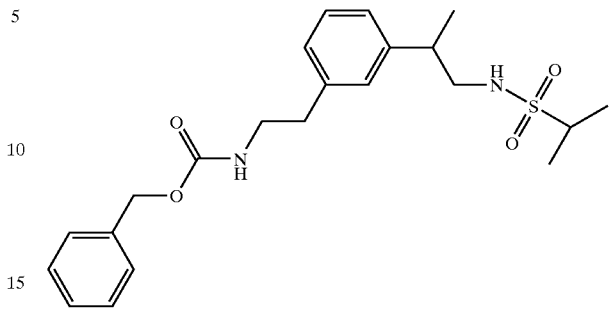

Scheme Va, step A: [2-(3-bromophenyl)propyl[] (methylethyl)sulfonyl]amine (0.75 g, 2.34 mmol), (phenylmethoxy)N-vinylcarboxamide (0.62 g, 3.51 mmol, prepared in example 6), 9-BBN-dimer (0.51 g, 2.11 mmol), [1,1'bis(diphenylphosphino)-ferrocene] dichloropalladium (II), $PdCl_2(dppf)$ (0.100 g, 0.12 mmol), 3N sodium hydroxide (3 mL), and pH=7 buffer: hydrogen peroxide (2:1, 10 mL) were combined in a manner analogous to the procedure described in example 6 to provide the intermediate title compound, N-{2-[3-(1-methyl-2-{[(methylethyl)sulfonyl]amino}ethyl)phenyl]ethyl}(phenylmethoxy)carboxamide, (0.84 g, 86%) as an light brown oil. Electron spray M.S. 419 (M*–H).

Preparation of {2-[3-(2-Aminoethyl)phenyl]propyl}[(methylethyl)sulfonyl]amine

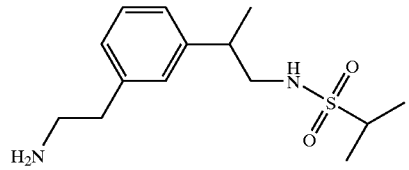

Scheme Va, step B: N-{2-[3-(1-methyl-2-{[(methylethyl)sulfonyl]amino}ethyl)phenyl]ethyl}(phenylmethoxy)carboxamide (0.84 g, 2 mmol) and 10% palladium on carbon (0.5 g, 60 mole %) were combined and hydrogenation was carried out in a manner analogous to the procedure described in example 6 to provide the intermediate title compound, {2-[3-(2-aminoethyl)phenyl]propyl}[(methylethyl)sulfonyl]amine, (0.57 g, 100%) as colorless oil. Electron spray M.S. 285 (M*+H).

Preparation of Final Title Compound

Scheme Va, step C: {2-[3-(2-Aminoethyl)phenyl]propyl}[(methylethyl)sulfonyl]amine (0.57 g, 2 mmol), isopropylsulfonyl chloride (0.24 mL, 2.1 mmol) and DBU (0.33 mL, 2.2 mmol) were combined and sulfonylation was carried out in a manner analogous to the procedure described in example 2 to provide the final title compound, [(methylethyl)sulfonyl]{2-[3-(2-{[(methylethyl)sulfonyl]amino}ethyl)phenyl]propyl}amine, (0.422 g, 54%) as a white crystalline solid. Electron spray M.S. 391 (M*+H). Analysis for $C_{17}H_{30}N_2O_4S_2$:

| Theory: | C, 52.28 | H, 7.74 | N, 7.17 |
| --- | --- | --- | --- |
| Found: | C, 52.83 | H, 7.65 | N, 6.89 |

EXAMPLE 20

Preparation of [(Methylethyl)sulfonyl]2-[4-(2-{[(methylethyl)sulfonyl]amino}ethyl)cyclohexyl]ethyl}amine

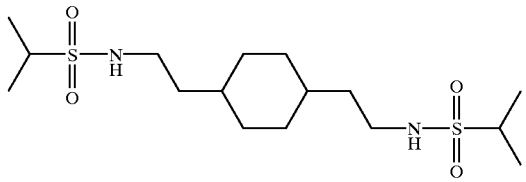

Preparation of 2-[4-(2-Aminoethyl)phenyl]ethylamine

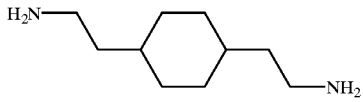

Into a 250 mL reduction vessel were placed 1,4-phenylenediacetonitrile (2 g, 12.8 mmol), acetic acid (95 mL), and platinum oxide (0.25 g) and the mixture was heated at 60° C. under 60 psi (413.7 kPa) of hydrogen gas for 6 hours. The reaction was cooled to room temperature and filtered through a Celite® cake and the filtrate was concentrated under reduced vacuum to give the intermediate title compound, 2-[4-(2-aminoethyl)cyclohexyl]ethylamine, (3.7 g, 100%) as an oil. Electron spray M.S. 171 (M*+1).

Preparation of Final Title Compound

Scheme I, step C': Into a 50 mL single neck flask were placed 2-[4-(2-aminoethyl)cyclohexyl]ethylamine (1 g, 3.45 mmol), 1,8-diazabicyclo [5.4.0] undec-7-ene, DBU, (2.6 mL, 17.25 mmol), and isopropylsulfonyl chloride (0.85 mL, 7.6 mmol), in THF:methylene chloride (15:15 mL) at 0° C. The mixture was warmed up to room temperature while stirring for 3 hours. The reaction mixture was quenched with 0.1 M HCl (100 mL) until pH was below 4–5. The product was extracted with $CH_2Cl_2$ and the organic layer was separated and washed twice with $H_2O$, dried over anhydrous $Na_2SO_4$, filtered, and concentrated under reduced vacuum. The resulting semi-solid was purified via flash chromatography (Silica gel, isocratic) and eluting with a solvent of Hexanes/EtOAc 50% to provide the final title compound, [(methylethyl)sulfonyl]{2-[4-(2-{[(methylethyl)sulfonyl]amino}ethyl)cyclohexyl]ethyl}amine, (0.3 g, 23%) as a white crystalline solid. Electron spray M.S. 383 (M+1). Analysis for $C_{16}H_{34}N_2O_4S_2$:

| Theory: | C, 50.23 | H, 8.96 | N, 7.32 |
| --- | --- | --- | --- |
| Found: | C, 50.20 | H, 9.00 | N, 7.24 |

EXAMPLE 21

Preparation of [(Methylethyl)sulfonyl]{3-[4-(3-{[(methylethyl)sulfonyl]amino}propyl)cyclohexyl]propyl}amine

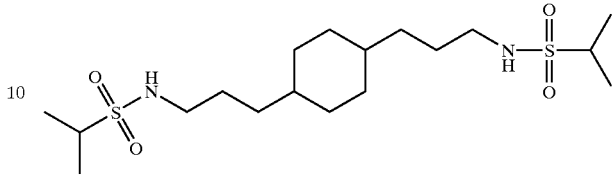

Preparation of 3-[4-(3-Aminopropyl)cyclohexyl]propylamine

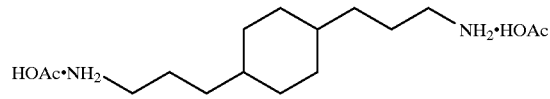

Into a 250 mL reduction vessel were placed (phenylmethoxy)-N-[3(4-{3-[(phenylmethoxy)carbonylamino]propyl}phenyl)propyl]carboxamide (0.93 g, 2.02 mmol), acetic acid (75 mL), and platinum oxide (0.5 g) and the mixture was heated at 60° C. under 60 psi (413.7 kPa) of hydrogen gas for 12 hours. The reaction was cooled to room temperature and filtered through a Celite® cake and the filtrate was concentrated under reduced vacuum to give the intermediate title compound, 3-[4-(3-aminoethyl)cyclohexyl]propyllamine, (0.64 g, 100%) as a diacetic acid salt. Electron spray M.S. 199 (M*+1).

Preparation of Final Title Compound

3-[4-(3-aminopropyl)cyclohexyl]propylamine (0.64 g, 2 mmol), isopropylsulfonyl chloride (0.56 mL, 5 mmol) and DBU (1.5 mL, 10 mmol) were combined and sulfonylation was carried out in a manner analogous to the procedure described in example 1 to provide the final title compound, [(methylethyl)sulfonyl]{3-[4-(3-{[(methylethyl)sulfonyl]amino}propyl)cyclohexyl]propyl}amine, (0.281 g, 34%) as a white crystalline solid. Electron spray M.S. 411 (M*+1). Analysis for $C_{18}H_{38}N_2O_4S_2$:

| Theory: | C, 52.65 | H, 9.33 | N, 6.82 |
| --- | --- | --- | --- |
| Found: | C, 52.68 | H, 9.94 | N, 6.79 |

EXAMPLE 22

Preparation of [(Methylethyl)sulfonyl]{2-[6-(2-{[(methylethyl)sulfonyl]amino}ethyl)(2-naphthyl)]ethyl}amine

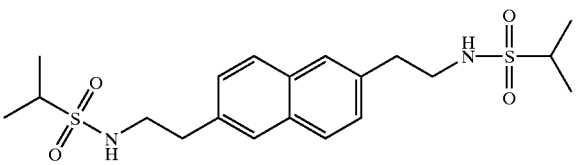

Preparation of 2-[6-(2-Aminoethyl)-2-naphthyl]
ethylamine Dihydrochloride

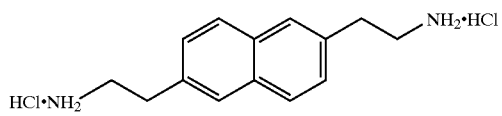

Scheme I, step B: Into a 100 mL single neck flask was placed 2,6-naphthalene diacetonitrile (1 g, 4.85 mmol) in THF (20 mL). Boron dimethylsulfide 2 M in THF (5.3 mL, 10.67 mmol) was added to the solution and the mixture was heated to reflux over night. The reaction mixture was cooled down to room temperature and quenched with saturated solution of HCl in methanol (10 mL). Diethyl ether (20 mL) was added to the mixture and it was cooled down to 0° C. The product was precipitated out of the solution as dihydrochloride salt. The salt was filtered and dried in vacuum to provide the intermediate title, 2-[6(2-aminoethyl)-2-naphthyl]ethylamine dihydrochloride (1.4 g, 100%) as a white solid crystal. Electron spray M.S. 215.1 (M*−2HCl).

Preparation of Final Title Compound

Scheme I, step C: Into a 100 mL single neck flask was placed 2-[6-(2-aminoethyl)2-naphthyl]ethylamine dihydrochloride (1 g, 3.48 mmol) in methylene chloride (15 mL) and the solution was cooled down to 0° C. 1,8-diazabicyclo[5.4.0] undec-7-ene, DBU, (3.1 mL, 21 mmol) was added to the mixture and after 30 minutes isopropylsulfonyl chloride (7.6 mL, 21 mmol) was added to the reaction mixture. The mixture was warmed up to RT while stirring for 4 hour. The reaction mixture was quenched with a 0.1 M HCl until pH was below 4–5. The product was extracted with EtOAc and the organic layer was separated and washed twice with water, dried over anhydrous Na$_2$SO$_4$, filtered, and concentrated under reduced vacuum. The resulting semi-solid was purified via flash chromatography (Silica gel, isocratic) and eluting with a solvent of Hexanes/EtOAc 40% to provide the final title compound, (250 mg, 18%) as a white crystalline solid. Electron pray M.S. 425.3 (M*−H). Analysis for C$_{20}$H$_{30}$N$_2$O$_4$S$_2$H$_2$O:

| Theory: | C, 55.84 | H, 7.12 | N, 6.51 |
| Found: | C, 55.67 | H, 6.91 | N, 6.64 |

EXAMPLE 23

Preparation of [(Methylethyl)sulfonyl]{2-[5-(2-{[(methylethyl)sulfonyl]amino}ethyl)naphthyl]ethyl}amine

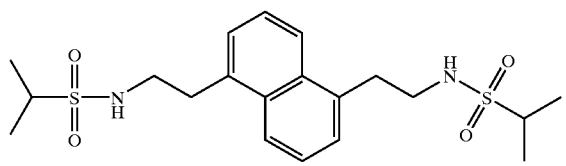

Preparation of (Phenylmethoxy)-N-[2-(5-{2-[(phenylmethoxy)carbonylamino]ethyl}naphthyl)ethyl]carboxamide

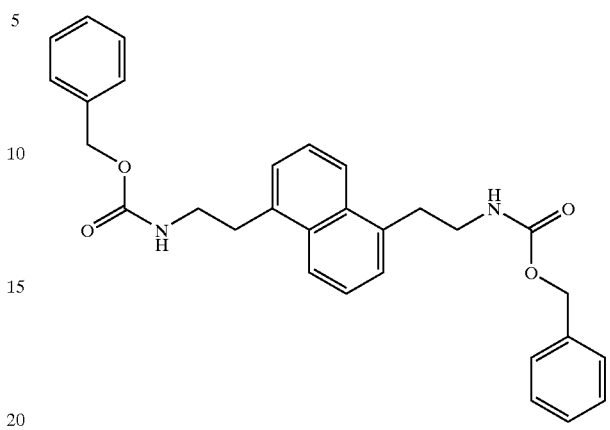

Scheme IV, step A: 1,5-Dibromonaphthalene (0.5 g, 1.75 mmol), (phenylmethoxy)-N-vinylcarboxamide (0.77 g, 4.37 mmol, prepared in example 6), 9-BBN dimer (0.53 g, 2.19 mmol), [1,1'bis(diphenylphosphino)-ferrocene] dichloropalladium (II), PdCl$_2$(dppf), (0.143 g, 0.175 mmol), 3N sodium hydroxide (3 mL), and pH=7 buffer: hydrogen peroxide (2:1, 10 mL) were combined in a manner analogous to the procedure described in example 6 to provide the intermediate title compound, (phenylmethoxy)N-[2-(5-{2-[(phenylmethoxy)carbonylamino]ethyl}naphthyl)ethyl]carboxamide, (0.6 g, 71%). Electron spray M.S. 483 (M*+H).

Preparation of 2-[5-(2-Aminoethyl)naphthyl]
ethylamine

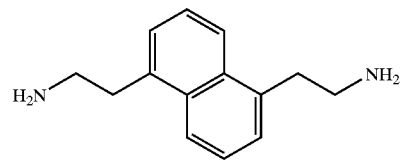

Scheme IVa, step B: (Phenylmethoxy)-N-[2-(5-{2-[(phenylmethoxy)carbonylamino]ethyl}naphthyl)ethyl]carboxamide (0.6 g, 1.24 mmol) and 10% palladium on carbon (0.5 g, 83 mole %) were combined and hydrogenation was carried out in a manner analogous to the procedure described in example 6 to provide the intermediate title compound, 2-[5-(2-aminoethyl)naphthyl]ethylamine, (0.12 g, 44%) as a colorless oil. Electron spray M.S. 215 (M$^+$+H).

Preparation of Final Title Compound

Scheme IV, step C: 2-[5-(2-Aminoethyl)naphthyl]ethylamine (0.12 g, 0.56 mmol), isopropylsulfonyl chloride (0.13 mL, 1.18 mmol) and DBU (0.18 mL, 1.18 mmol) were combined and sulfonylation was carried out in a manner analogous to the procedure described in example 2 to provide the final title compound (0.12 g, 50%) as a white crystalline solid. Electron spray M.S. 427 (M*+H). Analysis for C$_{20}$H$_{30}$N$_2$O$_4$S$_2$:

| Theory: | C, 56.31 | H, 7.09 | N, 6.57 |
| --- | --- | --- | --- |
| Found: | C, 56.43 | H, 7.02 | N, 6.42 |

EXAMPLE 24

Preparation of [(Methylethyl)sulfonyl]{2-[4-(2-{[(methylethyl)sulfonyl]amino}ethyl)naphthyl]ethyl}amine

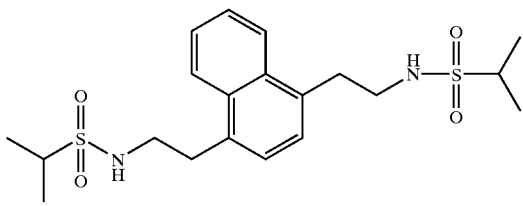

Preparation of 2-[4-(Cyanomethyl)naphthyl]ethanenitrile

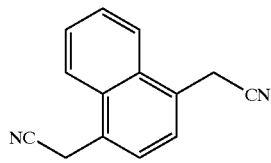

A solution of 1,4-bis-(bromomthyl)naphthalene (1 g, 3.18 mmol) in DMSO (10 mL) was treated with potassium cynide (435 mg, 6.7 mmol) and the reaction was stirred at 40° C. for 12 hours (over night). The reaction mixture was cooled to room temperature and added to H$_2$O (30 mL). The product was extracted with EtOAc and the organic layer was separated and washed twice with water, dried over anhydrous Na$_2$SO$_4$, filtered, and concentrated under reduced vacuum. The resulting semi-solid was purified via flash chromatography (Silica gel, gradient) and eluting with a solvent of Hexanes/EtOAc 30–40% to provide the intermediate title compound, 2-[4-(cyanomethyl)naphthyl]ethanenitrile, (200 mg, 30%) as a white crystalline solid. Electron pray M.S. 224.1 (M*+H$_2$O).

Preparation of 2-[4-(2-Aminoethyl)naphthyl]ethylamine Dihydrochloride

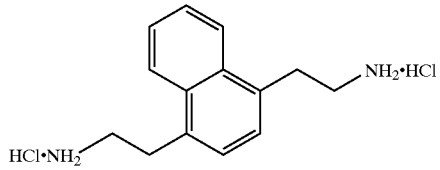

Scheme I, step B': Into a 100 mL single neck flask was placed 2-[4-(cyanomethyl)naphthyl]ethanenitrile (200 mg, 0.97mmol) in THF (5 mL). Boron dimethylsulfide 2 M in THF (1.1 mL, 2.1 mmol) was added to the solution and the mixture was heated to reflux over night. The reaction mixture was cooled down to room temperature and quenched with saturated solution of HCl in methanol (5 mL). Diethyl ether (20 mL) was added to the mixture and it was cooled down to 0° C. The product was precipitated out of the solution as dihydrochloride salt. The salt was filtered and dried in vacuum to provide the intermediate title compound, 2-[4-(2-aminoethyl)naphthyl]ethylamine hydrochloride, (275 mg, 99%) as a white solid crystal. Electron spray M.S. 215.2 (M*–2HCl).

Preparation of Final Title Compound

Scheme I, step C': Into a 25 mL single neck flask was placed 2-[4-(2-aminoethyl)naphthyl]ethylamine dihydrochloride (275 g, 1 mmol) in methylene chloride (5 mL) and the solution was cooled down to 0° C. 1,8-diazabicyclo [5.4.0] undec-7-ene, DBU, (900 µL, 6 mmol) was added to the mixture and after 30 minutes isopropylsulfonyl chloride (250 µL, 2.2 mmol) was added to the reaction mixture. The mixture was warmed up to RT while stirring for 2 hour. The reaction mixture was quenched with a 0.1 M HCl until pH was below 4–5. The product was extracted with EtOAc and the organic layer was separated and washed twice with water, dried over anhydrous Na$_2$SO$_4$, filtered, and concentrated under reduced vacuum. The resulting semi-solid was purified via flash chromatography (Silica gel, gradiet) and eluting with a solvent of Hexanes/EtOAc 35–45% to provide the final title compound, (125 mg, 29%) as a white crystalline solid. Electron pray M.S. 425.3 (M*–H). Analysis for $C_{20}H_{30}N_2O_4S_2$:

| Theory: | C, 56.31 | H, 7.09 | N, 6.57 |
| --- | --- | --- | --- |
| Found: | C, 56.43 | H, 6.99 | N, 6.53 |

EXAMPLE 25

Preparation of [(Methylethyl)sulfonyl]{2-[5-(2-{[(methylethyl)sulfonyl]amino}ethyl)(2-thienyl]ethyl}amine

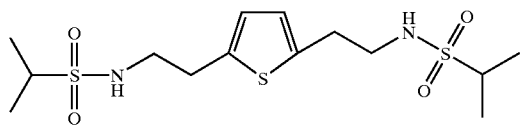

Preparation of (Phenylmethoxy)-N-[2-(5-{2-[(Phenylmethoxy)carbonylamino]ethyl}(2-thienyl))ethyl]carboxamide

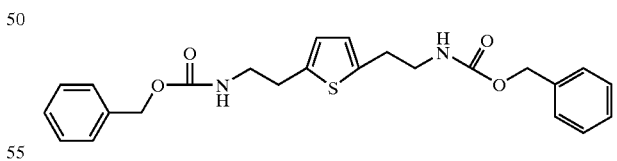

Scheme IV, step A: 2,5-Dibromothiophene (2.4 g, 10 mmol), (phenylmethoxy)-N-vinylcarboxamide (4.42 g, 25 mmol, prepared in example 6), 9-BBN dimer (3.05 g, 12.5 mmol), [1,1'bis(diphenylphosphino)fierrocene] dichloropalladium (II), PdCl$_2$(dppf), (1.23 g, 1.5 mmol), 3N sodium hydroxide (30 mL), and pH=7 buffer: hydrogen peroxide (2:1, 100 mL) were combined in a manner analogous to the procedure described in example 6 to provide the intermediate title, (phenylmethoxy)-N-[2-(5-{2-[(phenylmethoxy)carbonylamino]ethyl}(2-thienyl))ethyl]carboxamide, (3.1 g, 71%).

Preparation of 2-[5-(2-Aminoethyl)-2-thienyl]ethylamine

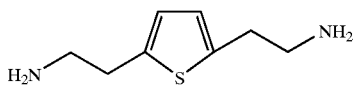

Scheme IV, step B: (Phenylmethoxy)N-[2-(5-{2-[(phenylmethoxy)carbonylamino]ethyl}(2-thienyl))ethyl]carboxamide (1.6 g, 3.6 mmol) and 10% palladium on carbon (1.0 g, 62 mole %) were combined and hydrogenation was carried out in a manner analogous to the procedure described in example 6 to provide the intermediate title compound, 2-[5-(2-aminoethyl)-2-thienyl]ethylamine, (0.935 g, 55%) as a colorless oil.

Preparation of Final Title Compound

Scheme IV, step C: 2-[5-(2-Aminoethyl)-2-thienyl]ethylamine (0.5, 2.9 mmol), isopropylsulfonyl chloride (0.670 mL, 6.1 mmol) and DBU (0.932 mL, 6.1 mmol) were combined and sulfonylation was carried out in a manner analogous to the procedure described in example 2 to provide the final title compound (0.554 g, 50%) as a white crystalline solid.

EXAMPLE 26

Preparation of [(Methylethyl)sulfonyl]{2-[1-methyl-5-(2-{[(methylethyl)sulfonyl]amino}ethyl)benzimidazol-2-yl]ethyl}amine

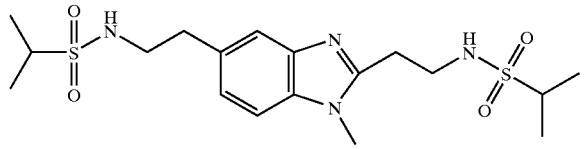

Preparation of 2,5-Dibromo-1-methylbenzimidazole

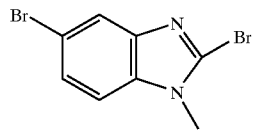

A solution of N-methylbenzimidazole (2 g, 16.93 mmol), N-bromosuccinimide (6 g, 34.03 mmol), and silicagel (0.5 g) in dichloromethane (125 mL) was stirred under nitrogen for 2 days. The mixture was filtered and the filtrate was washed with water (3×50 mL). The combined organic was dried (MgSO$_4$), filtered, and concentrated to give the crude product. Pure 2,5-dibromo-1-methylbenzimidazole was obtained as a white solid by recrystallization of the crude with a 1:1 mixture of CH$_2$Cl$_2$:Hexanes (2.3 g, 50%).

Preparation of N-[2-(1-Methyl-5-{2-[(phenylmethoxy)carbonylamino]ethyl}benzimidazol-2-yl)ethyl](phenylmethoxy)carboxamide

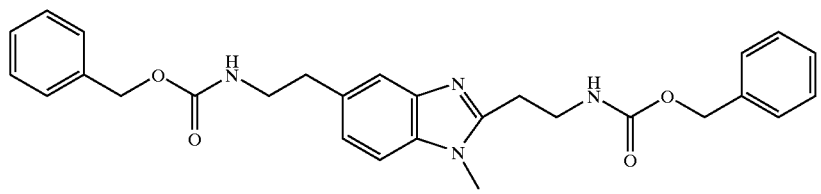

Scheme IV, step A: 2,5-Dibromo-1-methylbenzimidazole (2.76 g, 10 mmol), (phenylmethoxy)N-vinylcarboxamide (4.42 g, 25 mmol, prepared in example 6), 9-BBN dimer (3.05 g, 12.5 mmol), [1,1'bis(diphenylphosphino)-ferrocene]dichloropalladium (11), PdCl$_2$(dppf), (1.23 g, 1.5 mmol), 3N sodium hydroxide (30 mL), and pH=7 buffer hydrogen peroxide (2:1, 100 mL) were combined in a manner analogous to the procedure described in example 6 to provide the intermediate title compound, N-[2-(1-methyl-5-{2-[(phenylmethoxy)carbonylamino]ethyl}benzimidazol-2-yl)ethyl](phenylmethoxy)carboxamide, (41%).

Preparation of 2-[5-(2-Aminoethyl)-1-methylbenzimidazol-2-yl]ethylamine

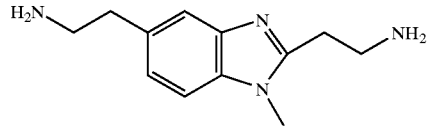

Scheme IV, step B: N-[2-(1-Methyl-5-{2-[(phenylmethoxy)carbonylamino]ethyl}benzimidazol-2-yl)ethyl](phenylmethoxy)carboxamide (3.6 mmol) and 10% palladium on carbon (1.0 g, 62 mole %) were combined and hydrogenation was carried out in a manner analogous to the procedure described in example 6 to provide the intermediate title compound, 2-[5-(2-aminoethyl)-1-methylbenzimidazol-2-yl]ethylamine, (55%) as a colorless oil.

Preparation of Final Title Compound

Scheme IV, step C: 2-[5-(2-Aminoethyl)-1-methylbenzimidazol-2-yl]ethylamine (2.9 mmol), isopropylsulfonyl chloride (0.670 mL, 6.1 mmol) and DBU (0.932 mL, 6.1 mmol) were combined and sulfonylation was carried out in a manner analogous to the procedure described in example 2 to provide the final title compound (50%) as a white crystalline solid

EXAMPLE 27

Preparation of [(Methylethyl)sulfonyl]{2-[6-(2-{[(methylethyl)sulfonyl]amino}ethyl)(3-pyridyl)]ethyl}amine

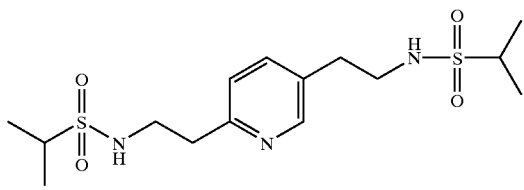

Preparation of (Phenylmethoxy)-N-[2-(6-{2-[(phenylmethoxy)carbonylamino]ethyl}(3-pyridyl))ethyl]carboxamide

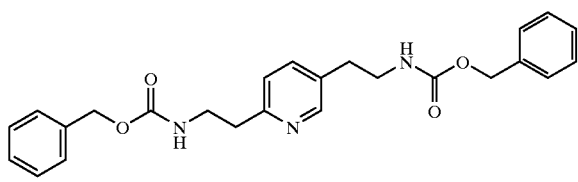

Scheme IV, step A: 2,5-Dibromopyridine (2.4 g, 10 mmol), (phenylmethoxy)-N-vinylcarboxamide (4.42 g, 25 mmol, prepared in example 6), 9-BBN dimer (3.05 g, 12.5 mmol), [1,1'bis(diphenylphosphino)-ferrocene] dichloropalladium (II), $PdCl_2(dppf)$, (1.23 g, 1.5 mmol), 3N sodium hydroxide (30 mL), and pH=7 buffer hydrogen peroxide (2:1, 100 mL) were combined in a manner analogous to the procedure described in example 6 to provide the intermediate title compound, (phenylmethoxy)-N-[2-(6-{2-[(phenylmethoxy)carbonylamino]ethyl}(3-pyridyl))ethyl]carboxamide, (38%).

Preparation of 2-[6-(2-Aminoethyl)-3-pyridyl]ethylamine

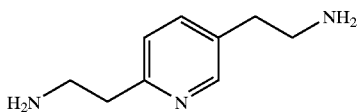

Scheme IV, step B: (Phenylmethoxy)-N-[2-(6-{2-[(phenylmethoxy)carbonylamino]ethyl}(3-pyridyl))ethyl]carboxamide (3.6 mmol) and 10% palladium on carbon (1.0 g, 62 mole %) were combined and hydrogenation was carried out in a manner analogous to the procedure described in example 6 to provide the intermediate title compound, 2-[6-(2-aminoethyl)-3-pyridyl]ethylamine, (55%) as a colorless oil.

Preparation of Final Title Compound

Scheme IV, step C: 2-[6-(2-Sminoethyl)-3-pyridyl]ethylamine (2.9 mmol), isopropylsulfonyl chloride (0.670 mL, 6.1 mmol) and DBU (0.932 mL, 6.1 mmol) were combined and sulfonylation was carried out in a manner analogous to the procedure described in example 2 to provide the final title compound (50%) as a white crystalline solid The ability of compounds of formula I to potentiate glutamate receptor-mediated response may be determined using fluorescent calcium indicator dyes (Molecular Probes, Eugene, Oreg., Fluo-3) and by measuring glutamate-evoked efflux of calcium into GluR4 transfected HEK293 cells, as described in more detail below.

In one test, 96 well plates containing confluent monolayers of HEK 293 cells stably expressing human GluR4B (obtained as described in European Patent Application Publication Number EP-A1-583917) are prepared. The tissue culture medium in the wells is then discarded, and the wells are each washed once with 200 μl of buffer (glucose, 10 mM, sodium chloride, 138 mM, magnesium chloride, 1 mM, potassium chloride, 5 mM, calcium chloride, 5 mM, N-[2-hydroxyethyl]-piperazine-N-[2-ethanesulfonic acid], 10 mM, to pH 7.1 to 7.3). The plates are then incubated for 60 minutes in the dark with 20 μM Fluo3-AM dye (obtained from Molecular Probes Inc., Eugene, Oreg.) in buffer in each well. After the incubation, each well is washed once with 100 μl buffer, 200 μl of buffer is added and the plates are incubated for 30 minutes.

Solutions for use in the test are also prepared as follows. 30 μM, 10 μM, 3 μM and 1 μM dilutions of test compound are prepared using buffer from a 10 mM solution of test compound in DMSO. 100 μM cyclothiazide solution is prepared by adding 3 μl of 100 mM cyclothiazide to 3 mL of buffer. Control buffer solution is prepared by adding 1.5 μl DMSO to 498.5 μl of buffer.

Each test is then performed as follows. 200 μl of control buffer in each well is discarded and replaced with 45 μl of control buffer solution. A baseline fluorescent measurement is taken using a FLUOROSKAN II fluorimeter (Obtained from Labsystems, Needham Heights, Mass., USA, a Division of Life Sciences International Plc). The buffer is then removed and replaced with 45 μl of buffer and 45 μl of test compound in buffer in appropriate wells. A second fluorescent reading is taken after 5 minutes incubation. 15 μl of 400 μM glutamate solution is then added to each well (final glutamate concentration 100 μM), and a third reading is taken. The activities of test compounds and cyclothiazide solutions are determined by subtracting the second from the third reading (fluorescence due to addition of glutamate in the presence or absence of test compound or cydothiazide) and are expressed relative to enhance fluorescence produced by 100 μM cyclothiazide.

In another test, HEK293 cells stably expressing human GluR4 (obtained as described in European Patent Application Publication No. EP-A1-0583917) are used in the electrophysiological characterization of AMPA receptor potentiators. The extracellular recording solution contains (in mM): 140 NaCl, 5 KCl, 10 HEPES, 1 $MgCl_2$, 2 $CaCl_2$, 10 glucose, pH=7.4 with NaOH, 295 mOsm kg-1. The intracellular recording solution contains (in mM): 140 CsCl, 1 $MgCl_2$, 10 HEPES, (N-[2-hydroxyethyl]piperazine-N1-[2-ethanesulfonic acid]) 10 EGTA (ethylene-bis(oxyethylenenitrilo)tetraacetic acid), pH=7.2 with CsOH, 295 mOsm kg-1. With these solutions, recording pipettes have a resistance of 2–3 MΩ. Using the whole-cell voltage clamp technique (Hamill et al.(1981)Pflügers Arch., 391: 85–100), cells are voltage-clamped at −60 mV and control current responses to 1 mM glutamate are evoked. Responses to 1 mM glutamate are then determined in the presence of test compound. Compounds are deemed active in this test if, at a test concentration of 10 μM or less; they produce a greater than 10% increase in the value of the current evoked by 1 mM glutamate.

In order to determine the potency of test compounds, the concentration of the test compound, both in the bathing solution and co-applied with glutamate, is increased in half log units until the maximum effect was seen. Data collected in this manner are fit to the Hill equation, yielding an $EC_{50}$ value, indicative of the potency of the test compound. Reversibility of test compound activity is determined by assessing control glutamate 1 mM responses. Once the control responses to the glutamate challenge are re-established, the potentiation of these responses by 100 μM cyclothiazide is determined by its inclusion in both the bathing solution and the glutamate-containing solution. In this manner, the efficacy of the test compound relative to that of cyclothiazide can be determined.

According to another aspect, the present invention provides a pharmaceutical composition, which comprises a compound of formula I or a pharmaceutically acceptable salt thereof and a pharmaceutically acceptable diluent or carrier.

The pharmaceutical compositions are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 1 mg to about 500 mg, more preferably about 5 mg to about 300 mg (for example 25 mg) of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient.

As used herein the term "patient" refers to a mammal, such as a mouse, guinea pig, rat, dog or human. It is understood that the preferred patient is a human.

As used herein, the terms "treating" or "to treat" each mean to alleviate symptoms, eliminate the causation either on a temporary or permanent basis, or to prevent or slow the appearance of symptoms of the named disorder. As such, the methods of this invention encompass both therapeutic and prophylactic administration.

As used herein, the term "effective amount" refers to the amount of a compound of formula I which is effective, upon single or multiple dose administration to a patient, in treating the patient suffering from the named disorder.

An effective amount can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds can be administered by a variety of routes including oral, rectal, transdermal, subcutaneous, intravenous, intramuscular, bucal or intranasal routes. Alternatively, the compound may be administered by continuous infusion. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

The compounds of formula I as a class are particularly useful in the treatment methods of the present invention, but certain groups, substituents, and configurations are preferred for compounds of formula I. The following paragraphs describe such preferred groups, substituents, and configurations. It will be understood that these preferences are applicable both to the treatment methods and to the new compounds of the present invention.

a) $R^1$ is preferably (1–4C)alkyl, $N(CH_3)_2$, or $NH(CH_3)$, most preferably methyl, ethyl, propyl or 2-propyl, and it is most especially preferred that $R^1$ is 2-propyl;

b) $R^2$ is preferably hydrogen, F, methyl, ethyl, propyl, hydroxy, or methoxy, and most preferably hydrogen, F, or methyl;

c) $R^3$ is preferably hydrogen, F, methyl, ethyl, propyl, hydroxy, or methoxy, and most preferably hydrogen, F, or methyl;

d) $R^{4a}$ is preferably hydrogen, F, methyl, ethyl, methoxy, or ethoxy, and most preferably hydrogen, F, methyl or methoxy, and most especially preferably hydrogen;

e) $R^{4b}$ is preferably hydrogen, F, methyl, ethyl, methoxy, or ethoxy, and most preferably hydrogen, F, methyl or methoxy, and most especially preferably hydrogen;

f) $R^5$ is preferably hydrogen, F, methyl, ethyl, hydroxy, methoxy, or ethoxy, most preferably hydrogen, F, methyl or methoxy, and it is most especially preferred that $R^5$ is F or methyl;

g) $R^6$ is preferably hydrogen, F, methyl, ethyl, hydroxy, methoxy, or ethoxy, most preferably hydrogen, F, methyl or methoxy, and it is most especially preferred that $R^6$ is F or methyl;

h) $R^7$ is preferably hydrogen or methyl, and most preferably hydrogen;

i) $R^8$ is preferably methyl, ethyl, propyl or 2-propyl and most preferably 2-propyl;

j) $R^9$ is preferably hydrogen or methyl;

k) $R^{10}$ is preferably hydrogen or methyl;

l) $R^{11}$ is preferably hydrogen, methyl or ethyl, and most preferably hydrogen;

m) n is preferably zero, 1, 2 or 3, and most preferably zero or 1;

n) m is preferably 1, 2 or 3, and most preferably 1 or 2;

o) When $R^{4a}$ is hydrogen, $R^{4b}$ is preferably hydrogen, F, methyl, ethyl, methoxy, or ethoxy, and most preferably $R^{4b}$ is hydrogen, F, methyl or methoxy; and when $R^{4b}$ is hydrogen, $R^{4a}$ is preferably hydrogen, F, methyl, ethyl, methoxy, or ethoxy, and most preferably $R^{4a}$ is hydrogen, F, methyl or methoxy;

p) When $R^2$ is hydrogen, $R^3$ is preferably F or methyl;

q) When $R^3$ is hydrogen, $R^2$ is preferably F or methyl;

r) p is preferably 1;

s) A is preferably;

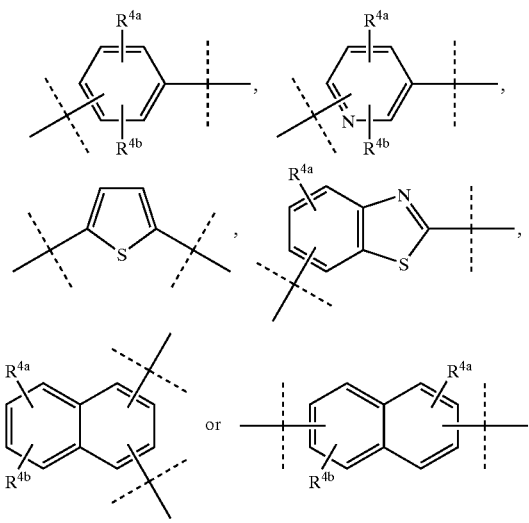

and most preferably;

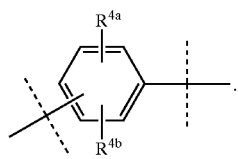

We claim:

1. A compound of the formula:

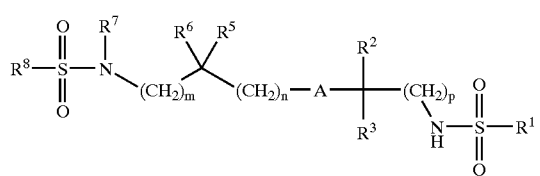

wherein A represents

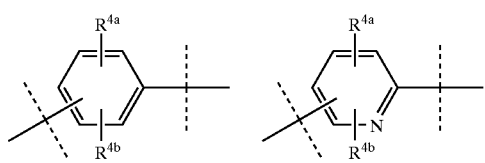

-continued

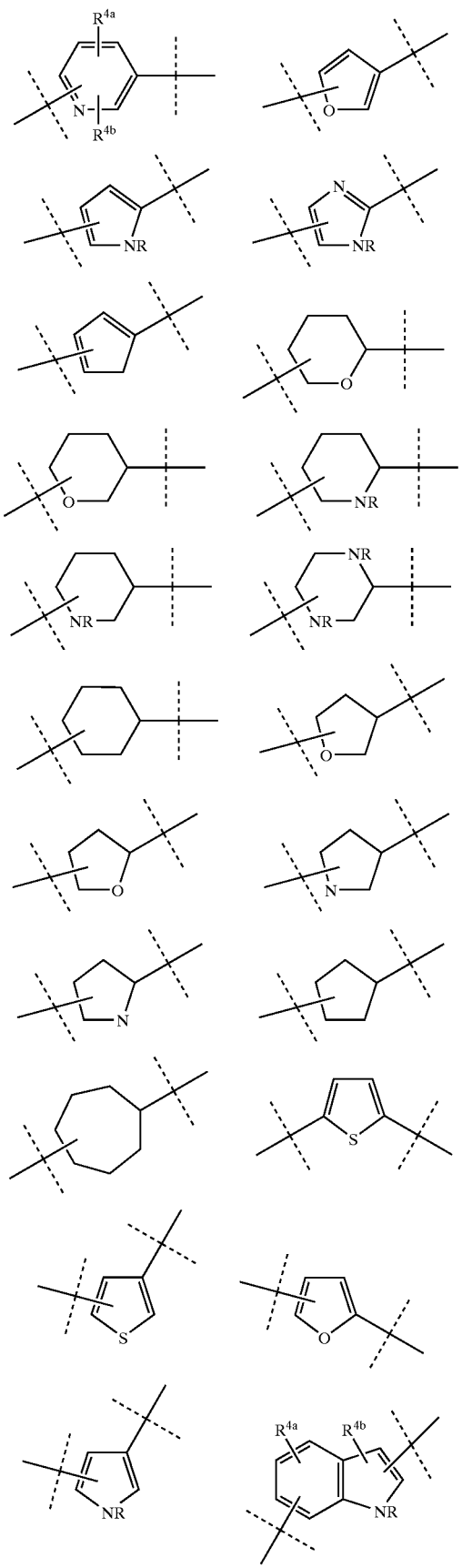

-continued

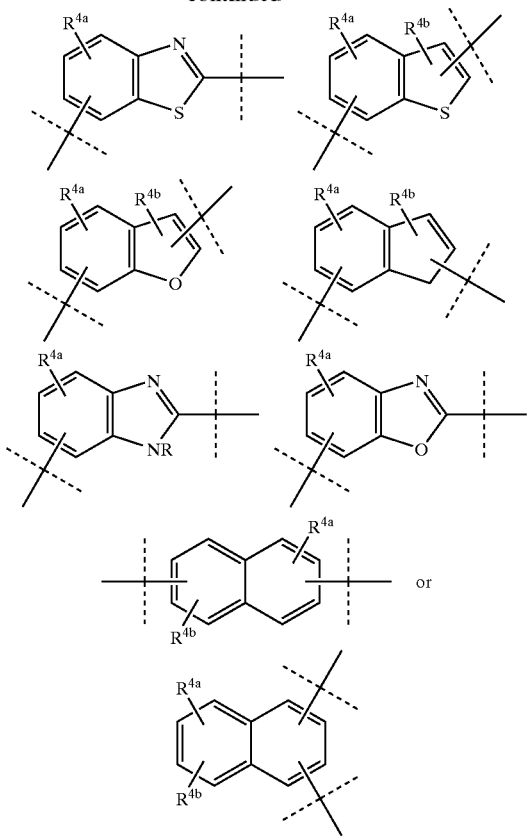

R represents hydrogen or (1–4C)alkyl;
R$^1$ represents (1–6C)alkyl, (2–6C)alkenyl, or NR$^9$R$^{10}$;
R$^2$ and R$^3$ each independently represent hydrogen, (1–4C)alkyl, F, or —OR$^{11}$;
R$^{4a}$ and R$^{4b}$ each independently represent hydrogen, (1–4C) alkyl, (1–4C)alkoxy, I, Br, Cl, or F;
R$^5$ and R$^6$ each independently represent hydrogen, (1–4C)alkyl, F, or —OR$^{11}$;
R$^7$ represents hydrogen, or (1–4C)alkyl;
R$^8$ represents (1–6C)alkyl, unsubstituted or substituted aromatic group, unsubstituted or substituted heteroaromatic group, cycloalkyl, or alkylcycloalkyl;
n is zero or an integer 1, 2, 3, 4, or 5;
m is zero or an integer 1, 2, 3, 4, or 5;
p is an integer 1 or 2;
R$^9$ and R$^{10}$ each independently represent hydrogen or (1–4C)alkyl; and
R$^{11}$ represents hydrogen or (1–4C)alkyl;
or a pharmaceutically acceptable salt thereof.

2. A compound according to claim 1 wherein R$^1$ is (1–4C)alkyl.

3. A compound according to claim 2 wherein R$^8$ is (1–4C)alkyl.

4. A compound according to claim 3 wherein R$^1$ is 2-propyl.

5. A compound according to claim 4 wherein R$^8$ is 2-propyl.

6. A compound according to claim 5 wherein R$^7$ is hydrogen.

7. A compound according to claim 6 wherein p is 1.

8. A compound according to claim 7 wherein m is 1 or 2.

9. A compound according to claim 8 wherein n is zero.

10. A compound according to claim 9 wherein R$^5$ and R$^6$ are each hydrogen.

11. A compound according to claim 10 wherein R$^{4a}$ and R$^{4b}$ are each independently hydrogen, F, methyl, or methoxy.

12. A compound according to claim 11 wherein R$^2$ is F or methyl and R$^3$ is hydrogen.

13. A compound according to claim 12 wherein R$^2$ is methyl.

14. A compound according to claim 13 wherein A represents:

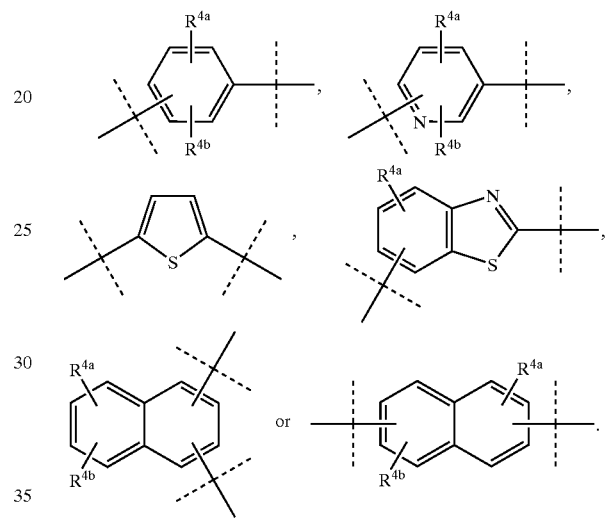

15. A compound according to claim 14 wherein A represents;

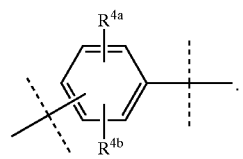

16. A compound according to claim 15 wherein R$^{4a}$ and R$^{4b}$ represent hydrogen.

17. A pharmaceutical composition, which comprises a compound according to claim 1, and a pharmaceutically acceptable diluent or carrier.

18. A method of potentiating glutamate receptor function in a patient, which comprises administering to said patient an effective amount of a compound of formula:

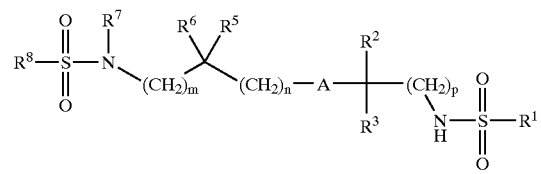

wherein A represents

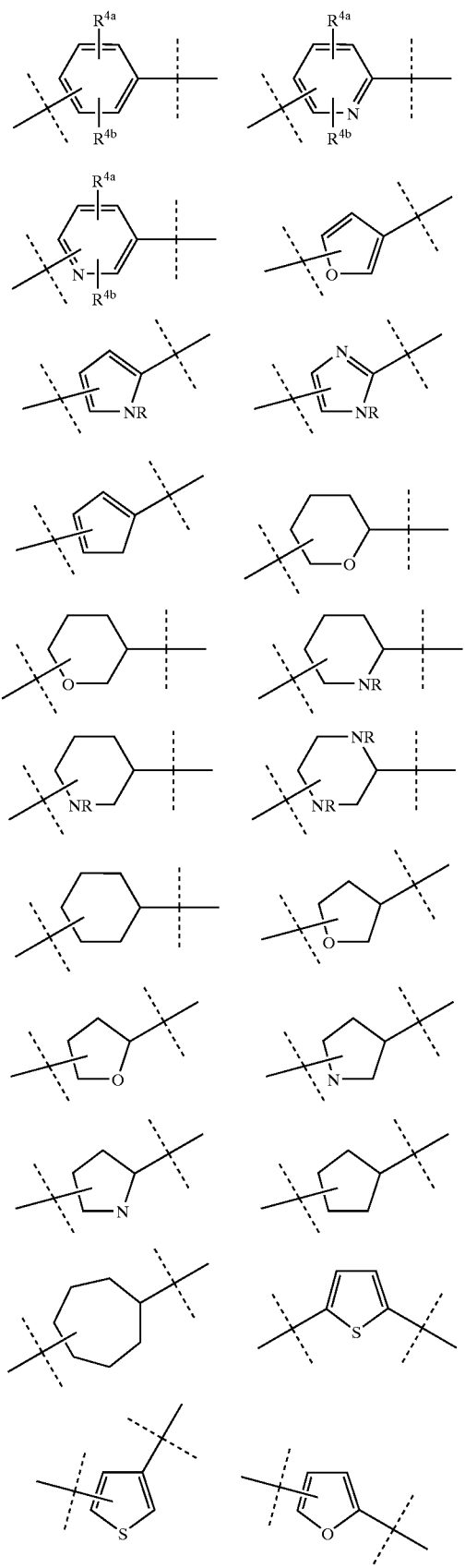

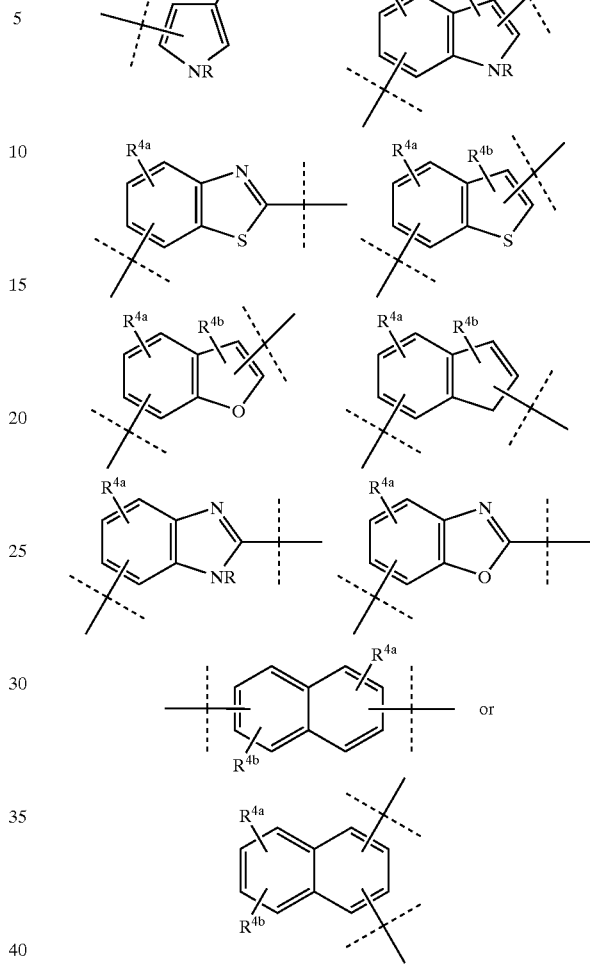

R represents hydrogen or (1–4C)alkyl;

$R^1$ represents (1–6C)alkyl, (2–6C)alkenyl, or $NR^9R^{10}$;

$R^2$ and $R^3$ each independently represent hydrogen, (1–4C) alkyl, F, or —$OR^{11}$;

$R^{4a}$ and $R^{4b}$ each independently represent hydrogen, (1–4C) alkyl, (1–4C)alkoxy, I, Br, Cl, or F;

$R^5$ and $R^6$ each independently represent hydrogen, (1–4C) alkyl, F, or —$OR^{11}$;

$R^7$ represents hydrogen, or (1–4C)alkyl;

$R^8$ represents (1–6C)alkyl, unsubstituted or substituted aromatic group, unsubstituted or substituted heteroaromatic group, cycloalkyl, or alkylcycloalkyl;

n is zero or an integer 1, 2, 3, 4, or 5;

m is zero or an integer 1, 2, 3, 4, or 5;

p is an integer 1 or 2;

$R^9$ and $R^{10}$ each independently represent hydrogen or (1–4C)alkyl; and $R^{11}$ represents hydrogen or (1–4C)alkyl;

or a pharmaceutically acceptable salt thereof.

19. A method of treating Alzheimer's disease in a patient, which comprises administering to said patient in need thereof an effective amount of a compound of formula:

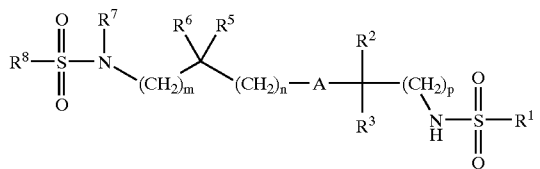

wherein A represents

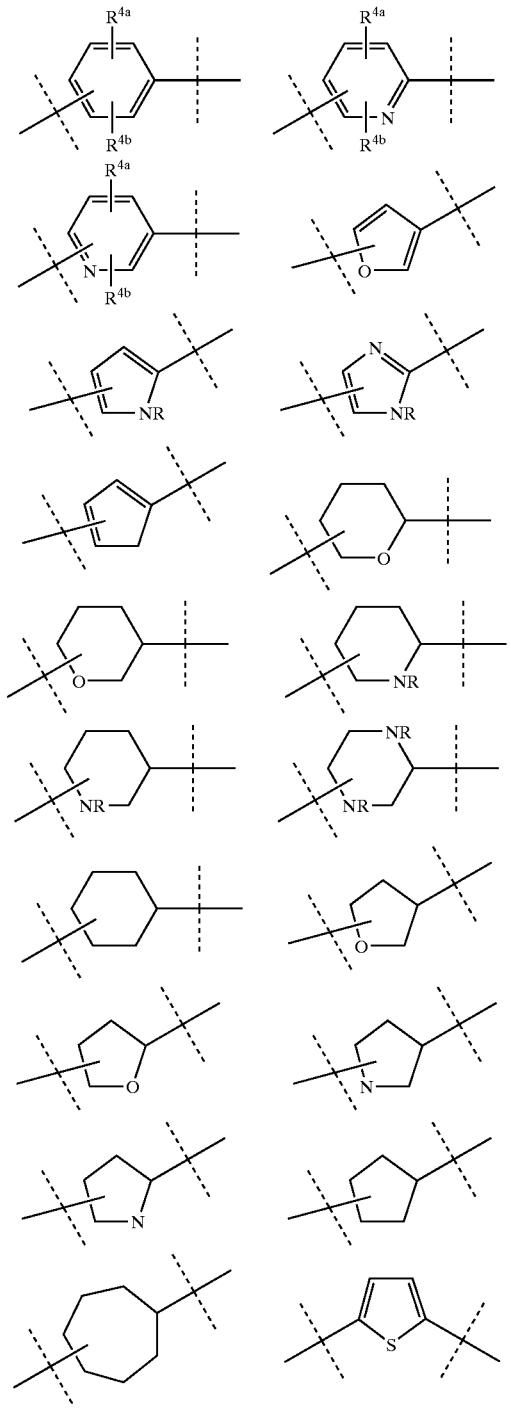

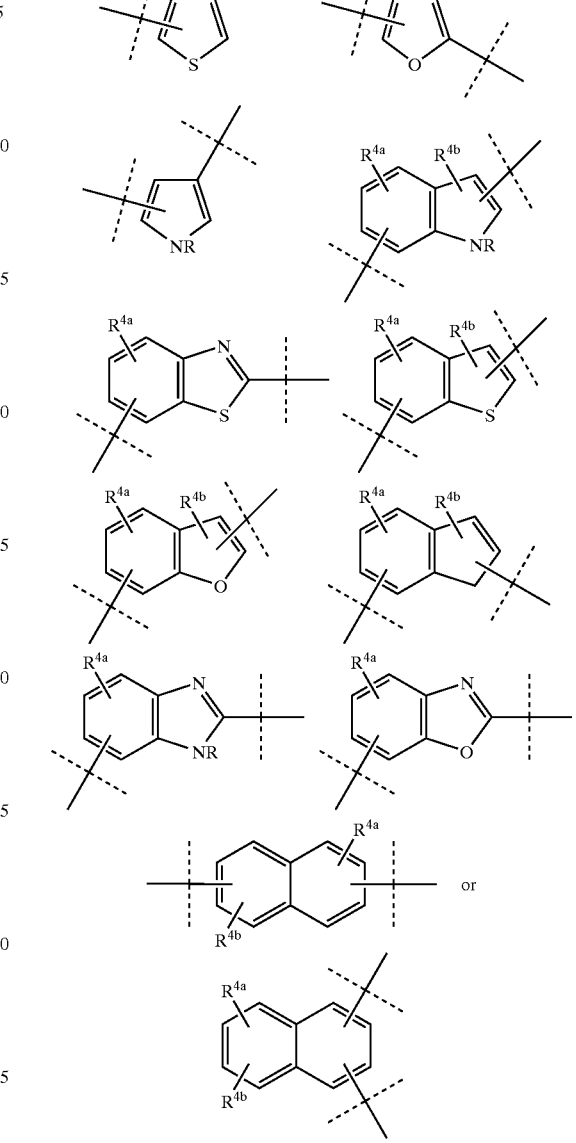

R represents hydrogen or (1–4C)alkyl;

$R^1$ represents (1–6C)alkyl, (2–6C)alkenyl, or $NR^9R^{10}$;

$R^2$ and $R^3$ each independently represent hydrogen, (1–4C) alkyl, F, or —$OR^{11}$;

$R^{4a}$ and $R^{4b}$ each independently represent hydrogen, (1–4C) alkyl, (1–4C)alkoxy, I, Br, Cl, or F;

$R^5$ and $R^6$ each independently represent hydrogen, (1–4C) alkyl, F, or —$OR^{11}$;

$R^7$ represents hydrogen, or (1–4C)alkyl;

$R^8$ represents (1–6C)alkyl, unsubstituted or substituted aromatic group, unsubstituted or substituted heteroaromatic group, cycloalkyl, or alkylcycloalkyl;

n is zero or an integer 1, 2, 3, 4, or 5;

m is zero or an integer 1, 2, 3, 4, or 5;

p is an integer 1 or 2;

$R^9$ and $R^{10}$ each independently represent hydrogen or (1–4C)alkyl; and $R^{11}$ represents hydrogen or (1–4C)alkyl;

or a pharmaceutically acceptable salt thereof.

20. A method of treating Parkinson's disease in a patient, which comprises administering to said patient in need thereof an effective amount of a compound of formula:

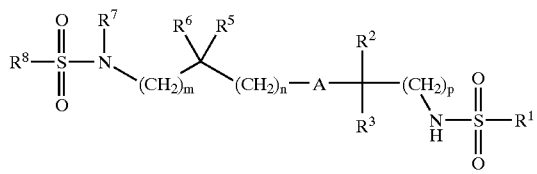

wherein A represents

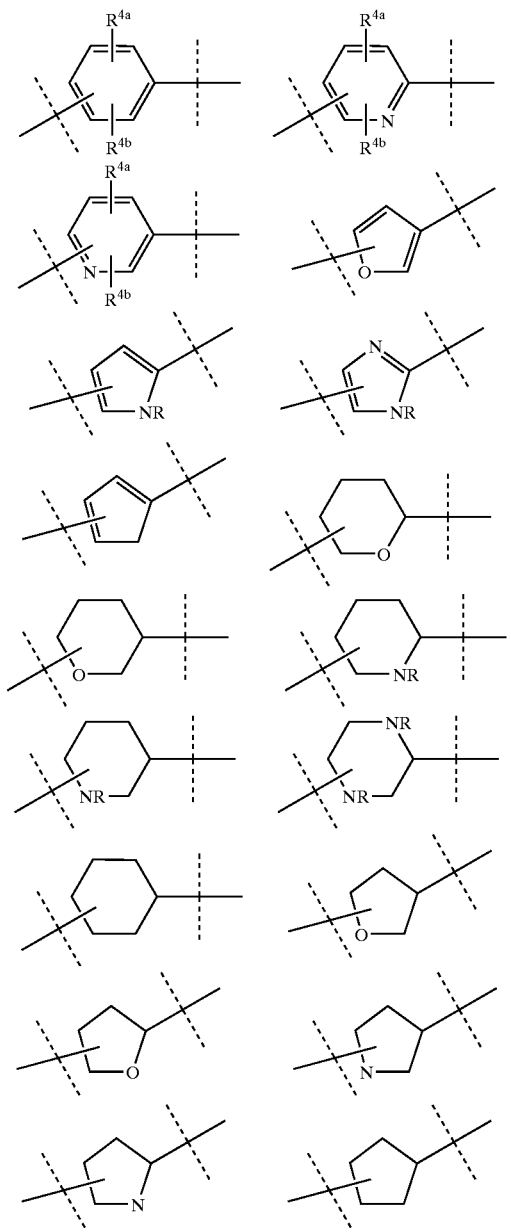

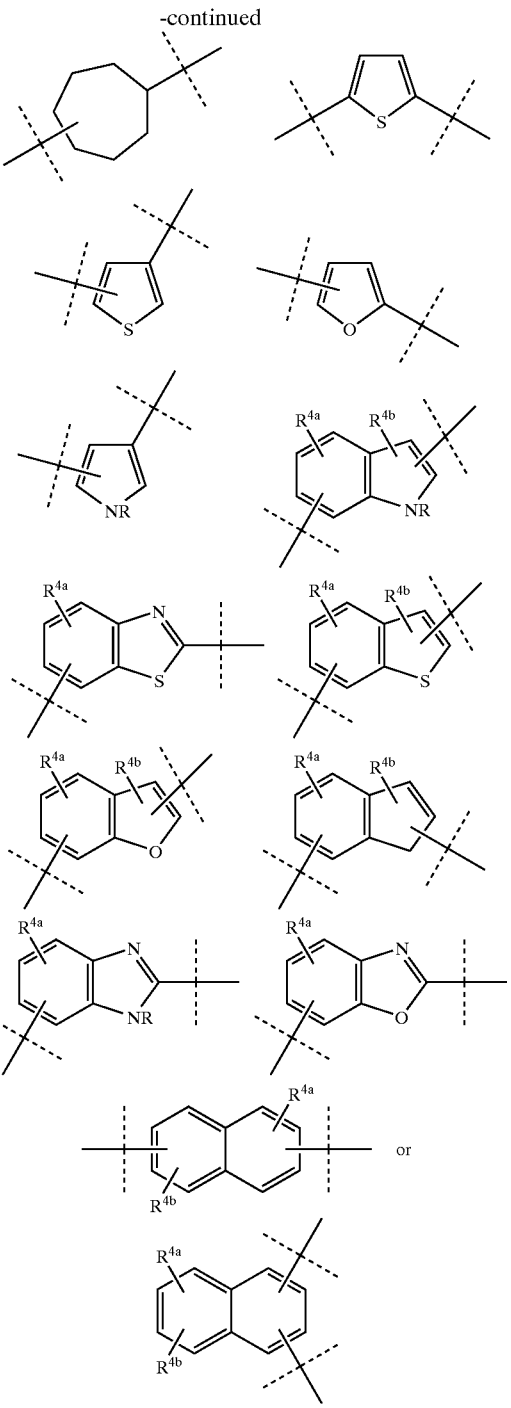

R represents hydrogen or (1–4C)alkyl;

$R^1$ represents (1–6C)alkyl, (2–6)alkenyl, or $NR^9R^{10}$;

$R^2$ and $R^3$ each independently represent hydrogen, (1–4C) alkyl, F, or —$OR^{11}$;

$R^{4a}$ and $R^{4b}$ each independently represent hydrogen, (1–4C) alkyl, (1–4C)alkoxy, I, Br, Cl, or F;

$R^5$ and $R^6$ each independently represent hydrogen, (1–4C) alkyl, F, or —$OR^{11}$;

$R^7$ represents hydrogen, or (1–4C)alkyl;

$R^8$ represents (1–6C)alkyl, unsubstituted or substituted aromatic group, unsubstituted or substituted heteroaromatic group, cycloalkyl, or alkylcycloalkyl;

n is zero or an integer 1, 2, 3, 4, or 5;

m is zero or an integer 1, 2, 3, 4, or 5;

p is an integer 1 or 2;

$R^9$ and $R^{10}$ each independently represent hydrogen or (1–4C)alkyl; and $R^{11}$ represents hydrogen or (1–4C)alkyl;

or a pharmaceutically acceptable salt thereof.

21. A method of treating cognitive disorders in a patient, which comprises administering to said patient in need thereof an effective amount of a compound of formula:

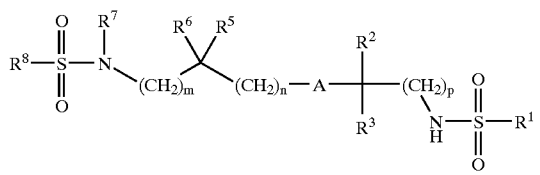

wherein A represents

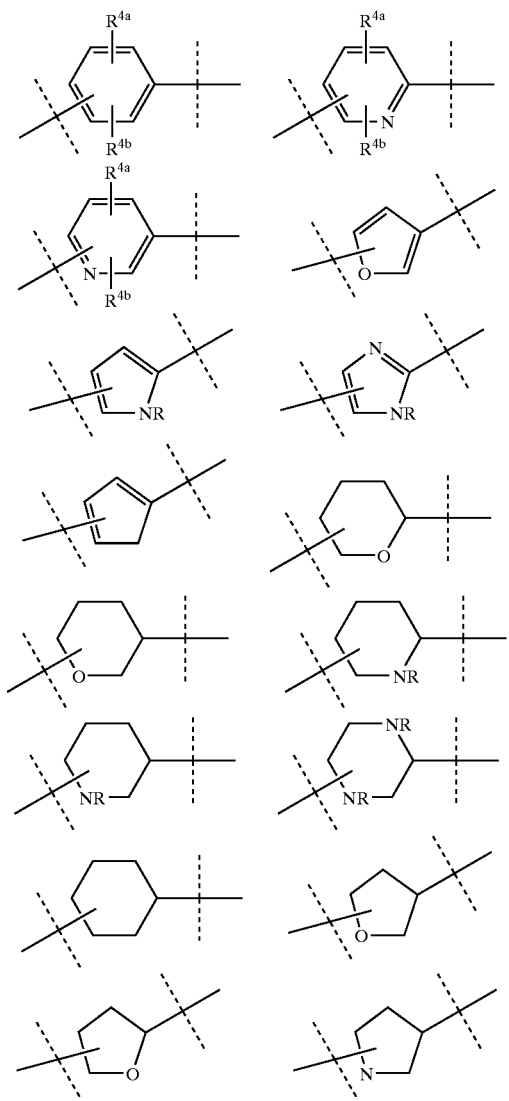

-continued

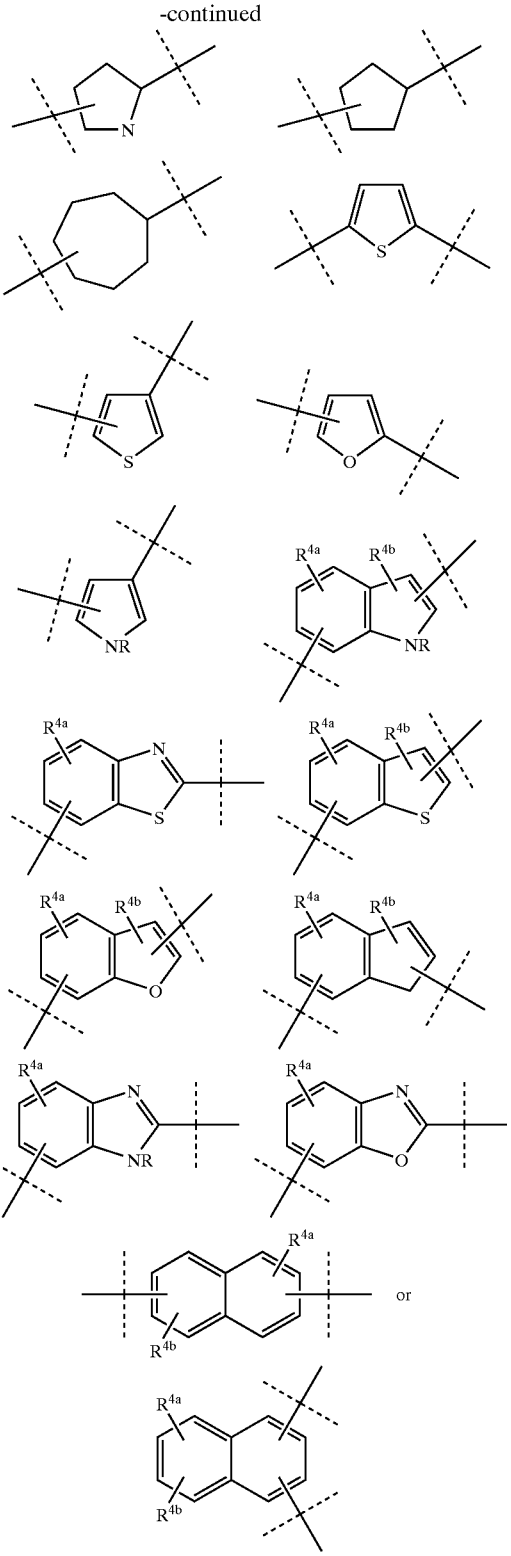

R represents hydrogen or (1–4C)alkyl;

$R^1$ represents (1–6C)alkyl, (2–6C)alkenyl, or $NR^9R^{10}$;

$R^2$ and $R^3$ each independently represent hydrogen, (1–4C)alkyl, F, or —$OR^{11}$;

R$^{4a}$ and R$^{4b}$ each independently represent hydrogen, (1–4C) alkyl, (1–4C)alkoxy, I, Br, Cl, or F;

R$^5$ and R$^6$ each independently represent hydrogen, (1–4C) alkyl, F, or —OR$^{11}$;

R$^7$ represents hydrogen, or (1–4C)alkyl;

R$^8$ represents (1–6C)alkyl, unsubstituted or substituted aromatic group, unsubstituted or substituted heteroaromatic group, cycloalkyl, or alkylcycloalkyl;

n is zero or an integer 1, 2, 3, 4, or 5;

m is zero or an integer 1, 2, 3, 4, or 5;

p is an integer 1 or 2;

R$^9$ and R$^{10}$ each independently represent hydrogen or (1–4C)alkyl; and

R$^{11}$ represents hydrogen or (1–4C)alkyl;

or a pharmaceutically acceptable salt thereof.

22. A compound according to claim 12 wherein A represents:

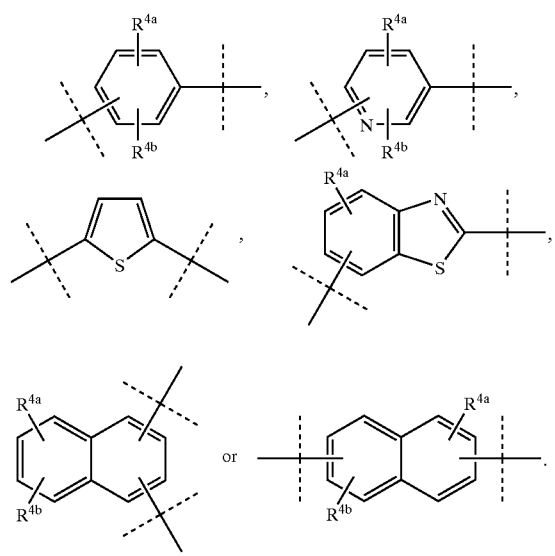

23. A compound according to claim 11 wherein A represents:

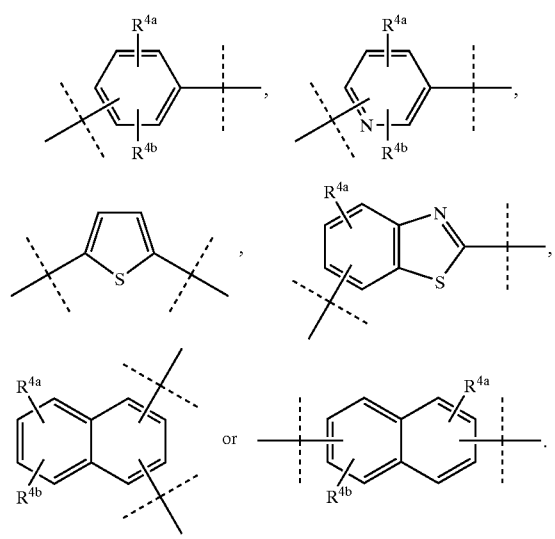

24. A compound according to claim 10 wherein A represents:

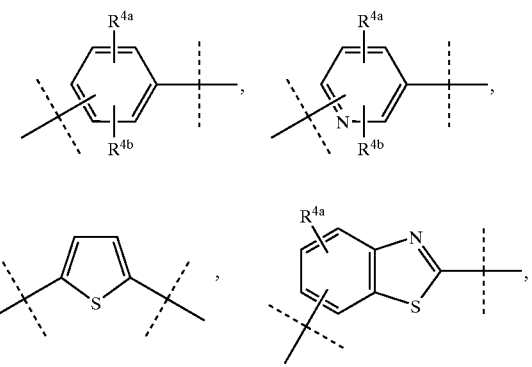

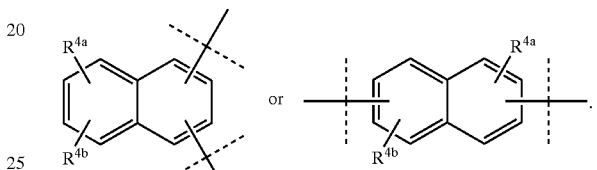

25. A compound according to claim 9 wherein A represents:

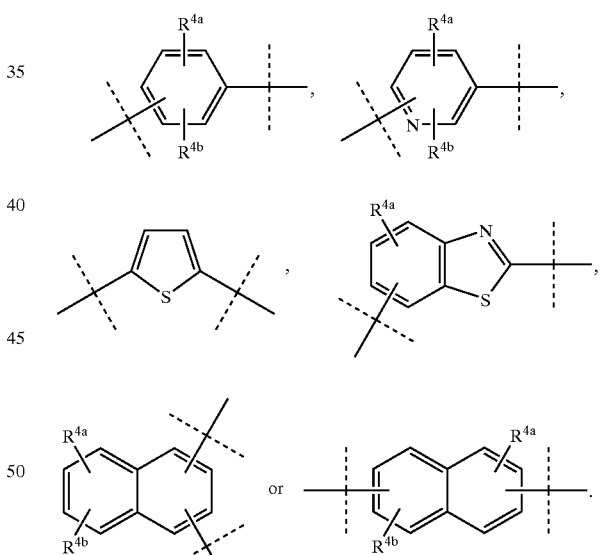

26. A compound according to claim 8 wherein A represents:

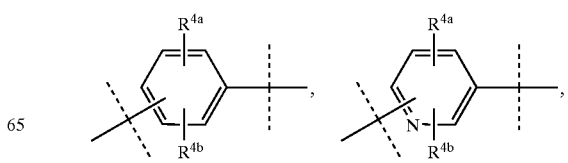

-continued
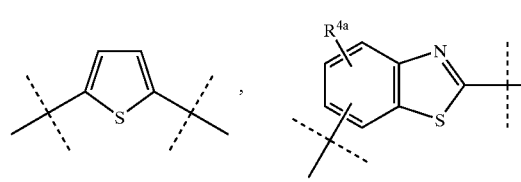
-continued
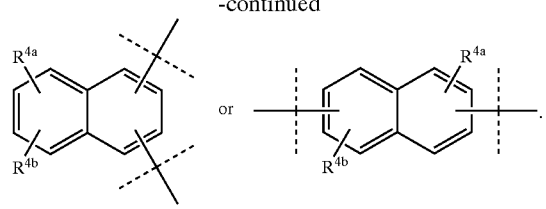
* * * * *